United States Patent [19]
Gregory et al.

[11] Patent Number: 5,882,877
[45] Date of Patent: Mar. 16, 1999

[54] ADENOVIRAL VECTORS FOR GENE THERAPY CONTAINING DELETIONS IN THE ADENOVIRAL GENOME

[75] Inventors: Richard J. Gregory, Westford; Donna Armentano, Belmont, both of Mass.; Larry A. Couture, Louisville, Colo.; Alan E. Smith, Dover, Mass.

[73] Assignee: Genzyme Corporation, Framingham, Mass.

[21] Appl. No.: 895,194

[22] Filed: Jul. 16, 1997

Related U.S. Application Data

[63] Continuation of Ser. No. 136,742, Oct. 13, 1993, Pat. No. 5,670,488, which is a continuation-in-part of Ser. No. 985,478, Dec. 3, 1992, abandoned.

[51] Int. Cl.$^6$ ............................. C12N 15/00; C12N 15/86
[52] U.S. Cl. ........................ 435/320.1; 435/456; 435/457
[58] Field of Search .............................. 435/320.1, 172.3, 435/456, 457

[56] References Cited

FOREIGN PATENT DOCUMENTS

WO 9529993  11/1995  WIPO .
WO 9613597   5/1996  WIPO .
WO 9640955  12/1996  WIPO .

OTHER PUBLICATIONS

Abstract, Couture et al., "The Use of Alternative Vectors for Gene Transfer to Lung Epithelia and Tissue Culture Cells," *Pediatric Pulmonology*, Supplement 8, Sep. 1992.

Klessig et al (1984) Molec. Cell Biol. 4, 1354–1362.

Rosenfeld et al (1991) Science 252, 431–434.

Davidson et al (1987) J. Virol. 61, 1226–1229.

Ferry et al (1991) Proced. Natl. Acad. Sci 88, 8377–8381.

Wang et al (1996) Molecular Med. 2, 714–716.

Graham et al (1991) Meth. Mole Biol. 7, 109–127 (odd pages).

Ketner et al (1989) Nuc. Acids Res. 17, 3037–3047.

Berkner (1992) "Exp. Heterol. Seq. in Adenoviral Vectors" current Topics Immin. Microbiol. 158, 39–66.

Drumm et al (1990) Cell 62, 1227–1233.

Gha Has et al (1991) Molec. Cell Biol. 11, 5848–5859.

Berkner, Kathleen L., "Development of Adenovirus Vectors for the Expression of Heterologous Genes," *Bio Techniques* 6:616–629, 1998.

*Primary Examiner*—Deborah Crouch
*Attorney, Agent, or Firm*—Baker & Botts, LLP

[57] ABSTRACT

Adenoviral vectors which contain deletions of the early regions and/or late genes provide efficient delivery and expression of foreign nucleic acids of interest to patients. These vectors have a particular use in the treatment of cystic fibrosis patients. Furthermore, PAV vectors provide for a second generation of adenoviral vectors that contain the 5' ITR's, the packaging signal and the E1A enhancer. Other adenoviral vectors contain a deletion of the E1 region or a deletion of E4 but retain orf3 or orf6, and can either retain or delete the E3 region.

21 Claims, 44 Drawing Sheets

PARTIAL cDNA CLONES OF THE CFTR GENE

PAV I CLONING CASSETTE pBluescript SK II

EXPRESSION CASSETTE pBluescript SK II

CLINICAL SIGNS: MONKEY C  AGE 7 YEARS

| DATE | EXAMINATION | HEART RATE (beats/min) | RESP RATE (breath/min) | TEMPERATURE (Celsius) | WEIGHT (Kg) |
|---|---|---|---|---|---|
| 5/11/93 | NORMAL | 112 | 16 | 37.8 | 6.4 |
| 5/11/93 | INFECTION | | | | |
| 5/14/93 | NORMAL | 98 | 14 | 38.1 | |
| 5/18/93 | NORMAL | 104 | 16 | 38.3 | |
| 6/4/93 | NORMAL | 108 | 16 | 38.2 | |
| 6/18/93 | NORMAL | 112 | 16 | 38.4 | |
| 6/24/93 | NORMAL | 116 | 18 | 38.8 | |
| 6/24/93 | INFECTION | | | | |
| 6/28/93 | NORMAL | 104 | 18 | 37.9 | |
| 7/5/93 | granulation | 116 | 16 | 37.4 | |
| 7/13/93 | NORMAL | 114 | 20 | 38.3 | |
| 9/17/93 | NORMAL | 108 | 16 | 38.3 | 7 |

FIG. 30A

CLINICAL SIGNS: MONKEY D  AGE 7 YEARS

| DATE | EXAMINATION | HEART RATE (beats/min) | RESP RATE (breath/min) | TEMPERATURE (Celsius) | WEIGHT (Kg) |
|---|---|---|---|---|---|
| 5/11/93 | NORMAL | 108 | 18 | 38.3 | 6.25 |
| 5/11/93 | INFECTION | | | | |
| 5/14/93 | NORMAL | 100 | 20 | 38.4 | |
| 5/18/93 | NORMAL | 98 | 20 | 38.4 | |
| 6/4/93 | NORMAL | 106 | 18 | 37.9 | |
| 6/18/93 | NORMAL | 100 | 19 | 38.4 | |
| 6/24/93 | NORMAL | 106 | 16 | 37.8 | |
| 6/24/93 | INFECTION | | | | |
| 6/28/93 | NORMAL | 104 | 16 | 37.4 | |
| 7/5/93 | NORMAL | 102 | 14 | 38.8 | |
| 7/12/93 | granulation | 114 | 16 | 38 | |
| 9/17/93 | NORMAL | 104 | 16 | 38.3 | 6.4 |

FIG. 30B

CLINICAL SIGNS: MONKEY E          AGE 11 YEARS

| DATE | EXAMINATION | HEART RATE (beats/min) | RESP RATE (breath/min) | TEMPERATURE (Celsius) | WEIGHT (Kg) |
|---|---|---|---|---|---|
| 5/11/93 | NORMAL | 120 | 18 | 28.3 | 10 |
| 5/11/93 | INFECTION | | | | |
| 5/14/93 | NORMAL | 112 | 20 | 37.9 | |
| 5/18/93 | NORMAL | 108 | 22 | 38.4 | |
| 6/4/93 | NORMAL | 112 | 20 | 38.3 | |
| 6/18/93 | NORMAL | 106 | 20 | 38.3 | |
| 6/24/93 | NORMAL | 108 | 18 | 38.9 | |
| 6/24/93 | INFECTION | | | | |
| 6/28/93 | NORMAL | 112 | 20 | 38 | |
| 7/5/93 | NORMAL | 106 | 22 | 38.3 | |
| 7/12/93 | NORMAL | 114 | 16 | 38 | |
| 9/17/93 | NORMAL | 114 | 16 | 38.3 | 8.75 |

FIG. 30C

CLINICAL LAB RESULTS FROM MONKEY C

| DATE | 11-May | 14-May | 18-May | 4-Jun | 18-Jun | 24-Jun | 24-Jun | 12-Jul | 17-Sep |
|---|---|---|---|---|---|---|---|---|---|
| WBC/mm3 | 6.7 | 9 | 8.9 | 7.1 | 7.9 | 7.3 | | 10.6 | 8.1 |
| NEUT/mm3 | 1850 | 3990 | 3060 | 1480 | 3550 | 3450 | | 2210 | 3950 |
| LYMP/mm3 | 4460 | 4220 | 4770 | 4780 | 3640 | 2670 | | 7270 | 3770 |
| MONO/mm3 | 120 | 520 | 600 | 360 | 420 | 550 | | 480 | 340 |
| EOS/mm3 | 30 | 110 | 190 | 120 | 80 | 400 | | 480 | 340 |
| HEMOG, gr/dl | 12.2 | 12 | 12.6 | 12.8 | 14 | 13.5 | | 13.7 | 13.9 |
| HEMATOCR. % | 38 | 38 | 42 | 41 | 45 | 39 | S | 46 | 43 |
| PLAT k/mm3 | 311 | 319 | 343 | 338 | 308 | 281 | E | 324 | 432 |
| ESR | <1 | 1 | 1 | 1 | 0 | <1 | C | <1 | <1 |
| | | | | | | | O | | |
| NA mEq/l | 149 | 148 | 147 | | 151 | 147 | N | 149 | 153 |
| K mEq/l | 3.6 | 3.6 | 2.6 | | 3.6 | 3.1 | D | 3.4 | 3.6 |
| Cl mEq/l | 111 | 106 | 107 | | 112 | 108 | | 109 | 113 |
| CO2 mEq/l | 19 | 20 | 20 | | 22 | 21 | I | 19 | 19 |
| BUN mg/dl | 11 | 18 | 11 | | 14 | 13 | N | 16 | 23 |
| CREAT mg/dl | 1.1 | 1 | 1.2 | | 1.1 | 1 | F | 1.1 | 1.2 |
| GLUCOSE mg/dl | 68 | 56 | 81 | | 67 | 87 | E | 74 | 58 |
| ALB gr/dl | 4.7 | 4.3 | 4.7 | | 4.9 | 4.2 | C | 4.5 | 4.5 |
| T. PROT, gr/dl | 7.3 | 6.7 | 7.1 | | 7.4 | 6.9 | T | 7.1 | 7.4 |
| CALCIUM mg/dl | 10 | 9.3 | 9.9 | | 10.2 | 9 | I | 10.1 | 9.5 |
| PO4 mg/dl | 3.3 | 5.9 | 5.7 | | 2.9 | 5 | O | 3.7 | 3.4 |
| ALK. PH IU/l | 117 | 376 | 375 | | 117 | 76 | N | 116 | 164 |
| TOT BIL mg/dl | 0.3 | 0.2 | 0.2 | | 0.2 | 0.1 | | 0.2 | 0.3 |
| AST IU/l | 38 | 37 | 45 | | 28 | 25 | | 45 | 34 |
| LDH IU/l | 601 | 599 | 740 | | 277 | 406 | | 458 | 220 |
| URIC Ac mg/dl | 0.1 | 0.1 | <0.1 | | 0.1 | 0.1 | | <0.1 | 0.1 |

FIG. 31A

CLINICAL LAB RESULTS FROM MONKEY D

| DATE | 11-May | 14-May | 18-May | 4-Jun | 18-Jun | 24-Jun | 24-Jun | 12-Jul | 17-Sep |
|---|---|---|---|---|---|---|---|---|---|
| WBC/mm3 | 7 | 4.2 | 9.9 | 6.7 | 9.1 | 6.9 | S | 9.4 | 8.3 |
| NEUT/mm3 | 2860 | 1980 | 3060 | 1090 | 6230 | 1740 | E | | 3160 |
| LYMP/mm3 | 3660 | 4180 | 6100 | 4770 | 1820 | 4750 | C | | 3230 |
| MONO/mm3 | 160 | 410 | 340 | 500 | 500 | 190 | O | | 670 |
| EOS/mm3 | 50 | 150 | 210 | 110 | 240 | 130 | N | | 210 |
| HEMOG, gr/dl | 10.9 | 13.7 | 14.7 | 13.6 | 13.9 | 13.6 | D | | 14.5 |
| HEMATOCR. % | 35 | 42 | 49 | 44 | 43 | 43 | | 44 | 47 |
| PLAT k/mm3 | 268 | 277 | 413 | 369 | 265 | 300 | I | 284 | 348 |
| ESR | 1 | 2 | <1 | 1 | 0 | <1 | N | <1 | <1 |
| NA mEq/l | 147 | 150 | 150 | | 149 | 147 | F | 148 | 148 |
| K mEq/l | 3.5 | 3.5 | 3.6 | | 3.5 | 3.4 | E | 3.5 | 3 |
| Cl mEq/l | 109 | 106 | 110 | | 111 | 108 | C | 109 | 109 |
| CO2 mEq/l | 19 | 20 | 20 | | 23 | 20 | T | 19 | 16 |
| BUN mg/dl | 19 | 18 | 20 | | 10 | 16 | I | 18 | 12 |
| CREAT mg/dl | 1.1 | 1 | 1.1 | | 1.1 | 1 | O | 1 | 1 |
| GLUCOSE mg/dl | 65 | 81 | 72 | | 92 | 78 | N | 66 | 88 |
| ALB gr/dl | 4.3 | 4.7 | 5.2 | | 4.2 | 4.6 | | 4.5 | 4.7 |
| T. PROT, gr/dl | 6.6 | 7.4 | 7.8 | | 6.8 | 6.8 | | 7.1 | 7.6 |
| CALCIUM mg/dl | 9.3 | 10.1 | 10.4 | | 9.6 | 9 | | 10.3 | 9.5 |
| PO4 mg/dl | 6.2 | 3.5 | 3.6 | | 2.8 | 5 | | 5.6 | 4.7 |
| ALK. PH IU/l | 426 | 104 | 116 | | 82 | 337 | | 328 | 101 |
| TOT BIL mg/dl | 0.1 | 0.3 | 0.2 | | 0.2 | 0.1 | | 0.1 | 0.2 |
| AST IU/l | 29 | 32 | 103 | | 55 | 27 | | 25 | 21 |
| LDH IU/l | 520 | 496 | 912 | | 768 | 615 | | 252 | 227 |
| URIC Ac mg/dl | 0.1 | <0.1 | <0.1 | | 0.1 | 0.1 | | <0.1 | 0.1 |

FIG. 31B

CLINICAL LAB RESULTS FROM MONKEY E

| DATE | 11-May | 11-May | 14-May | 18-May | 4-Jun | 18-Jun | 24-Jun | 24-Jun | 12-Jul | 17-Sep |
|---|---|---|---|---|---|---|---|---|---|---|
| WBC/mm3 | 8.7 | F | 7.1 | | 5.3 | 8.6 | 8.6 | S | 6.9 | 8.1 |
| NEUT/mm3 | 4850 | I | 2060 | | 3210 | 4480 | 2040 | E | | 2592 |
| LYMP/mm3 | 3060 | R | 4220 | | 1510 | 3360 | 5610 | C | | 5265 |
| MONO/mm3 | 120 | S | 520 | | 280 | 350 | 460 | O | | 162 |
| EOS/mm3 | 30 | T | 110 | | 150 | 80 | 170 | N | | 81 |
| HEMOG, gr/dl | 12.9 | | 13.5 | | 13.7 | 12.6 | 12.4 | D | 13.8 | 13.9 |
| HEMATOCR. % | 40 | I | 44 | | 42 | 41 | 38 | | 44 | 43 |
| PLAT k/mm3 | 291 | N | 277 | | 287 | 291 | 300 | I | 269 | 432 |
| ESR | 1 | F | 1 | | 1 | 0 | <1 | N | <1 | <1 |
| NA mEq/l | 148 | E | 151 | 147 | | 148 | 149 | F | 148 | 150 |
| K mEq/l | 3 | C | 3.3 | 2.6 | | 3.7 | 3.6 | E | 3.1 | 3.8 |
| Cl mEq/l | 110 | T | 110 | 107 | | 110 | 111 | C | 109 | 110 |
| CO2 mEq/l | 16 | | 25 | 20 | | 22 | 23 | T | 21 | 20 |
| BUN mg/dl | 8 | O | 8 | 11 | | 15 | 13 | I | 14 | 17 |
| CREAT mg/dl | 1.1 | N | 1.2 | 1.2 | | 1.1 | 1 | O | 1 | 1.2 |
| GLUCOSE mg/dl | 115 | | 83 | 102 | | 86 | 65 | N | 87 | 69 |
| ALB gr/dl | 4 | | 4.2 | 4.4 | | 4.5 | 4.8 | | 4 | 4.5 |
| T. PROT., gr/dl | 6.7 | | 7 | 7.1 | | 7 | 7.3 | | 6.8 | 7 |
| CALCIUM mg/dl | 9.3 | | 9.7 | 9.4 | | 9.8 | 9.7 | | 9.7 | 9.4 |
| PO4 mg/dl | 3.5 | | 4.4 | 4.2 | | 5.1 | 3.3 | | 4.6 | 4.1 |
| ALK. PH IU/l | 68 | | 84 | 90 | | 393 | 116 | | 75 | 355 |
| TOT BIL mg/dl | 0.2 | | 0.2 | 0.3 | | 0.1 | 0.2 | | 0.2 | 2 |
| AST IU/l | 32 | | 29 | 47 | | 27 | 28 | | 28 | 24 |
| LDH IU/l | 416 | | 367 | 571 | | 277 | 481 | | 247 | 200 |
| URIC Ac mg/dl | 0.1 | | <0.1 | <0.1 | | 0.1 | 0.1 | | <0.1 | <0.1 |

CYTOLOGY: MONKEY C

| DATE | 5/11/93 | 5/11/93 | 5/18/93 | 6/4/93 | 6/18/93 | 6/24/93 | 6/24/93 | 6/28/93 | 9/17/93 |
|---|---|---|---|---|---|---|---|---|---|
| LEFT NOSTRIL | | FIRST | | | | | SECOND | BIOPSY | |
| Sq. Epith. | 68 | F | 78 | 63 | 72 | 74 | S | B | 69 |
| Resp. Epith. | 30 | I | 18 | 34 | 24 | 25 | E | – | 30 |
| Neutrophils | 1 | R | 2 | 3 | 2 | 0 | C | O | 0 |
| Lymphocytes | 1 | S | 2 | 0 | 1 | 1 | O | P | 0 |
| Eosinophils | 0 | T | 0 | 0 | 1 | 0 | N | S | 1 |
|  |  |  |  |  |  |  | D | Y |  |

FIG. 32B

CYTOLOGY: MONKEY D

| DATE | 5/11/93 | 5/11/93 | 5/18/93 | 6/4/93 | 6/18/93 | 6/24/93 | 6/24/93 | 7/5/93 | 9/17/93 |
|---|---|---|---|---|---|---|---|---|---|
| LEFT NOSTRIL | | FIRST | | | | | SECOND | BIOPSY | |
| Sq. Epith. | 60 | F | 60 | 72 | 72 | 84 | S | B | 73 |
| Resp. Epith. | 39 | I | 39 | 26 | 25 | 14 | E | – | 25 |
| Neutrophils | 1 | R | 1 | 0 | 1 | 2 | C | O | 2 |
| Lymphocytes | 0 | S | 2 | 2 | 1 | 0 | O | P | 0 |
| Eosinophils | 0 | T | 0 | 0 | 1 | 0 | N | S | 0 |
|  |  |  |  |  |  |  | D | Y |  |

CYTOLOGY: MONKEY E

| DATE | 5/11/93 | 5/11/93 | 5/18/93 | 6/4/93 | 6/18/93 | 6/24/93 | 6/24/93 | 7/12/93 | 9/17/93 |
|---|---|---|---|---|---|---|---|---|---|
| LEFT NOSTRIL | | | | | | | | | |
| Sq. Epith. | 60 | FIRST | 60 | 72 | 72 | 84 | SECOND | BIOPSY | 73 |
| Resp. Epith. | 39 | | 39 | 26 | 25 | 14 | | | 25 |
| Neutrophils | 1 | | 1 | 0 | 1 | 2 | | | 2 |
| Lymphocytes | 0 | | 2 | 2 | 1 | 0 | | | 0 |
| Eosinophils | 0 | | 0 | 0 | 1 | 0 | | | 0 |

FIG. 32C

ADENOVIRAL VECTORS FOR GENE THERAPY CONTAINING DELETIONS IN THE ADENOVIRAL GENOME

RELATED APPLICATIONS

This is a continuation application(s) Ser. No. 08/136,742 filed on Oct. 13, 1993, now U.S. Pat. No. 5,670,488, which is a continuation-in-part of application U.S. Ser. No. 07/985,478 filed Dec. 3, 1992, now abandoned.

BACKGROUND OF THE INVENTION

Cystic Fibrosis (CF) is the most common fatal genetic disease in humans (Boat, T. F. et al. in The Metabolic Basis of Inherited Diseases (Scriver, C. R. et al. eds., McGraw-Hill, N.Y. (1989)). Approximately one in every 2,500 infants in the United States is born with the disease. At the present time, there are approximately 30,000 CF patients in the United States. Despite current standard therapy, the median age of survival is only 26 years. Disease of the pulmonary airways is the major cause of morbidity and is responsible for 95% of the mortality. The first manifestation of lung disease is often a cough, followed by progressive dyspnea. Tenacious sputum becomes purulent because of colonization of Staphylococcus and then with Pseudomonas. Chronic bronchitis and bronchiectasis can be partially treated with current therapy, but the course is punctuated by increasingly frequent exacerbations of the pulmonary disease. As the disease progresses, the patient's activity is progressively limited. End-stage lung disease is heralded by increasing hypoxemia, pulmonary hypertension, and cor pulmonale.

The upper airways of the nose and sinuses are also involved by CF. Most patients with CF develop chronic sinusitis. Nasal polyps occur in 15–20% of patients and are common by the second decade of life. Gastrointestinal problems are also frequent in CF; infants may suffer meconium ileus. Exocrine pancreatic insufficiency, which produces symptoms of malabsorption, is present in the large majority of patients with CF. Males are almost uniformly infertile and fertility is decreased in females.

Based on both genetic and molecular analyses, a gene associated with CF was isolated as part of 21 individual cDNA clones and its protein product predicted (Kerem, B. S. et al. (1989) Science 245:1073–1080; Riordan, J. R. et al. (1989) Science 245:1066–1073; Rommens, J. M. et al. (1989) Science 245:1059–1065)). U.S. Ser. No. 07/488,307 describes the construction of the gene into a continuous strand, expression of the gene as a functional protein and confirmation that mutations of the gene are responsible for CF. (See also Gregory, R. J. et al. (1990) Nature 347:382–386; Rich, D. P. et al. (1990) Nature 347:358–362). The co-pending patent application also discloses experiments which show that proteins expressed from wild type but not a mutant version of the cDNA complemented the defect in the cAMP regulated chloride channel shown previously to be characteristic of CF.

The protein product of the CF associated gene is called the cystic fibrosis transmembrane conductance regulator (CFTR) (Riordan, J. R. et al. (1989) Science 245:1066–1073). CFTR is a protein of approximately 1480 amino acids made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) or P-glycoprotein, bovine adenyl cyclase, the yeast STE6 protein as well as several bacterial amino acid transport proteins (Riordan, J. R. et al. (1989) Science 245:1066–1073; Hyde, S. C. et al. (1990) Nature 346:362–365). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan, J. R. et al. (1989) Science 245:1066–1073; Welsh, 1986; Frizzell, R. A. et al. (1986) Science 233:558–560; Welsh, M. J. and Liedtke, C. M. (1986) Nature 322:467; Li, M. et al. (1988) Nature 331:358–360; Hwang, T-C. et al. (1989) Science 244:1351–1353).

Sequence analysis of the CFTR gene of CF chromosomes has revealed a variety of mutations (Cutting, G. R. et al. (1990) Nature 346:366–369; Dean, M. et al. (1990) Cell 61:863–870; and Kerem, B-S. et al. (1989) Science 245:1073–1080; Kerem, B-S. et al. (1990) Proc. Natl. Acad, Sci. USA 87:8447–8451). Population studies have indicated that the most common CF mutation, a deletion of the 3 nucleotides that encode phenylalanine at position 508 of the CFTR amino acid sequence (AF508), is associated with approximately 70% of the cases of cystic fibrosis. This mutation results in the failure of an epithelial cell chloride channel to respond to cAMP (Frizzell R. A. et al. (1986) Science 233:558–560; Welsh, M. J. (1986) Science 232:1648–1650.; Li, M. et al. (1988) Nature 331:358–360; Quinton, P. M. (1989) Clin. Chem. 35:726–730). In airway cells, this leads to an imbalance in ion and fluid transport. It is widely believed that this causes abnormal mucus secretion, and ultimately results in pulmonary infection and epithelial cell damage.

Studies on the biosynthesis (Cheng, S. H. et al. (1990) Cell 63:827–834; Gregory, R. J. et al. (1991) Mol. Cell Biol. 11:3886–3893) and localization (Denning, G. M. et al. (1992) J. Cell Biol. 118:551–559 ) of CFTR AF508, as well as other CFTR mutants, indicate that many CFTR mutant proteins are not processed correctly and, as a result, are not delivered to the plasma membrane (Gregory, R. J. et al. (1991) Mol. Cell Biol. 11:3886–3893). These conclusions are consistent with earlier functional studies which failed to detect cAMP-stimulated Cl$^-$ channels in cells expressing CFTR AF508 (Rich, D. P. et al. (1990) Nature 347:358–363; Anderson, M. P. et al. (1991) Science 251:679–682).

To date, the primary objectives of treatment for CF have been to control infection, promote mucus clearance, and improve nutrition (Boat, T. F. et al. in The Metabolic Basis of Inherited Diseases (Scriver, C. R. et al. eds., McGraw-Hill, New York (1989)). Intensive antibiotic use and a program of postural drainage with chest percussion are the mainstays of therapy. However, as the disease progresses, frequent hospitalizations are required. Nutritional regimens include pancreatic enzymes and fat-soluble vitamins. Bronchodilators are used at times. Corticosteroids have been used to reduce inflammation, but they may produce significant adverse effects and their benefits are not certain. In extreme cases, lung transplantation is sometimes attempted (Marshall, S. et al. (1990) Chest 98:1488).

Most efforts to develop new therapies for CF have focused on the pulmonary complications. Because CF mucus consists of a high concentration of DNA, derived from lysed neutrophils, one approach has been to develop recombinant human DNase (Shak, S. et al. (1990) Proc. Natl. Sci. Acad USA 87:9188). Preliminary reports suggest that aerosolized enzyme may be effective in reducing the viscosity of mucus.

This could be helpful in clearing the airways of obstruction and perhaps in reducing infections. In an attempt to limit damage caused by anexcess of neutrophil derived elastase, protease inhibitors have been tested. For example, alpha-1-antitrypsin purified from human plasma has been aerosolized to deliver enzyme activity to lungs of CF patients (McElvaney, N. et al. (1991) *The Lancet* 337:392). Another approach would be the use of agents to inhibit the action of oxidants derived from neutrophils. Although biochemical parameters have been successfully measured, the long term beneficial effects of these treatments have not been established.

Using a different rationale, other investigators have attempted to use pharmacological agents to reverse the abnormally decreased chloride secretion and increased sodium absorption in CF airways. Defective electrolyte transport by airway epithelial is thought to alter the composition of the respiratory secretions and mucus (Boat, T. F. et al. in The Metabolic Basis of Inherited Diseases (Scriver, C. R. et al. eds., McGraw-Hill, New York (1989); Quinton, P. M. (1990) *FASEB J* 4:2709–2717). Hence, pharmacological treatments aimed at correcting the abnormalities in electrolyte transport could be beneficial. Trials are in progress with aerosolized versions of the drug amiloride; amiloride is a diuretic that inhibits sodium channels, thereby inhibiting sodium absorption Initial results indicate that the drug, is safe and suggest a slight change in the rate of disease progression, as measured by lung function tests (Knowles, M. et al. (1990) *N. Eng. J Med.* 322: 1189–1194; App, E.(1990)*Am. Rev. Respir. Dis.* 141:605. Nucleotides, such as ATP or UTP, stimulate purinergic receptors in the airway epithelium. As a result, they open a class of chloride channel that is different from CFTR chloride channels. In vitro studies indicate that ATP and UTP can stimulate chloride secretion (Knowles. M. et al. (1991) *N. Eng. J. Med.* 325:533). Preliminary trails to test the ability of nucleotides to stimulate secretion in vivo, and thereby correct the electrolyte transport abnormalities are underway.

Despite progress in therapy, cystic fibrosis remains a lethal disease, and no current therapy treats the basic defect. However, two general approaches may prove feasible. These are: 1) protein replacement therapy to deliver the wild type protein to patients to augment their defective protein, and; 2) gene replacement therapy to deliver wild type copies of the CF associated gene. Since the most life threatening manifestations of CF involve pulmonary complications, epithelial cells of the upper airways are appropriate target cells for therapy.

The feasibility of gene therapy has been established by introducing a wild type cDNA into epithelial cells from a CF patient and demonstrating complementation of the hallmark defect in chloride ion transport (Rich, D. P. et al. (1990) *Nature* 347:358–363 ). This initial work involved cells in tissue culture, however, subsequent work has shown that to deliver the gene to the airways of whole animals, defective adenoviruses may be useful (Rosenfeld, (1992) *Cell* 68:143–155. However, the safety and effectiveness of using defective adenoviruses remain to be demonstrated.

SUMMARY OF THE INVENTION

In general, the instant invention relates to vectors for transferring selected genetic material of interest (e.g., DNA or RNA) to cells in vivo. In preferred embodiments, the vectors are adenovirus-based. Advantages of adenovirus-based vectors for gene therapy are that they appear to be relatively safe and can be manipulated to encode the desired gene product and at the same time are inactivated in terms of their ability to replicate in a normal lytic viral life cycle. Additionally, adenovirus has a natural tropism for airway epithelia. Therefore, adenovirus-based vectors are particularly preferred for respiratory gene therapy applications such as gene therapy for cystic fibrosis.

In one embodiment, the adenovirus-based gene therapy vector comprises an adenovirus 2 serotype genome in which the E1a and E1b regions of the genome, which are involved in early stages of viral replication have been deleted and replaced by genetic material of interest (e.g., DNA encoding the cystic fibrosis transmembrane regulator protein).

In another embodiment, the adenovirus-based therapy vector is a pseudo-adenovirus (PAV). PAVs contain no potentially harmful viral genes, have a theoretical capacity for foreign material of nearly 36 kb, may be produced in reasonably high titers and maintain the tropism of the parent adenovirus for dividing and non-dividing human target cell types. PAVs comprise adenovirus inverted terminal repeats and the minimal sequences of a wild-type adenovirus type 2 genome necessary for efficient replication and packaging by a helper virus and genetic material of interest. In a preferred embodiment, the PAV contains adenovirus 2 sequences.

In a further embodiment, the adenovirus-based gene therapy vector contains the open readin frame 6 (ORE6) of adenovira ear region 4 (E4) from the E4 promoter and is deleted for all other E4 open reading frames. Optionally, this vector can include deletions in the E1 and/or E3 regions. Alternatively, the adenovirus-based gene therapy vector contains the open reading frame 3 (ORF3) of adenoviral E4 from the E4 promoter and is deleted for all other E4 open reading frames. Again, optionally, this vector can include deletions in the E1 and/or E3 regions. The deletion of non-essential open reading frames of E4 increases the cloning capacity by approximately 2 kb without significantly reducing the viability of the virus in cell culture. In combination with deletions in the E1 and/or E3 regions of adenovirus vectors, the theoretical insert capacity of the resultant vectors is increased to 8–9 kb.

The invention also relates to methods of gene therapy using the disclosed vectors and genetically engineered cells produced by the method.

BRIEF DESCRIPTION OF THE TABLES AND DRAWINGS

Further understanding of the invention may be had by reference to the tables and figures wherein.

Figure 18A:
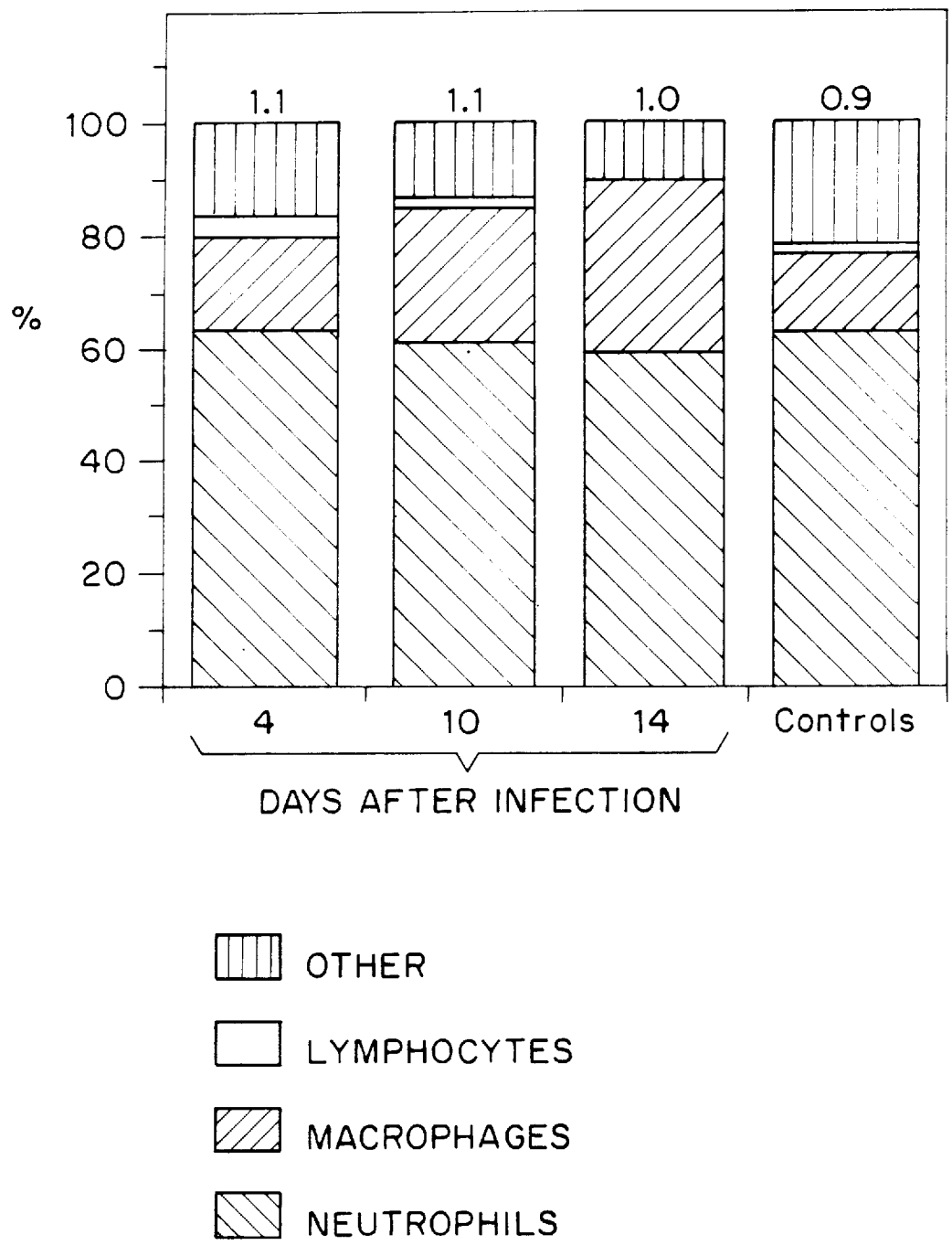
Figure 18B:
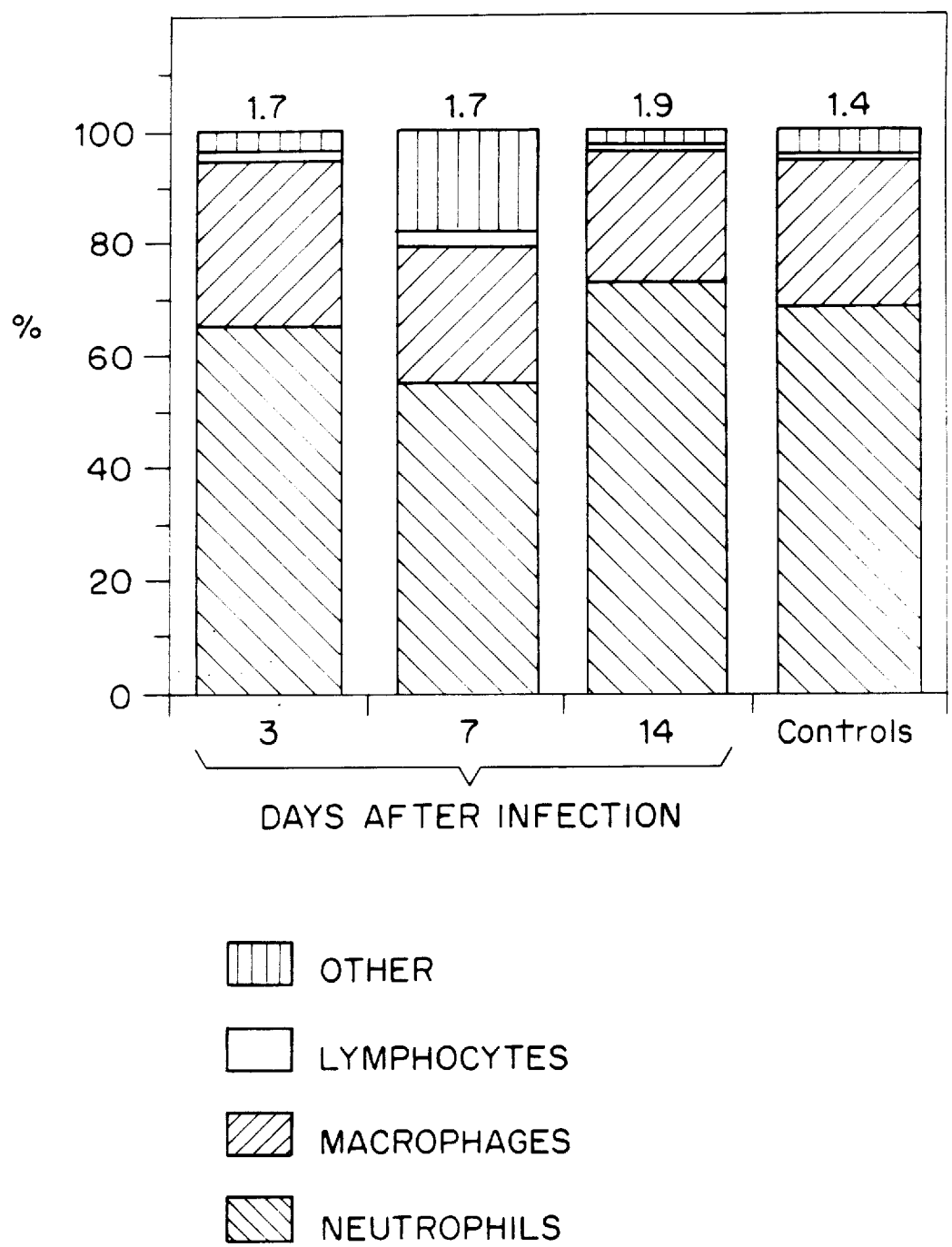

FIGS. 18A and 18B show differential cell analyses of bronchoalveolar lavage specimens from control and infected rats. These data demonstrate that none of the rats treated with Ad2/CFTR-1 had a change in the total or differential white blood cell count 4, 10, and 14 days after infection (FIG. 18A) and 3, 7, 14 days after infection (FIG. 18B).

Figure 19A:
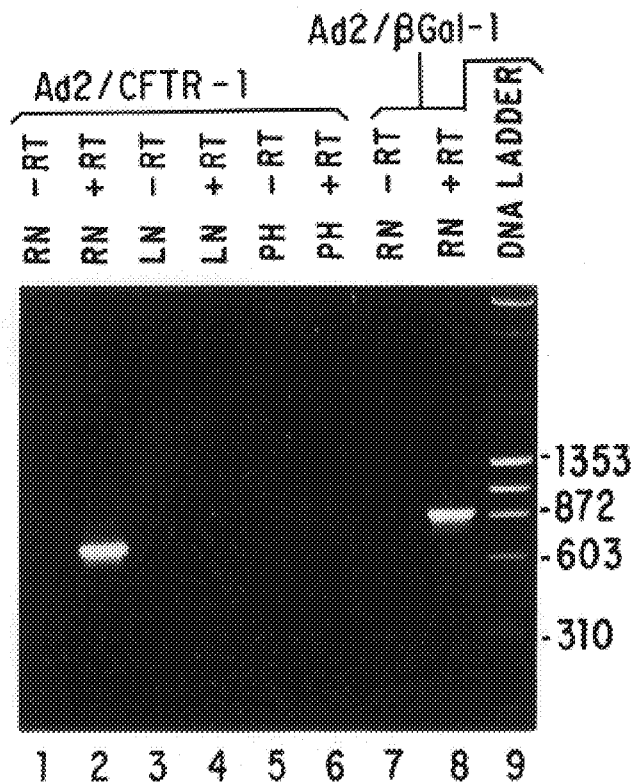
Figure 19B:
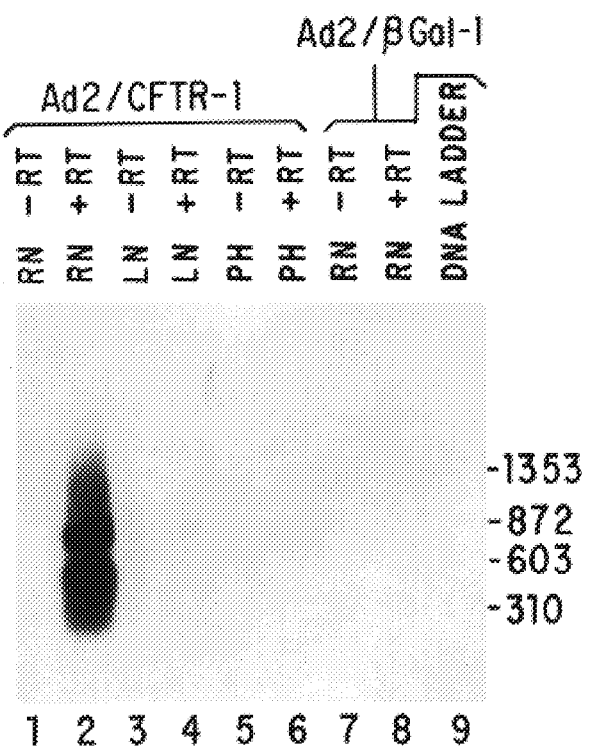
Figure 20A:
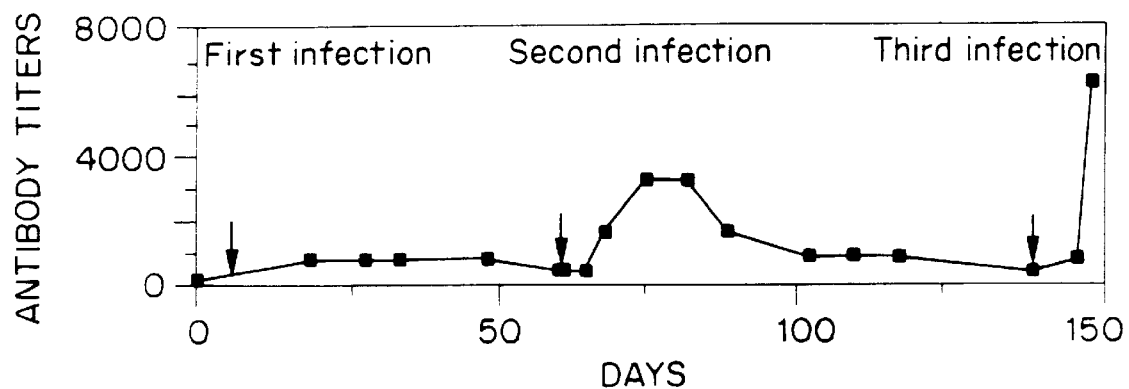
Figure 20B:
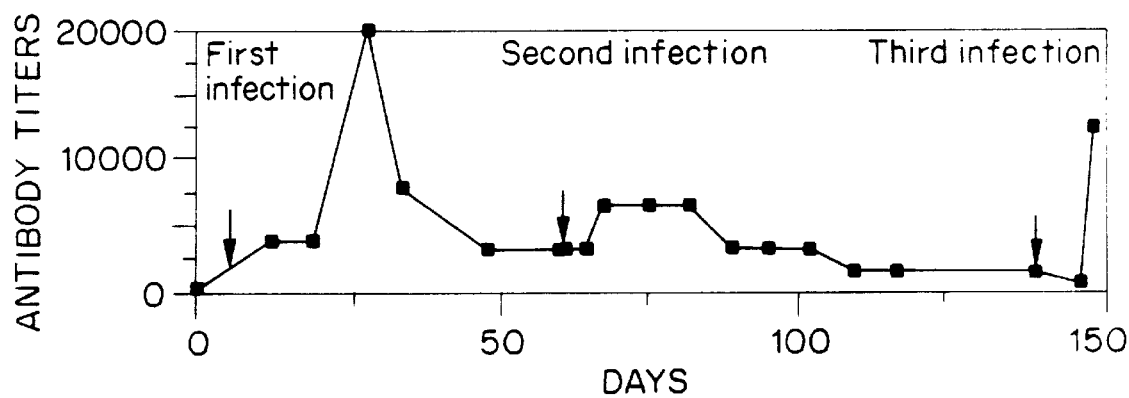
Figure 20C:
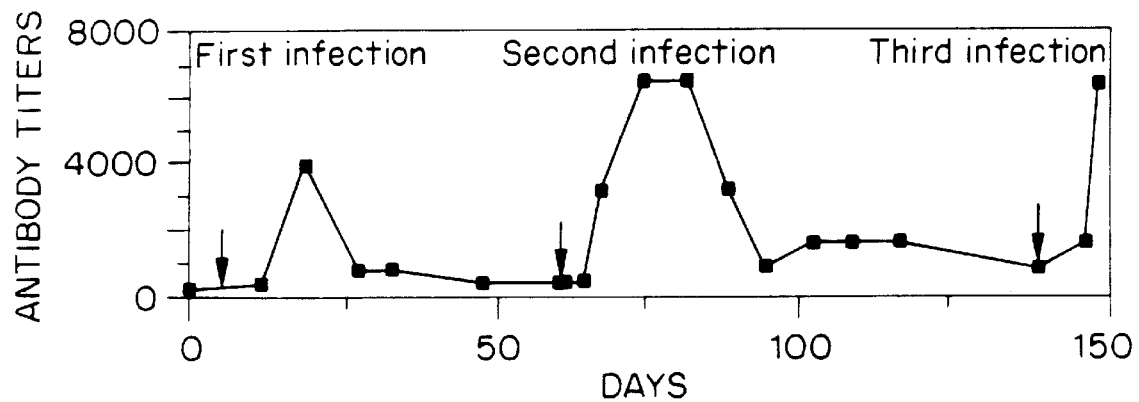
Figure 20D:
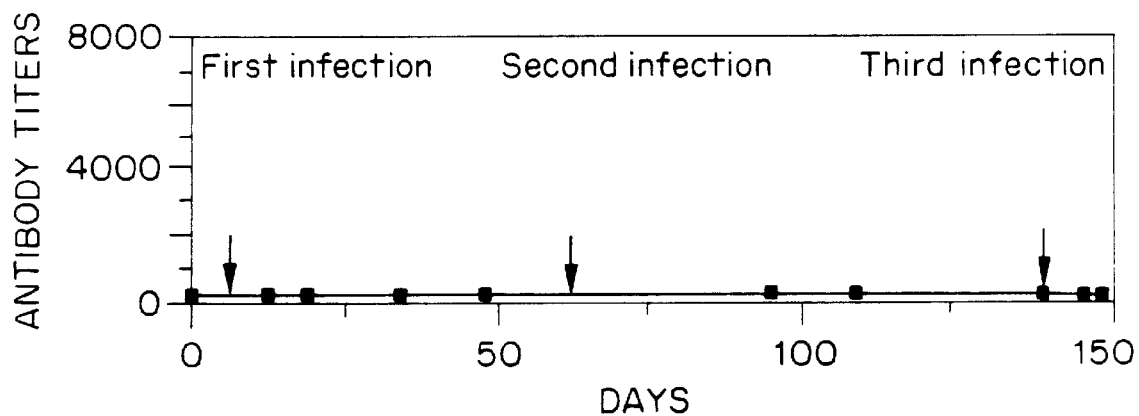

FIGS. 19A and 19B show examples of UV fluorescence from an agarose gel electrophoresis, stained with ethidium bromide, of products of RT-PCR from nasal brushings of Rhesus monkeys after application of Ad2/CFTR-1 or Ad2/β-Gal.

FIGS. 20A–20D show serum antibody titers in Rhesus monkeys after three vector administrations. These graphs demonstrate that all three monkeys treated with Ad2/CFTR-1 developed antibodies against adenovirus.

Figure 21A:
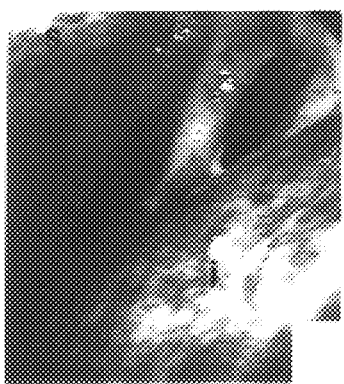
Figure 21D:
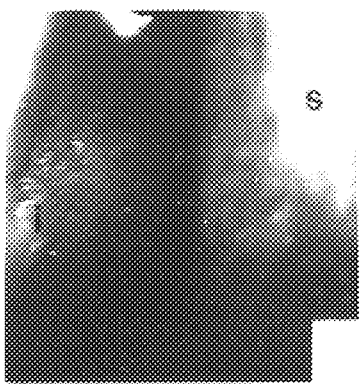
Figure 21G:
Figure 21B:
Figure 21E:
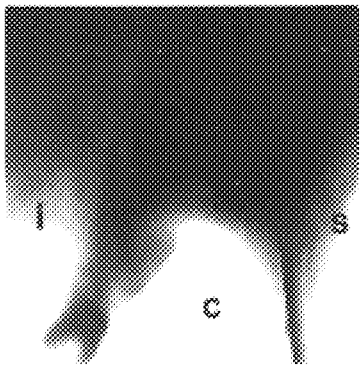
Figure 21H:
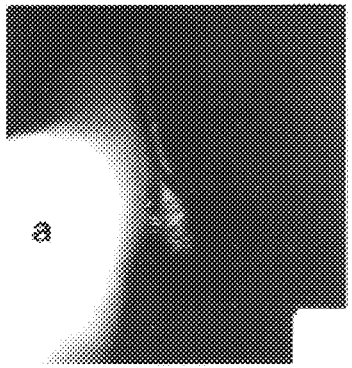
Figure 21C:
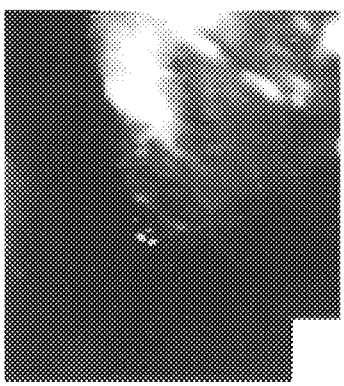
Figure 21F:
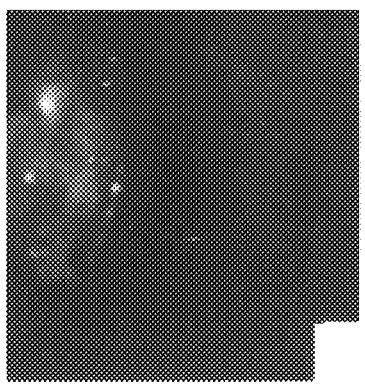
Figure 21I:

FIGS. 21A–21I are photomicrographs of human nasal mucosa immediately before, during, and after Ad2/CFTR-1 application. These photomicrographs demonstrate that inspection of the nasal mucosa showed mild to moderate erythema, edema, and exudate in patients treated with Ad2/CFTR-1 (FIGS. 21A–21C) and in control patients (FIGS. 21G–21I). These changes were probably due to local anesthesia and vasoconstriction because when an additional patient was exposed to Ad2/CFTR-1 in a method which did not require the use of local anesthesia or vasoconstriction, there were no symptoms and the nasal mucosa appeared normal (FIGS. 21 D–21F).

Figure 22:
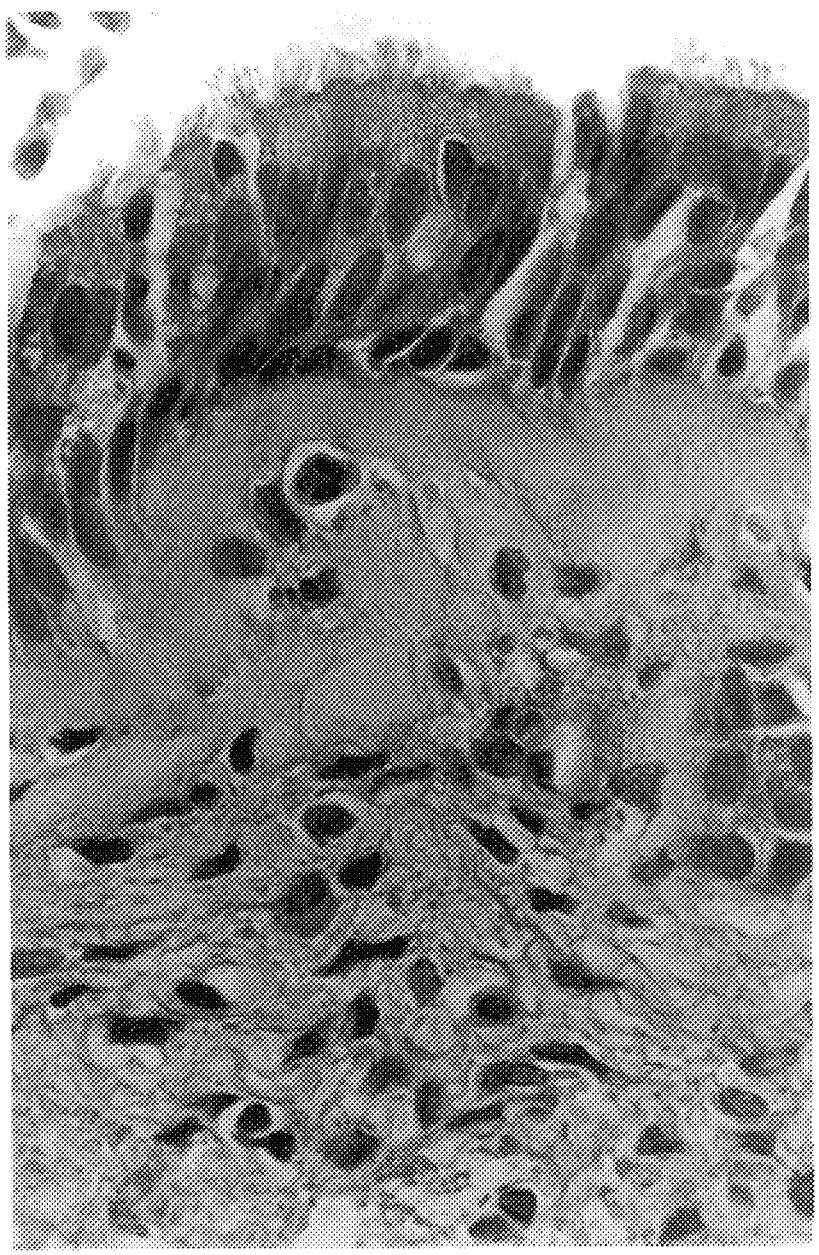

FIG. 22 is a photomicrograph of a hematoxylin and eosin stained biopsy of human nasal mucosa obtained from the third patient three days after Ad2/CFTR-1 administration. This section shows a morphology consistent with CF, i.e., a thickened basement membrane and occasional morphonuclear cells in the submucosa, but no abnormalities that could be attributed to the adenovirus vector.

Figure 23:
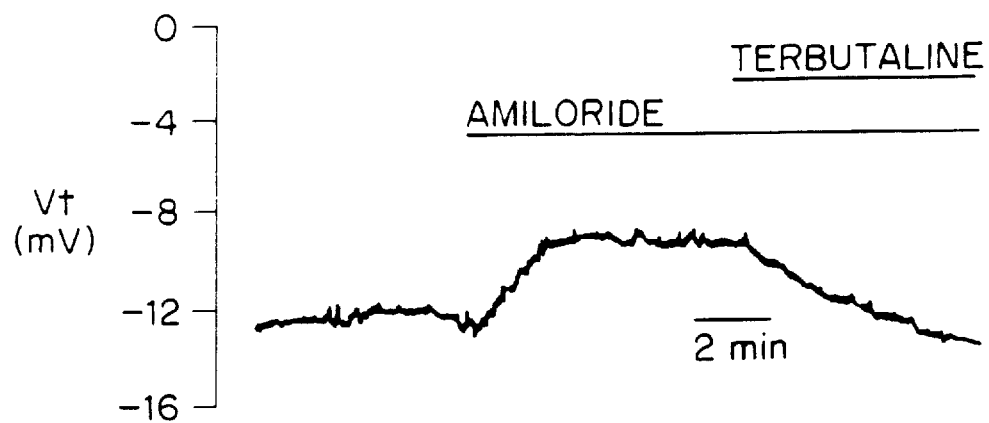

FIG. 23 shows transepithelial voltage (Vt) across the nasal epithelium of a normal human subject. Amiloride ($\mu$M) and terbutaline ($\mu$M) were perfused onto the mucosal surface beginning at the times indicated. Under basal conditions Vt was electrically negative. Perfusion of amiloride onto the mucosal surface inhibited Vt by blocking apical $Na^+$ channels.

Figure 24A:
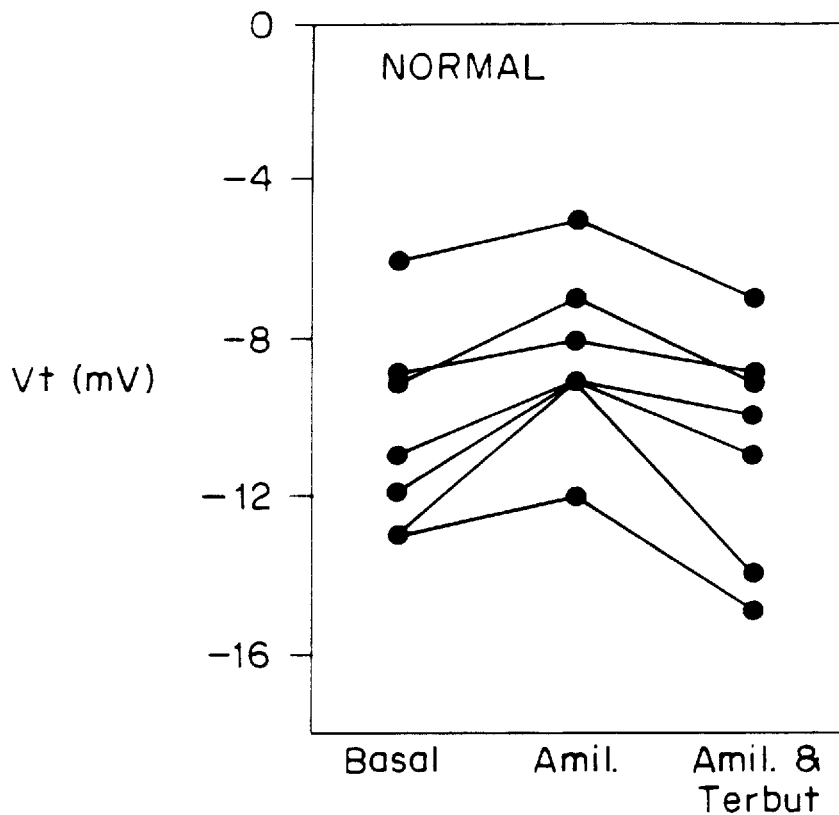
Figure 24B:
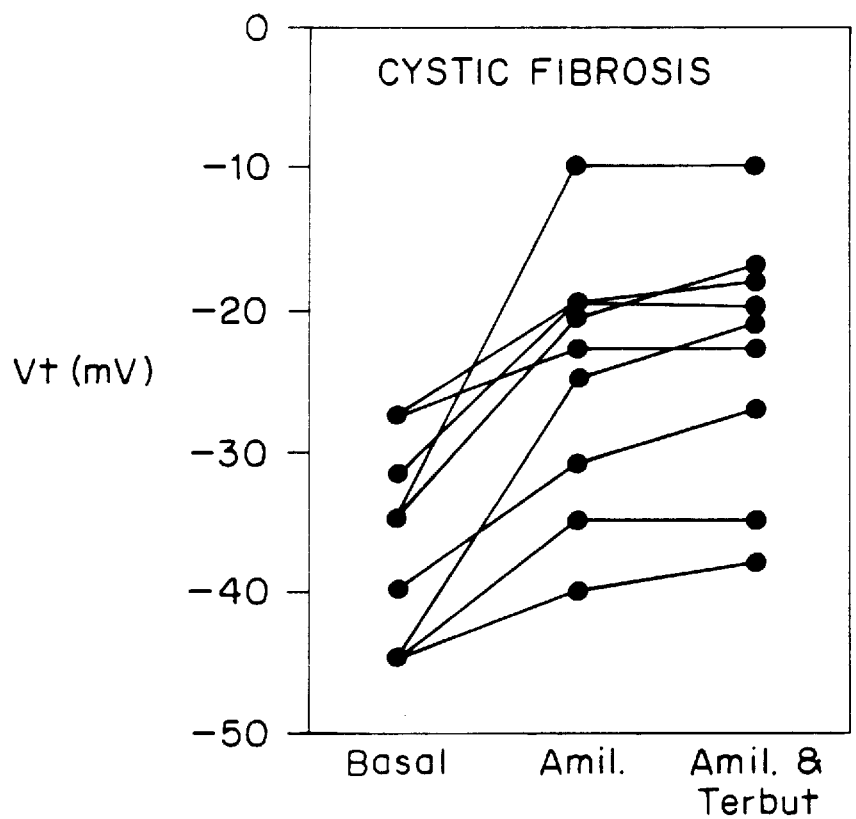

FIGS. 24A and 24B show transepithelial voltage (Vt) across the nasal epithelium of normal human subjects (FIG. 24A) and patients with CF (FIG. 24B). Values were obtained under basal conditions, during perfusion with amiloride ($\mu$M) and during perfusion of amiloride plus terbutaline ($\mu$M) onto the mucosal surface. Data are from seven normal subjects and nine patients with CF. In patients with CF, Vt was more electrically negative than in normal subjects (FIG. 24B). Amiloride inhibited Vt in CF patients, as it did in normal subjects. However, Vt failed to hyperpolarize when terbutaline was perfused onto the epithelium in the presence of amiloride. Instead, Vt either did not change or became less negative, a result very different from that observed in normal subjects.

Figure 25A:
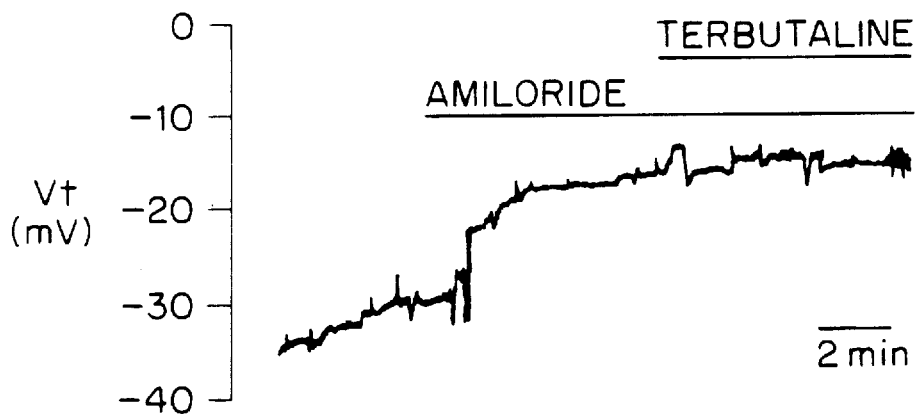
Figure 25B:
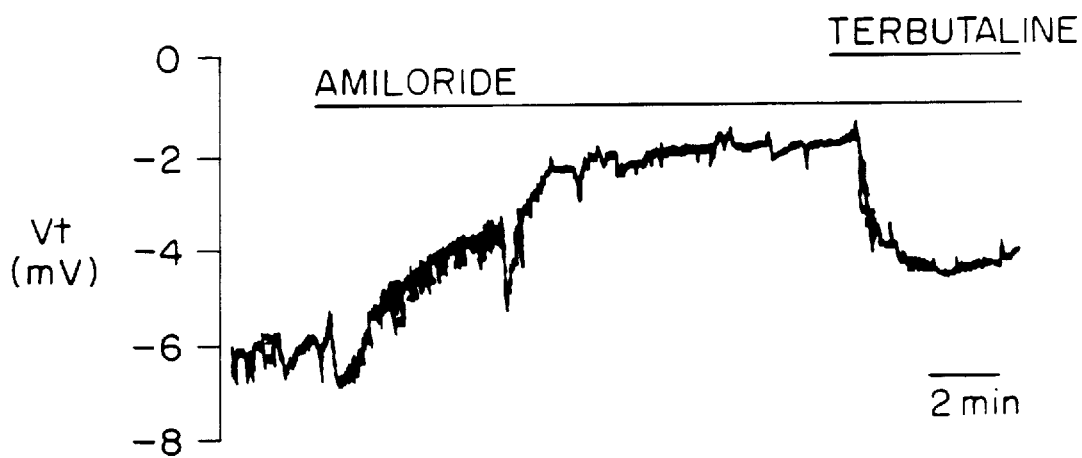

FIGS. 25A and 25B show transepithelial voltage (Vt) across the nasal epithelium of a third patient before (FIG. 25A) and after (FIG. 25B) administration of approximately 25 MOI of Ad2/CFTR-1. Amiloride and terbutaline were perfused onto the mucosal surface beginning at the times indicated. FIG. 25A shows an example from the third patient before treatment. FIG. 25B shows that in contrast to the response before Ad2/CFTR-1 was applied, after virus replication, in the presence of amiloride, terbutaline stimulated Vt.

Figure 26A:
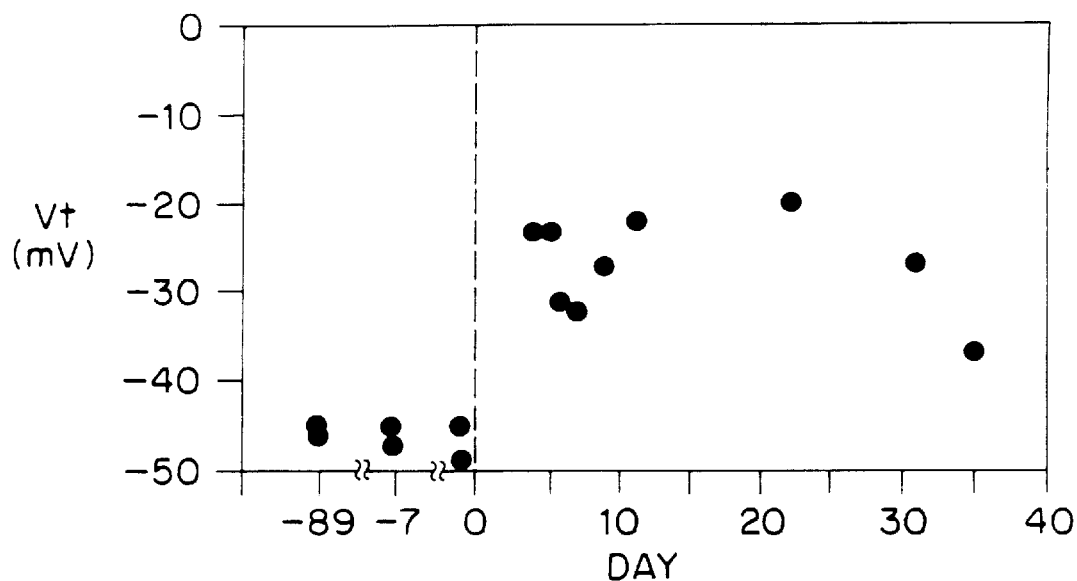
Figure 26B:
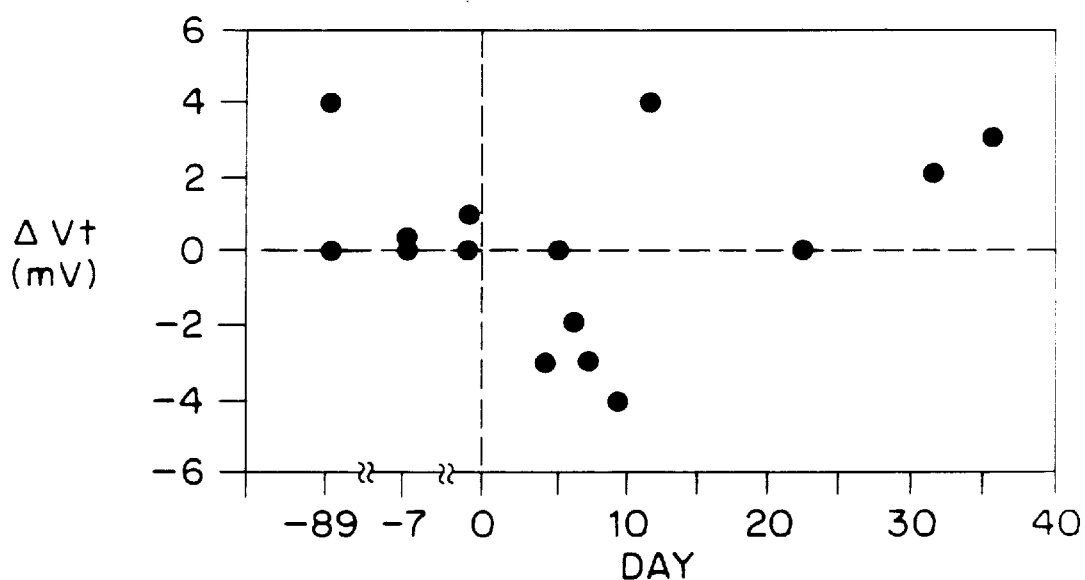
Figure 26C:
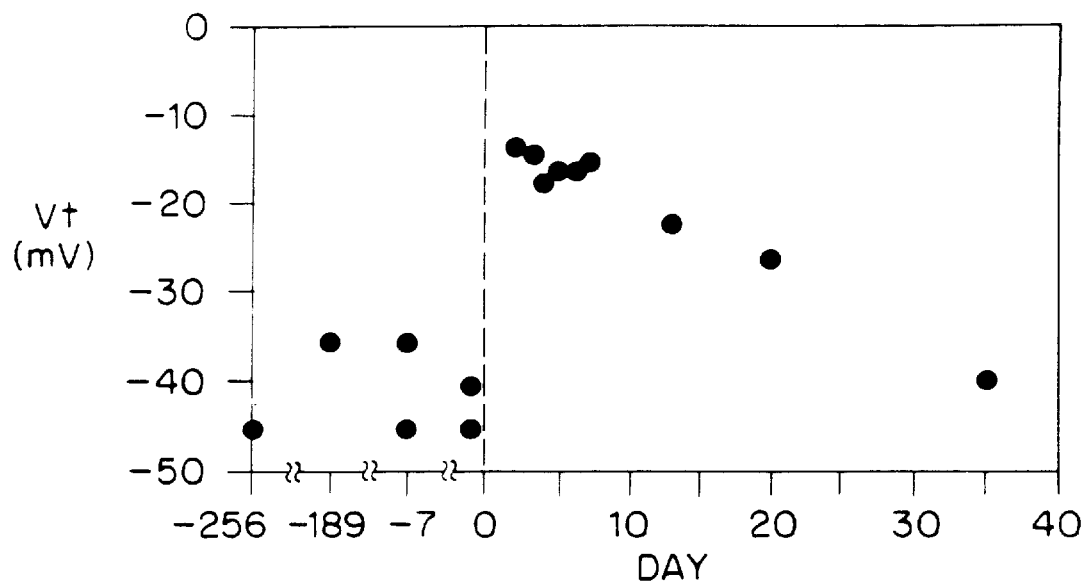
Figure 26D:
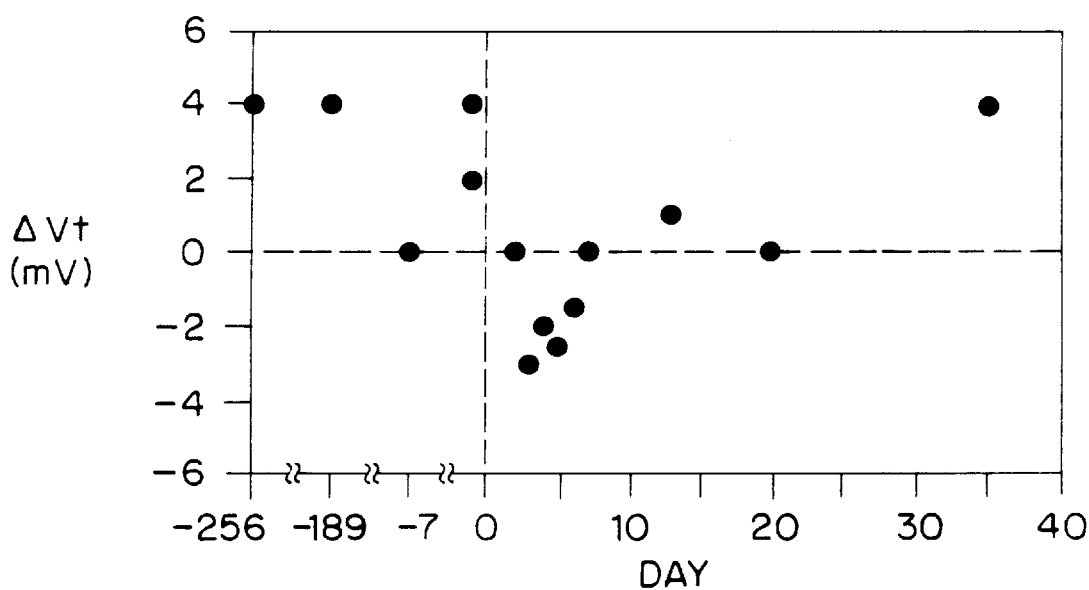
Figure 26E:
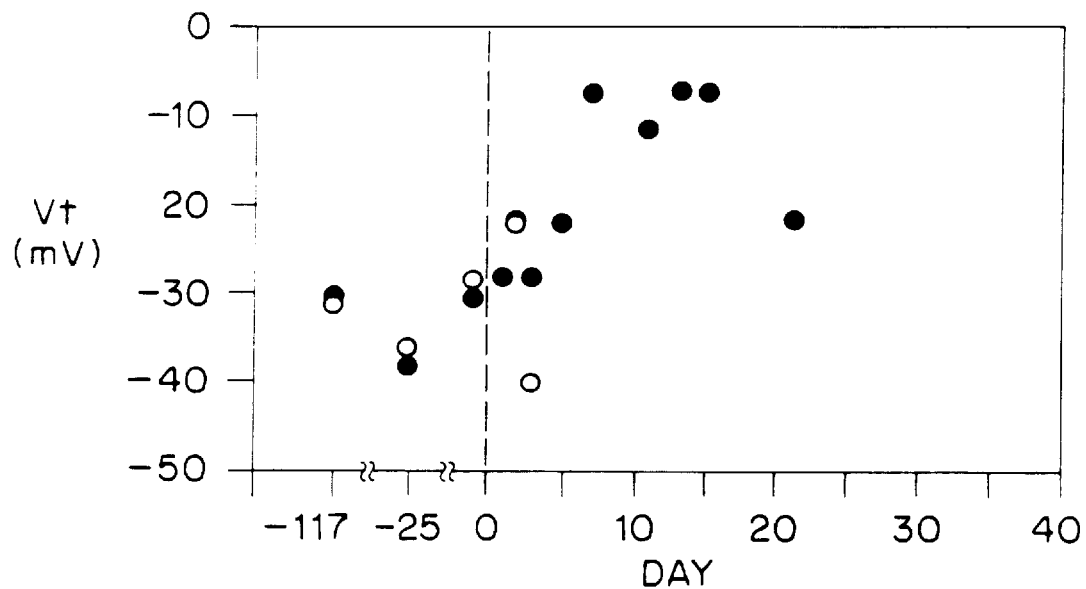
Figure 26F:
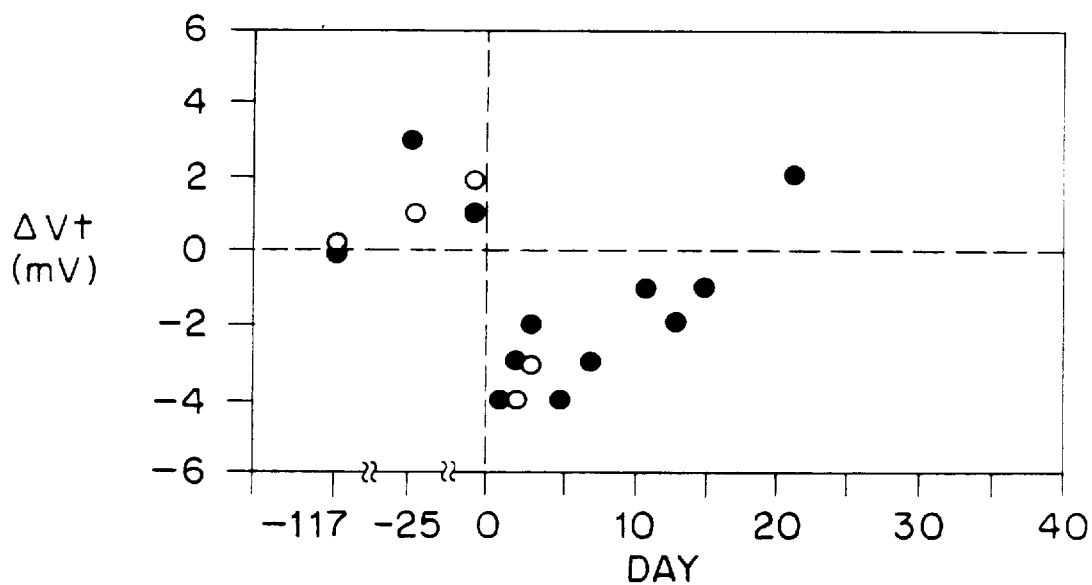

FIGS. 26A–26F show the time of course changes in transepithelial electrical properties before and after administration of Ad2/CFTR-1. FIGS. 26A and 26B are from the first patient who received approximately 1 MOI; FIGS. 26C and 26D are from the second patient who received approximately 3 MOI; and FIGS. 26E and 26F are from the third patient who received approximately 25 MOI. FIGS. 26A, 26C, and 26E show values of basal transepithelial voltage (Vt) and FIGS. 26B, 26D, and 26F show the change in transepithelial voltage (ΔVt) following perfusion of terbutaline in the presence of amiloride. Day zero indicates the day of Ad2/CFTR-1 administration. FIGS. 26A, 26C, and 26E show the time course of changes in basal Vt for all three patients. The decrease in basal Vt suggests that application of Ad2/CFTR-1 corrected the CF electrolyte transport defect in nasal epithelium of all three patients. Additional evidence came from an examination of the response to terbutaline. FIGS. 26B, 26D, and 26F show the time course of the response. These data indicate that Ad2/CFTR-1 corrected the CF defect in Cl$^-$ transport.

Figure 27A:
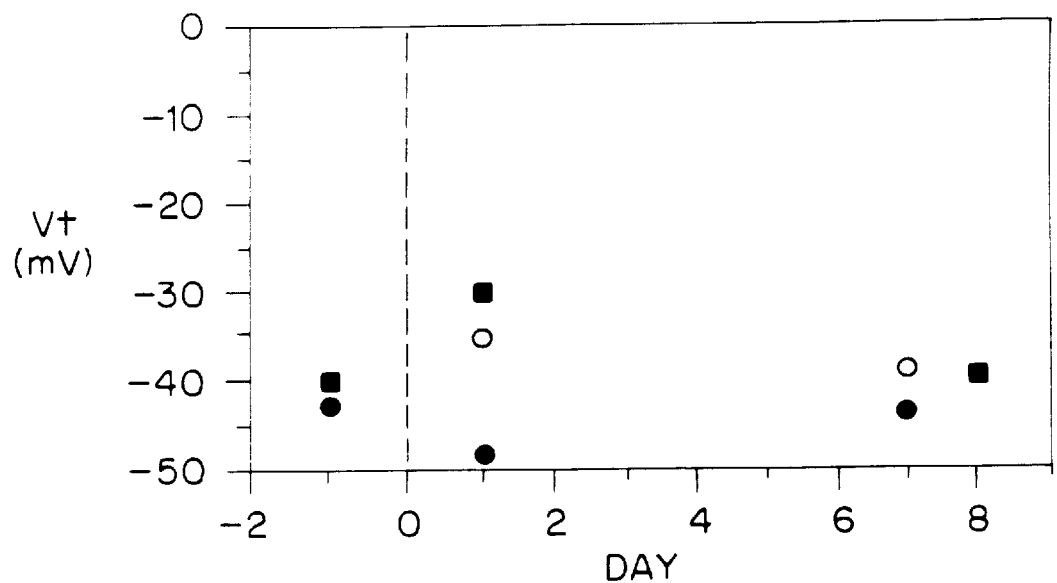
Figure 27B:
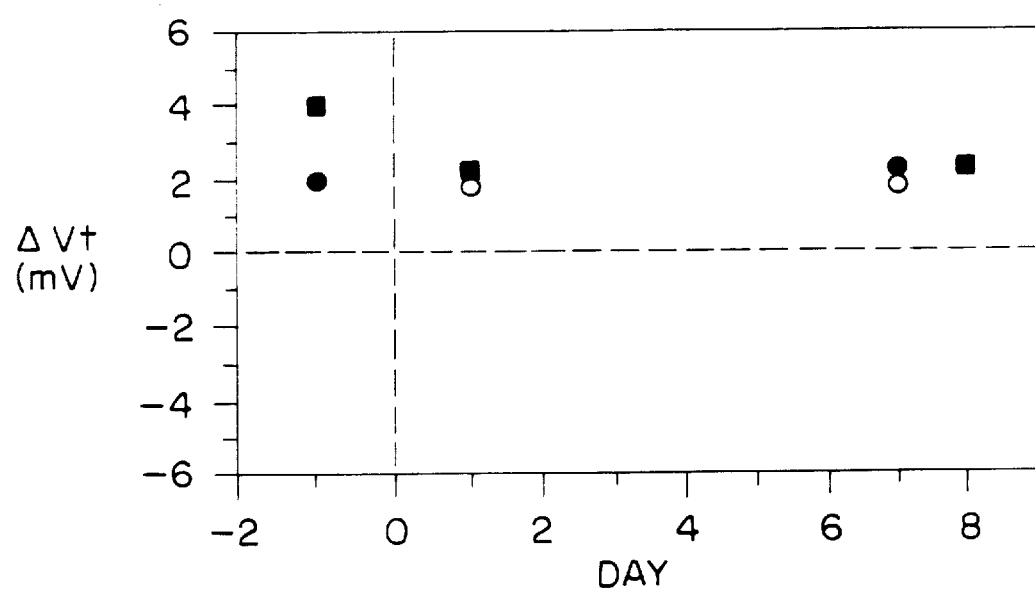

FIGS. 27A and 27B show the time course of changes in transepithelial electrical properties before and after administration of saline instead of Ad2/CFTR-1 to CF patients. Day zero indicates the time of mock administration. The top graph shows basal transepithelial voltage (Vt) and the bottom graph shows the change in transepithelial voltage following perfusion with terbutaline in the presence of amiloride (ΔVt). Closed symbols are data from two patients that received local anesthetic/vasoconstriction and placement of the applicator for thirty minutes. Open symbol is data from a patient that received local anesthetic/vasoconstriction, but not placement of the applicator. Symptomatic changes and physical findings were the same as those observed in CF patients treated with a similar administration procedure and Ad2/CFTR-1.

Figure 28:
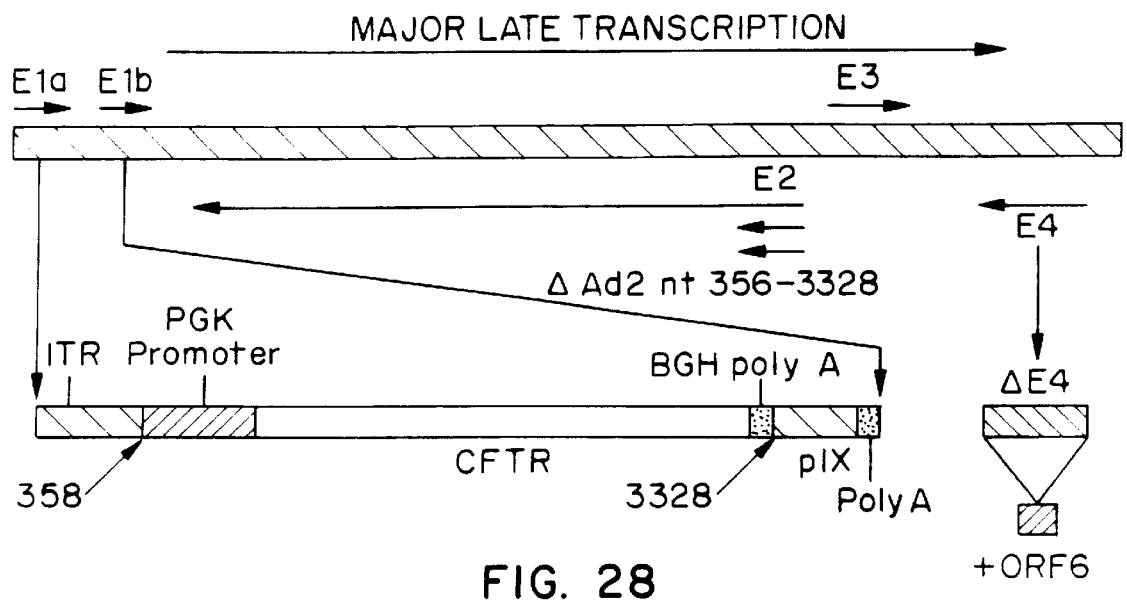

FIG. 28 is a schematic of Ad2-ORF6/PGK-CFTR which differs from Ad2/CFTR-1 in that the latter utilized the endogenous E1a promoter, had no poly A addition signal directly downstream of CFTR and retained an intact E4 region.

Figure 29:
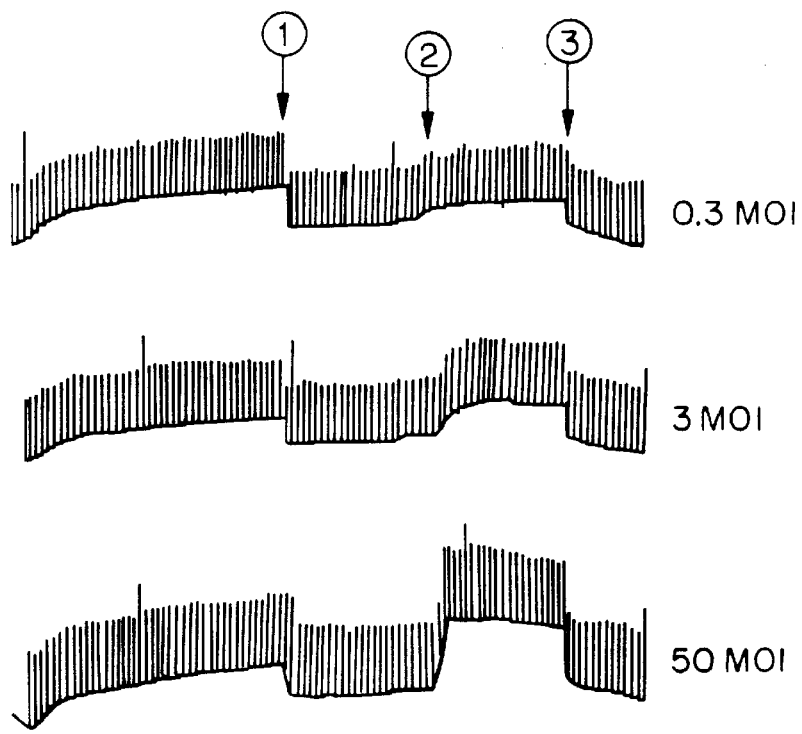

FIG. 29 shows short-circuit currents from CF nasal polyp epithelial cells infected with Ad2-ORF6/PGK-CFTR at multiplicities of 0.3, 3, and 50. At the indicated times: (1) 10 $\mu$M amiloride, (2) cAMP agonists (10 $\mu$M forskolin and 100 $\mu$M IBMX, and (3) 1 mM diphenylamine-2-carboxylate were added to the mucosal solution.

FIGS. 30A–30C show summaries of the clinical signs (or lack thereof) of infection with Ad2-ORF6/PGK-CFTR.

FIGS. 31A–31C show a summary of blood counts, sedimentation rate, and clinical chemistries after infection with Ad2-ORF6/PGK-CFTR for monkeys C, D, and E. There was no evidence of a systemic inflammatory response or other abnormalities of the clinical chemistries.

FIGS. 32A–32C show summaries of white blood cells counts in monkeys C, D, and E after infection with Ad2-ORF6/PGK-CFTR. These data indicate that the administration of Ad2-ORF6/PGK-CFTR caused no change in the distribution and number of inflammatory cells at any of the time points following viral administration.

Figure 33A:
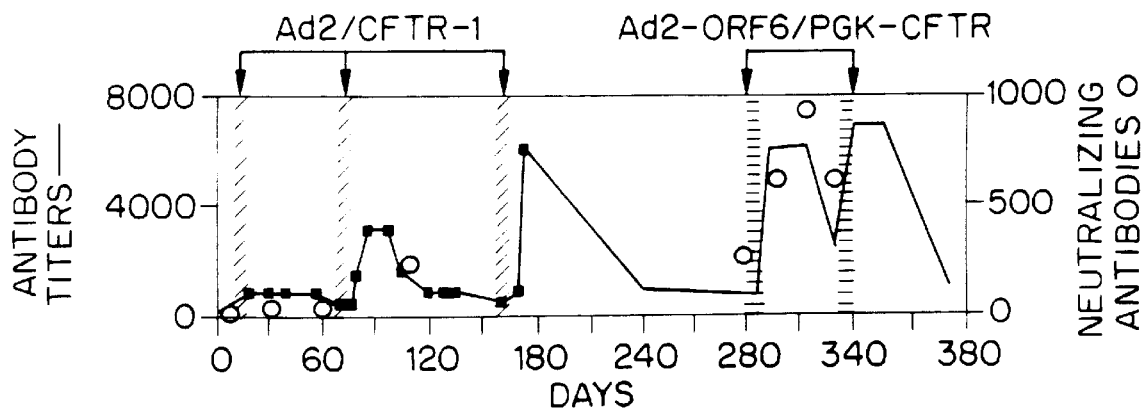
Figure 33B:
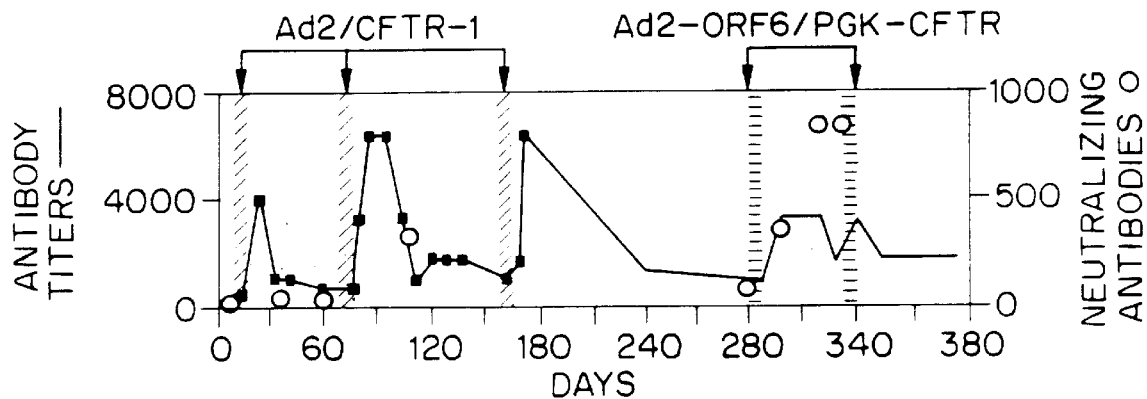
Figure 33C:
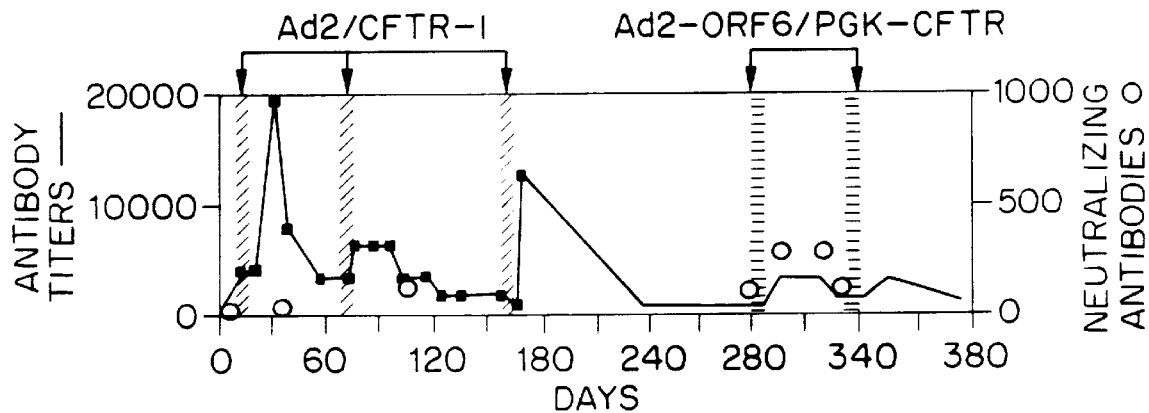

FIGS. 33A–33C show antibody titers to adenovirus prior to and after the first and second administrations of Ad2-ORF6/PGK-CFTR. Prior to administration of Ad2-ORF6/PGK-CFTR, the monkeys had received instillations of Ad2/CFTR- 1. Antibody titers measured by ELISA rose within one week after the first and second administrations of Ad2-ORF6/PGK-CFTR. Serum neutralizing antibodies also rose within a week after viral administration and peaked at day 24. No anti-adenoviral antibodies were detected by ELISA or neutralizing assay in nasal washings of any of the monkeys.

DETAILED DESCRIPTION AND BEST MODE

Gene Therapy

As used herein, the phrase "gene therapy" refers to the transfer of genetic material (e.g., DNA or RNA) of interest into a host to treat or prevent a genetic or acquired disease or condition. The genetic material of interest encodes a product (e.g., a protein polypeptide, peptide or functional RNA) whose production in vivo is desired. For example, the genetic material of interest can encode a hormone, receptor, enzyme or (poly) peptide of therapeutic value. Examples of genetic material of interest include DNA encoding: the cystic fibrosis transmembrane regulator (CFTR), Factor VIII, low density lipoprotein receptor, beta-galactosidase, alpha-galactosidase, beta-glucocerebrosidase, insulin, parathyroid hormone, and alpha-1-antitrypsin.

Although the potential for gene therapy to treat genetic diseases has been appreciated for many years, it is only recently that such approaches have become practical with the treatment of two patients with adenosine deamidase deficiency. The protocol consists of removing lymphocytes from the patients, stimulating them to grow in tissue culture, infecting them with an appropriately engineered retrovirus followed by reintroduction of the cells into the patient (Kantoff, P. et al. (1987) *J Exp. Med* 166:219). Initial results of treatment are very encouraging. With the approval of a number of other human gene therapy protocols for limited clinical use, and with the demonstration of the feasibility of complementing the CF defect by gene transfer, gene therapy for CF appears a very viable option.

The concept of gene replacement therapy for cystic fibrosis is very simple; a preparation of CFTR coding sequences in some suitable vector in a viral or other carrier delivered directly to the airways of CF patients. Since disease of the pulmonary airways is the major cause of morbidity and is responsible for 95% of mortality, airway epithelial cells are preferred target cells for CF gene therapy. The first generation of CF gene therapy is likely to be transient and to require repeated delivery to the airways. Eventually, however, gene therapy may offer a cure for CF when the identity of the precursor or stem cell to air epithelial cells becomes known. If DNA were incorporated into airway stem cells, all subsequent generations of such cells would make authentic CFTR from the integrated sequences and would correct the physiological defect almost irrespective of the biochemical basis of the action of CFTR.

Although simple in concept, scientific and clinical problems face approaches to gene therapy, not least of these being that CF requires an in vivo approach while all gene therapy treatments in humans to date have involved ex vivo treatment of cells taken from the patient followed by reintroduction.

One major obstacle to be overcome before gene therapy becomes a viable treatment approach for CF is the development of appropriate vectors to infect tissue manifesting the disease and deliver the therapeutic CFTR gene. Since viruses have evolved very efficient means to introduce their nucleic acid into cells, many approaches to gene therapy make use of engineered defective viruses. However, the use of viruses in vivo raises safety concerns. Although potentially safer, the use of simple DNA plasmid constructs containing mininal additional DNA, on the other hand, is often very inefficient and can result in transient protein expression.

The integration of introduced DNA into the host chromosome has advantages in that such DNA will be passed to daughter cells. In some circumstances, integrated DNA may also lead to high or more sustained expression. However, integration often, perhaps always, requires cellular DNA replication in order to occur. This is certainly the case with the present generation of retroviruses. This limits the use of such viruses to circumstances where cell division occurs in a high proportion of cells. For cells cultured in vitro, this is seldom a problem, however, the cells of the airway are reported to divide only infrequently (Kawanami, O. et al. (1979) *An. Rev. Respir. Dis.* 120:595). The use of retroviruses in CF will probably require damaging the airways (by agents such as $SO_2$ or $O_3$) to induce cell division. This may prove impracticable in CF patients.

Even if efficient DNA integration could be achieved using viruses, the human genome contains elements involved in the regulation of cellular growth only a small fraction of which are presently identified. By integrating adjacent to an element such as a proto-oncogene or an anti-oncogene, activation or inactivation of that element could occur leading to uncontrolled growth of the altered cell. It is considered likely that several such activation/inactivation steps are usually required in any one cell to induce uncontrolled proliferation (R. A. Weinberg (1989) *Cancer Research* 49:3713 ), which may reduce somewhat the potential risk. On the other hand, insertional mutagenesis leading to tumor formation is certainly known in animals with some nondefective retroviruses (R. A. Weinberg (1989);Payne, G. S. et al. (1982) *Nature* 295:209), and the large numbers of potential integrations occurring during the lifetime of a patient treated repeatedly in vivo with retroviruses must raise concerns on the safety of such a procedure.

In addition to the potential problems associated with viral DNA integration, a number of additional safety issues arise. Many patients may have preexisting antibodies to some of the viruses that are candidates for vectors, for example, adenoviruses. In addition, repeated use of such vectors might induce an immune response. The use of defective viral vectors may alleviate this problem somewhat, because the vectors will not lead to productive viral life cycles generating infected cells, cell lysis or large numbers of progeny viruses.

Other issues associated with the use of viruses are the possibility of recombination with related viruses naturally infecting the treated patient, complementation of the viral defects by simultaneous expression of wild type virus proteins and containment of aerosols of the engineered viruses.

Gene therapy approaches to CF will face many of the same clinical challenges at protein therapy. These include the inaccessibility of airway epithelium caused by mucus build-up and the hostile nature of the environment in CF airways which amy inactivate viruses/vectors. Elements of the vector carriers may be immunogenic and introduction of the DNA may be inefficient. These problems, as with protein therapy, are exacerbated by the absence of good animal model for the disease nor a simple clinical end point to measure the efficacy of treatment CF Gene Therapy Vectors—Possible Options Retroviruses—Although defective retroviruses are the best characterized system and so far the only one approved for use in human gene therapy (Miller, A. D. (1990) *Blood* 76:271), the major issue in relation to CF is the requirement for dividing cells to achieve DNA integration and gene expression. Were conditions found to induce airway cell division, the in vivo application of retroviruses, especially if repeated over many years, would necessitate assessment of the safety aspects of insertional mutagenesis in this context.

Adeno-Associated Virus—(AAV) is a naturally occurring defective virus that requires other viruses such as adenoviruses or herpes viruses as helper viruses(Muzyczka, N. (1992) in *Current Topics in Microbiology and Immunology* 158:97). It is also one of the few viruses that may integrate its DNA into non-dividing cells, although this is not yet certain. Vectors containing as little as 300 base pairs of AAV can be packaged and can integrate, but space for exogenous DNA is limited to about 4.5 kb. CFTR DNA may be towards the upper limit of packaging. Furthermore, the packaging process itself is presently inefficient and safety issues such as immunogenecity, complementation and containment will also apply to AAV. Nevertheless, this system is sufficiently promising to warrant further study.

Plasmid DNA—Naked plasmid can be introduced into muscle cells by injection into the tissue. Expression can extend over many months but the number of positive cells is low (Wolff, J. et al. (1989) *Science* 247:1465). Cationic lipids aid introduction of DNA into some cells in culture (Felgner, P. and Ringold, G. M. (1989) *Nature* 337:387). Injection of cationic lipid plasmid DNA complexes into the circulation of mice has been shown to result in expression of the DNA in lung (Brigham, K. et al. (1989) *Am. J Med. Sci.* 298:278). Instillation of cationic lipid plasmid DNA into lung also leads to expression in epithelial cells but the efficiency of expression is relatively low and transient (Hazinski, T. A. et al. (1991) *Am. J Respir., Cell Mol. Biol.* 4:206). One advantage of the use of plasmid DNA is that it can be introduced into non-replicating cells. However, the use of plasmid DNA in the CF airway environment, which already contains high concentrations of endogenous DNA may be problematic.

Receptor Mediated Entry—In an effort to improve the efficiency of plasmid DNA uptake, attempts have been made to utilize receptor-mediated endocytosis as an entry mechanisms and to protect DNA in complexes with polylysine (Wu, G. and Wu, C. H. (1988) *J. Biol. Chem.* 263:14621). One potential problem with this approach is that the incoming plasmid DNA enters the pathway leading from endosome to lysosome, where much incoming material is degraded. One solution to this problem is the use of transferrin DNA-polylysine complexes linked to adenovirus capsids (Curiel, D. T. et al. (1991) *Proc. Natl. Acad Sci. USA* 88:8850). The latter enter efficiently but have the added advantage of naturally disrupting the endosome thereby avoiding shuttling to the lysosome. This approach has promise but at present is relatively transient and suffers from the same potential problems of immunogenicity as other adenovirus based methods.

Adenovirus—Defective adenoviruses at present appear to be a promising approach to CF gene therapy (Berkner, K. L. (1988) *BioTechniques* 6:616). Adenovirus can be manipulated such that it encodes and expresses the desired gene product, (e.g., CFTR), and at the same time is inactivated in terms of its ability to replicate in a normal lytic viral life cycle. In addition, adenovirus has a natural tropism for airway epithelial. The viruses are able to infect quiescent cells as are found in the airways, offering a major advantage over retroviruses. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) *Am. Rev. Respir. Dis.* 109:233–238). Finally, adenovirus mediated gene transfer has been demonstrated in a number of instances including transfer of alpha-1-antitrypsin and CFTR to the lungs of cotton rats (Rosenfeld, M. A. et al. (1991) *Science* 252:431434; Rosenfeld et al., (1992) *Cell* 68:143–155). Furthermore, extensive studies to attempt to establish adenovirus as a causative agent in human cancer were uniformly negative (Green, M. et al. (1979) *Proc. Natl. Acad. Sci.* USA 76:6606).

The following properties would be desirable in the design of an adenovirus vector to transfer the gene for CFTR to the airway cells of a CF patient. The vector should allow sufficient expression of the CFTR, while producing minimal viral gene expression. There should be minimal viral DNA replication and ideally no virus replication. Finally, recombination to produce new viral sequences and complementation to allow growth of the defective virus in the patient should be minimized. A first generation adenovirus vector encoding CFTR (Ad2/CFTR), made as described in the following Example 7, achieves most of these goals and was used in the human trials described in Example 10.

Figure 14:
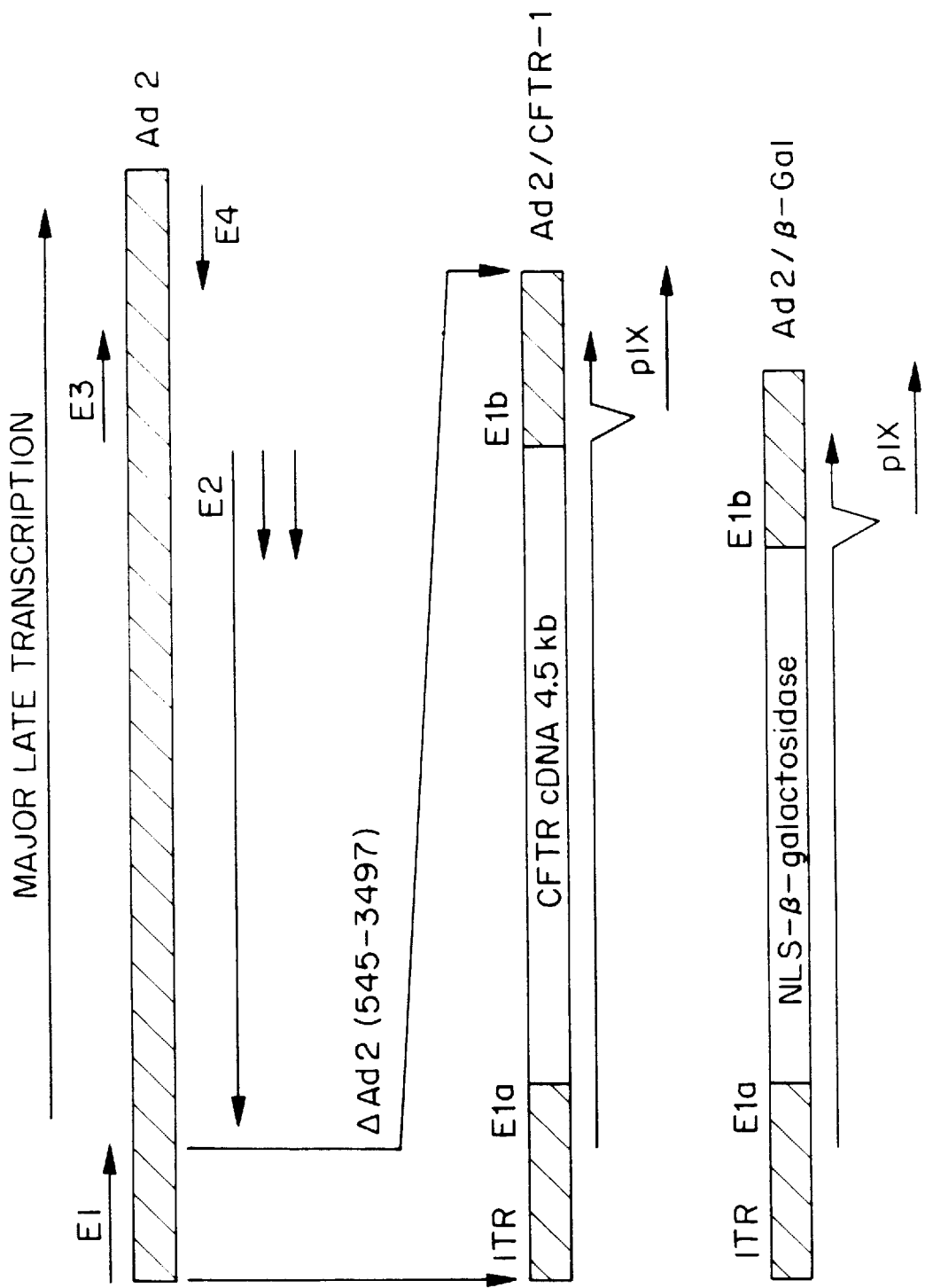
FIG. 14 shows a map of the first generation adenovirus based vector encoding CFTR (Ad2/CFTR-1).
Figure 15:
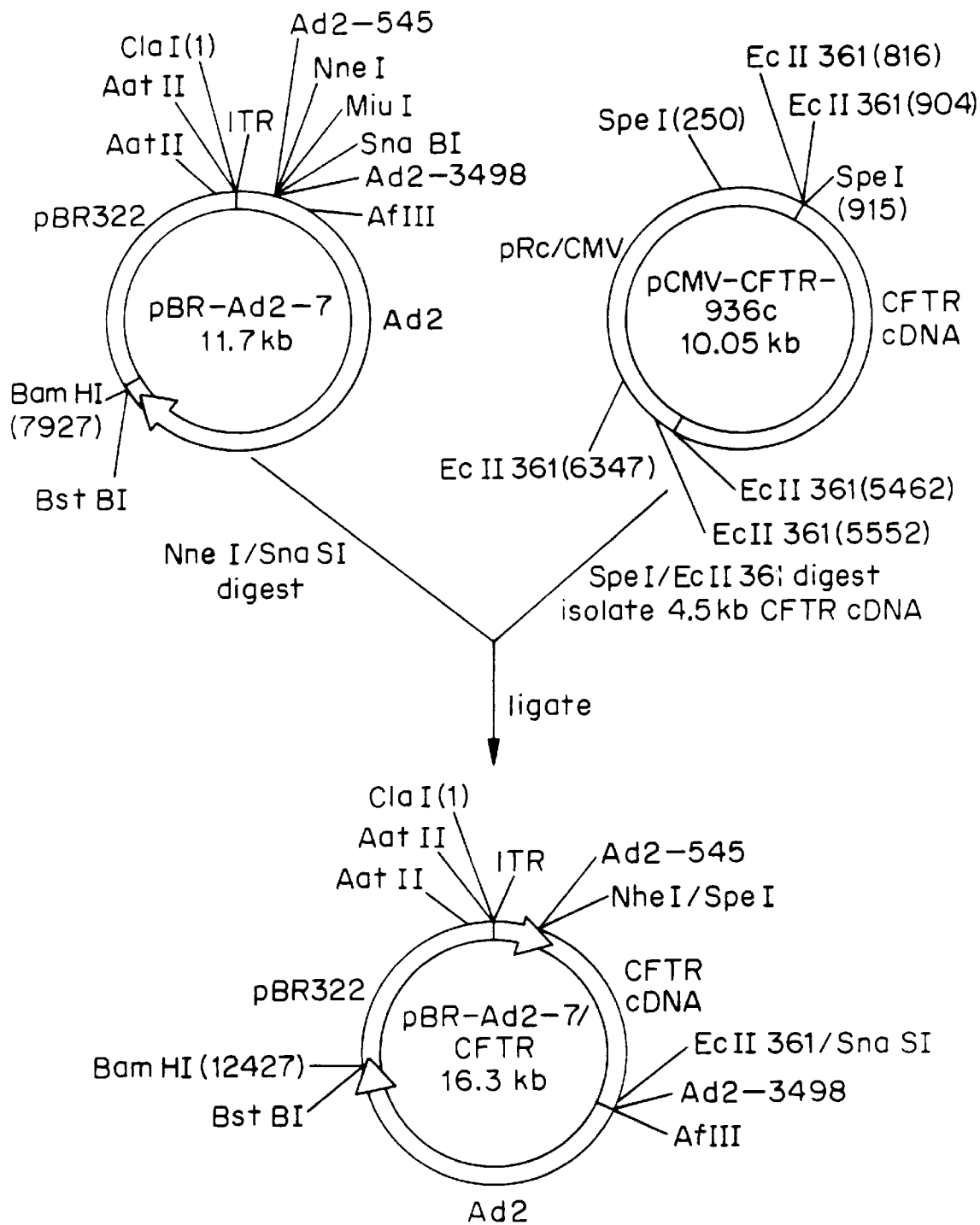
FIG. 15 shows the plasmid construction of the Ad2/CFTR-1 vector.
Figure 16A:
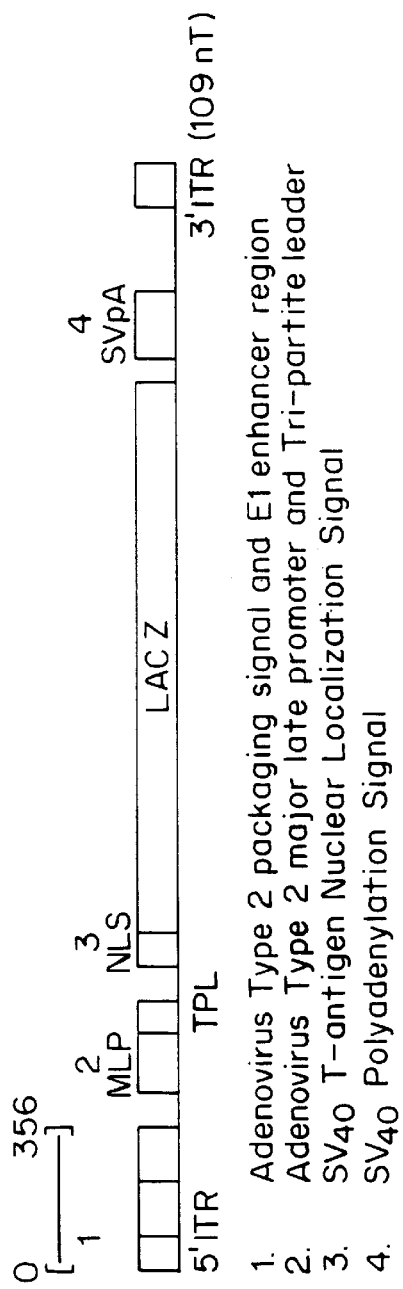
FIGS. 16A and 16B show a map of the second generation adenovirus based vector, PAV.
Figure 16A:
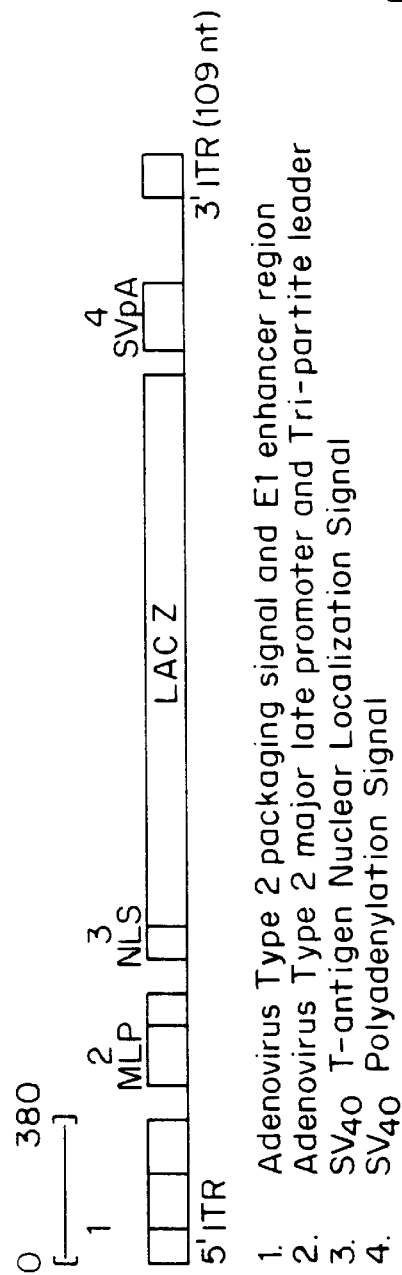
Figure 16A:
Figure 16B:
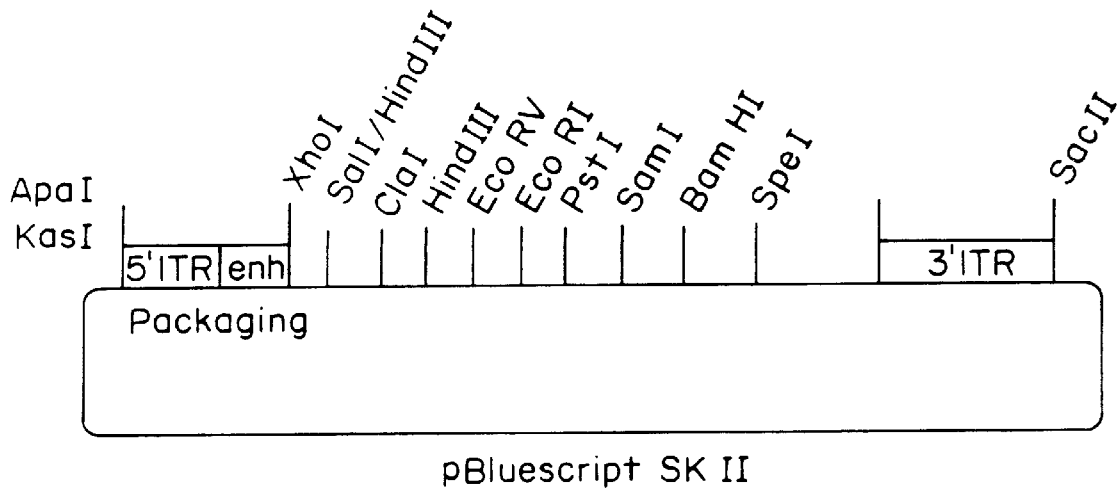
Figure 16B:
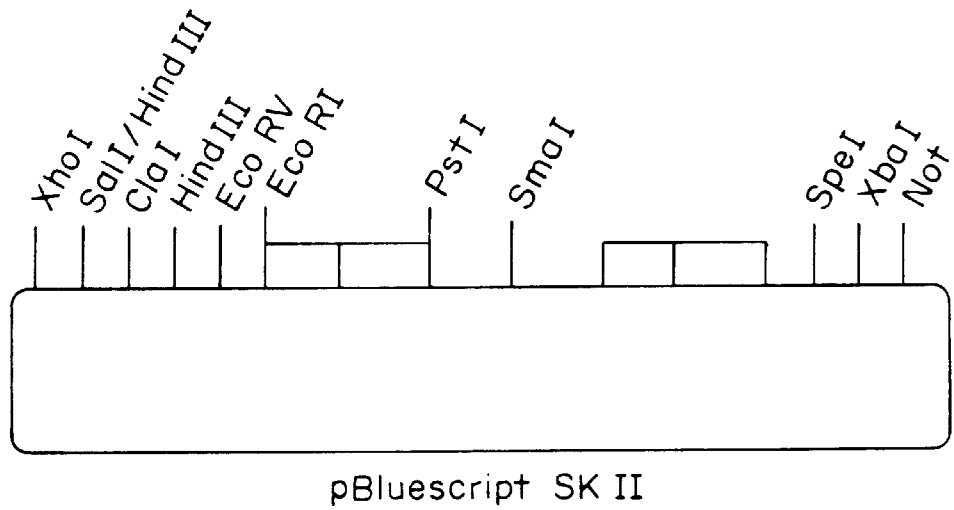

FIG. 14 shows a map of Ad2/CFR-1. As can be seen from the figure, this first generation virus includes viral DNA derived from the common relatively benign adenovirus 2 serotype. The E1a and E1b regions of the viral genome, which are involved in early stages of viral replication have been deleted. Their removal impairs viral gene expression and viral replication. The protein products of these genes also have immortalizing and transforming function in some non-permissive cells.

The CFTR coding sequence is inserted into the viral genome in place of the E1a/E1b region and transcription of the CFTR sequence is driven by the endogenous E1a promoter. This is a moderately strong promoter that is functional in a variety of cells. In contrast to some adenovirus vectors (Rosenfeld, M. et al. (1992) *Cell* 68:143), this adenovirus retains the E3 viral coding region. As a consequence of the inclusion of E3, the length of the adenovirus-CFTR DNA is greater than that of the wild-type adenovirus. The greater length of the recombinant viral DNA renders it more difficult to package. This means that the growth of the Ad2/CFTR virus is impaired even in permissive cells that provide the missing E1a and E1b functions.

The E3 region of the Ad2/CFTR-1 encodes a variety of proteins. One of these proteins, gp19, is believed to interact with and prevent presentation of class 1 proteins of the major histocompatability complex (MHC) (Gooding, C. R. and Wold, W. S. M. (1990) *Crit. Rev. Immunol.* 10:53). This property prevents recognition of the infected cells and thus may allow viral latency. The presence of E3 sequences, therefore, has two useful attributes; first, the large size of the viral DNA renders it doubly defective for replication (i.e., it lacks early functions and is packaged poorly) and second, the absence of MHC presentation could be useful in later applications of Ad2/CFTR-1 in gene therapy involving multiple administrations because it may avoid an immune response to recombinant virus containing cells.

Not only are there advantages associated with the presence of E3; there may be disadvantages associated with its absence. Studies of E3 deleted virus in animals have suggested that they result in a more severe pathology (Gingsberg, H. S. et al. (1989) *Proc. Natl. Acad. Sci.* (USA) 86:3823). Furthermore, E3 deleted virus, such as might be obtained by recombination of an E1 plus E3 deleted virus with wild-type virus, is reported to outgrow wild-type in tissue culture (Barkner, K. L. and Sharp, P. (1983) *Nucleic Acids Research* 11:6003). By contrast, however, a recent report of an E3 replacement vector encoding hepatitis B surface antigen, suggests that when delivered as a live enteric vaccine, such a virus replicates poorly in human compared to wild-type.

The adenovirus vector (Ad2/CFTR-1) and a related virus encoding the marker β-galactosidase (Ad2/β-gal) have been constructed and grown in human 293 cells. These cells contain the E1 region of adenovirus and constitutively express E1a and E1b, which complement the defective adenoviruses by providing the products of the genes deleted from the vector. Because the size of its genome is greater than that of wild-type virus, Ad2/CFTR is relatively difficult to produce.

The Ad2/CFTR-1 virus has been shown to encode CFTR by demonstrating the presence of the protein in 293 cells. The Ad2/β-gal virus was shown to produce its protein in a variety of cell lines grown in tissue culture including a monkey bronchiolar cell line (4MBR-5), primary hamster tracheal epithelial cells, human HeLa, human CF PAC cells (see Example 8) and airway epithelial cells from CF patients (Rich, O. et al. (1990) *Nature* 347:358).

Ad2/CFTR-1 is constructed from adenovirus 2 (Ad2) DNA sequences. Other varieties of adenovirus (e.g., Ad3, Ad5, and Ad7) may also prove useful as gene therapy vectors. This may prove essential if immune response against a single serotype reduces the effectiveness of the therapy.

Second Generation Adenoviral Vectors

Adenoviral vectors currently in use retain most ($\geq 80\%$) of the parental viral genetic material leaving their safety untested and in doubt Second-generation vector systems containing minimal adenoviral regulatory, packaging and replication sequences have therefore been developed.

Pseudo-Adenovirus Vectors (PAV)-PAVs contain adenovirus inverted terminal repeats and the minimal adenovirus 5' sequences required for helper virus dependent replication and packaging of the vector. These vectors contain no potentially harmful viral genes, have a theoretical capacity for foreign material of nearly 36 kb, may be produced in reasonably high titers and maintain the tropism of the parent virus for dividing and non-dividing human target cell types.

The PAV vector can be maintained as either a plasmid-borne construct or as an infectious viral particle. As a plasmid construct, PAV is composed of the minimal sequences from wild type adenovirus type 2 necessary for efficient replication and packaging of these sequences and any desired additional exogenous genetic material, by either a wild-type or defective helper virus.

Figure 17A:
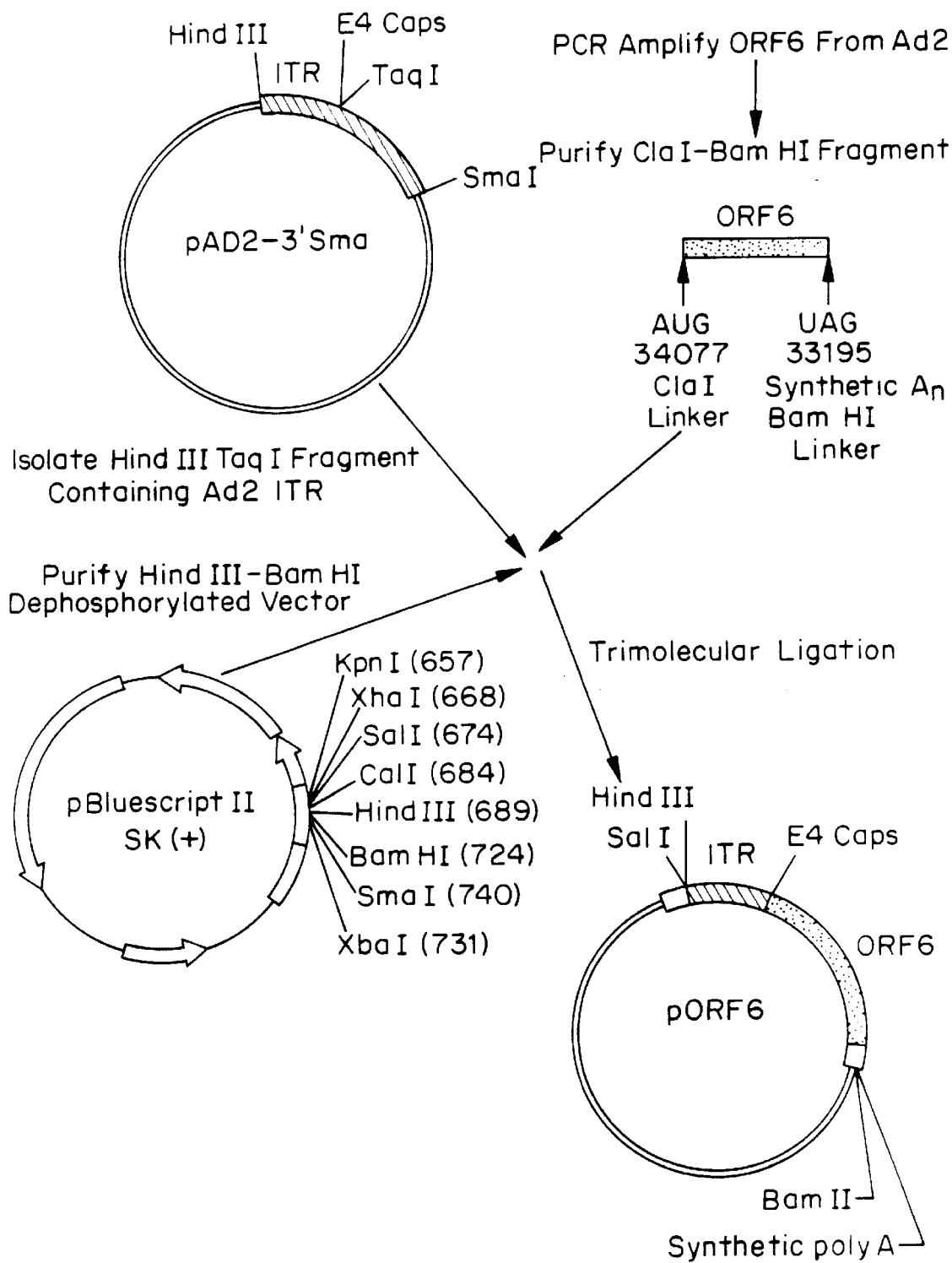
FIGS. 17A and 17B show the plasmid construction for a second generation adenoviral vector (Ad2E40RF6).
Figure 17B:
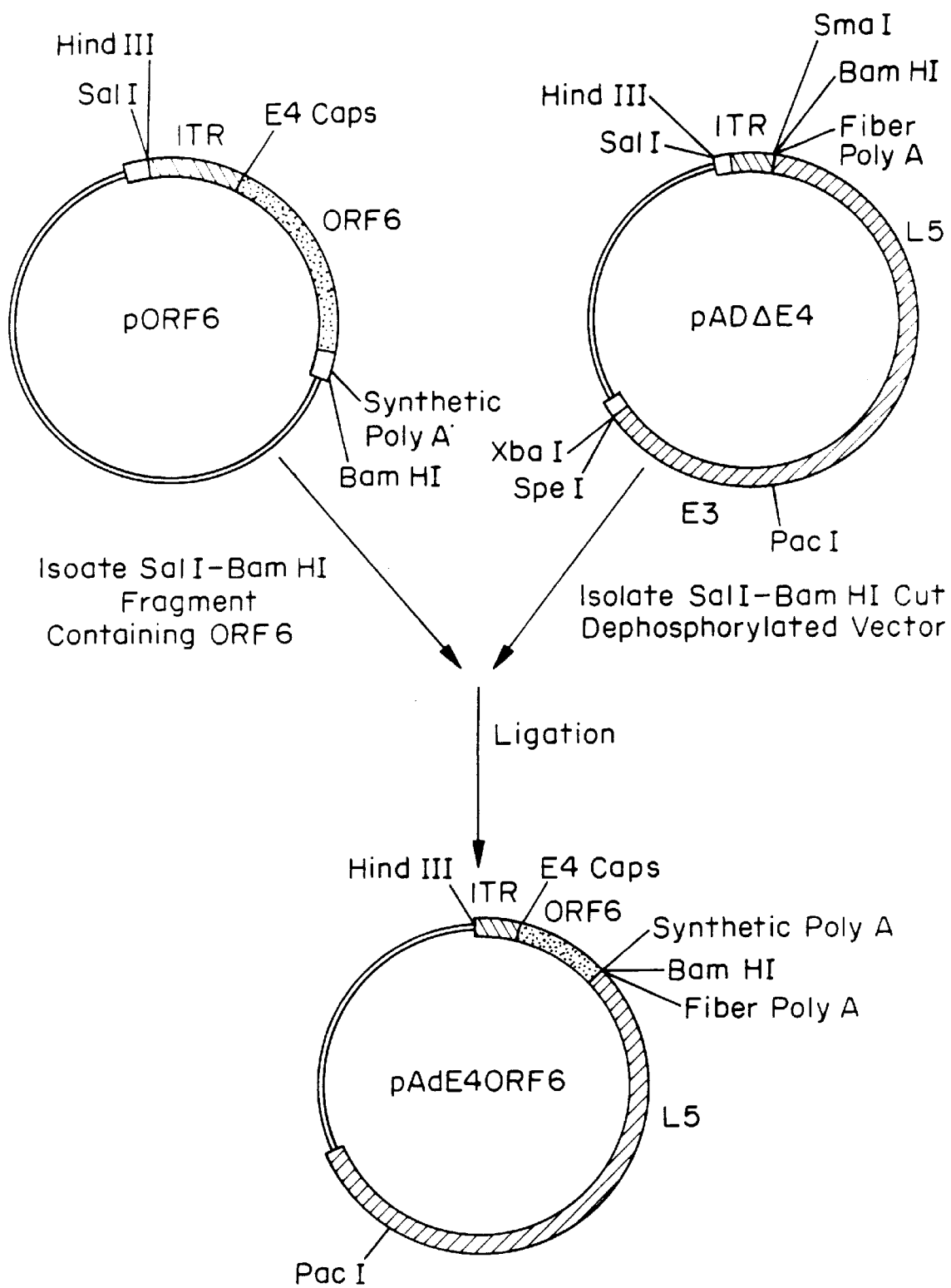

Specifically, PAV contains adenovirus 2 (Ad2) sequences as shown in FIG. 17, from nucleotide (nt) 0–356 forming the 5' end of the vector and the last 109 nt of Ad2 forming the 3' end of the construct. The sequences includes the Ad2 flanking inverted terminal repeats (5'ITR) and the 5' ITR adjoining sequences containing the known packaging signal and E1a enhancer. Various convenient restriction sites have been incorporated into the fragments, allowing the insertion of promoter/gene cassettes which can be packaged in the PAV virion and used for gene transfer (e.g. for gene therapy). The construction and propagation of PAV is described in detail in the following Example 11. By not containing most native adenoviral DNA, the PAVs described herein are less likely to produce a patient immune reponse or to replicate in a host.

In addition, the PAV vectors can accomodate foreign DNA up to a maximum length of nearly 36 kb. The PAV vectors therefore, are especially useful for cloning larger genes (e.g., CFTR (7.5 kb)); Factor VIII (8 kb); Factor IX (9 kb)), which, traditional vectors have difficulty accomodating. In addition, PAV vectors can be used to transfer more than one gene, or more than one copy of a particular gene. For example, for gene therapy of cystic fibrosis, PAVs can be used to deliver CFTR in conjunction with other genes such as anti proteases (e.g., antiprotease alpha-l-antitrypsin) tissue inhibitor of metaloproteinase, antioxidants (e.g., superoxide dismutase), enhancers of local host defense (e.g., interferons), mucolytics (e.g., DNase); and proteins which block inflammatory cytokines.

Ad2-E4/ORF6 Adenovirus Vectors

An adenoviral construct expressing only the open reading frame 6 (ORF6) of adenoviral early region 4 (E4) from the E4 promoter and which is deleted for all other known E4 open reading frames was constructed as described in detail in Example 12. Expression of E4 open reading frame 3 is also sufficient to provide E4 functions required for DNA replication and late protein synthesis. However, it provides these functions with reduced efficiency compared to expression of ORF6, which will likely result in lower levels of virus production. Therefore expressing ORF6, rather than ORF3, appears to be a better choice for producing recombinant adenovirus vectors.

The E4 region of adenovirus is suspected to have a role in viral DNA replication, late mRNA synthesis and host protein synthesis shut off, as well as in viral assembly (Falgout, B. and G. Ketner (1987) *J. Virol.* 61:3759–3768). Adenovirus early region 4 is required for efficient virus particle assembly. Adenovirus early region 4 encodes functions required for efficient DNA replication, late gene expression, and host cell shutoff. Halbert, D. N. et al. (1985) *J. Virol.* 56:250–257.

The deletion of non-essential open reading frames of E4 increases the cloning capacity of recombinant adenovirus vectors by approximately 2 kb of insert DNA without significantly reducing the viability of the virus in cell culture. When placed in combination with deletions in the E1 and/or E3 regions of adenovirus vectors, the theoretical insert capacity of the resultant vectors is increased to 8–9 kb. An example of where this increased cloning capacity may prove useful is in the development of a gene therapy vector encoding CFTR. As described above, the first generation adenoviral vector approaches the maximum packaging capacity for viral DNA encapsidation. As a result, this virus grows poorly and may occassionaly give rise to defective progeny. Including an E4 deletion in the adenovirus vector should alleviate these problems. In addition, it allows flexibility in the choice of promoters to drive CFTR expression from the virus. For example, strong promoters such as the adenovirus major late promoter, the cytomegalovirus immediate early promoter or a cellular promoter such as the CFTR promoter, which may be too large for first-generation adenovirus can be used to drive expression.

In addition, by expressing only ORF6 of E4, these second generation adenoviral vectors may be safer for use in gene therapy. Although ORF6 expression is sufficient for viral DNA replication and late protein synthesis in immortalized cells, it has been suggested that ORF6/7 of E4 may also be required in non-dividing primary cells (Hemstrom, C. et al. (1991) *J. Virol.* 65:1440–1449). The 19 kD protein produced from open reading frame 6 and 7 (ORF6/7) complexes with and activates cellular transcription factor E2F, which is required for maximal activation of early region 2. Early region 2 encodes proteins required for viral DNA replication. Activated transcription factor E2F is present in proliferating cells and is involved in the expression of genes required for cell proliferation (e.g., DHFR, c-myc), whereas activated E2F is present in lower levels in non-proliferating cells. Therefore, the expression of only ORF6 of E4 should allow the virus to replicate normally in tissue culture cells (e.g., 293 cells), but the absence of ORF6/7 would prevent the potential activation of transcription factor E2F in non-dividing primary cells and thereby reduce the potential for viral DNA replication.

Target Tissue

Because 95% of CF patients die of lung disease, the lung is a preferred target for gene therapy. The hallmark abnormality of the disease is defective electrolyte transport by the epithelial cells that line the airways. Numerous investigators (reviewed in Quinton, F. (1990) *FASEB J.* 4:2709) have observed: a) a complete loss of cAMP-mediated transepithelial chloride secretion, and b) a two to three fold increase in the rate of Na+ absorption. cAMP-stimulated chloride secretion requires a chloride channel in the apical membrane (Welsh, M. J. (1987) *Physiol Rev.* 67:1143–1184). The discovery that CFTR is a phosphorylation-regulated chloride channel and that the properties of the CFTR chloride channel are the same as those of the chloride channels in the apical membrane, indicate that CFTR itself mediates transepithelial chloride secretion. This conclusion was supported by studies localizing CFTR in lung tissue: CFTR is located in the apical membrane of airway epithelial cells (Denning, G. M. et al. (1992) *J. Cell BioL* 118:551) and has been reported to be present in the submucosal glands (Taussig et al., (1973) *J. Clin. Invest* 89:339). As a consequence of loss of CFTR function, there is a loss of cAMP-regulated transepithelial chloride secretion. At this time it is uncertain how dysfunction of CFTR produces an increase in the rate of Na+ absorption. However, it is thought that the defective chloride secretion and increased Na+ absorption lead to an alteration of the respiratory tract fluid and hence, to defective mucociliary clearance, a normal pulmonary defense mechanism. As a result, clearance of inhaled material from the lung is impaired and repeated infections ensue. Although the presumed abnormalities in respiratory tract fluid and mucociliary clearance provide a plausible explanation for the disease, a precise understanding of the pathogenesis is still lacking.

Correction of the genetic defect in the airway epithelial cells is likely to reverse the CF pulmonary phenotype. The identity of the specific cells in the airway epithelium that express CFTR cannot be accurately determined by immunocytochemical means, because of the low abundance of protein. However, functional studies suggest that the ciliated epithelial cells and perhaps nonciliated cells of the surface epithelium are among the main cell types involved in electrolyte transport. Thus, in practical terms, the present preferred target cell for gene therapy would appear to be the mature cells that line the pulmonary airways. These are not rapidly dividing cells; rather, most of them are nonproliferating and many may be terminally differentiated. The identification of the progenitor cells in the airway is uncertain.

Although CFTR may also be present in submucosal glands (Trezise, A. E. and Buchwald, M. (1991) *Nature* 353:434; Englehardt, J. F. et al. (1992) *J. Clin. Invest.* 90:2598–2607), there is no data as to its function at that site; furthermore, such glands appear to be relatively inaccessible.

The airway epithelium provides two main advantages for gene therapy. First, access to the airway epithelium can be relatively noninvasive. This is a significant advantage in the development of delivery strategies and it will allow investigators to monitor the therapeutic response. Second, the epithelium forms a barrier between the airway lumen and the interstitium. Thus, application of the vector to the lumen will allow access to the target cell yet, at least to some extent, limit movement through the epithelial barrier to the interstitium and from there to the rest of the body.

Efficiency of Gene Delivery Required to Correct The Genetic Defect

It is unlikely that any gene therapy protocol will correct 100% of the cells that normally express CFTR. However, several observations suggest that correction of a small percent of the involved cells or expression of a fraction of the normal amount of CFTR may be of therapeutic benefit.

a. CF is an autosomal recessive disease and heterozygotes have no lung disease.

Thus, 50% of wild-type CFTR would appear sufficient for normal function.

b. This issue was tested in mixing experiments using CF cells and recombinant CF cells expressing wild-type CFTR (Johnson, L. G. et al. (1992) *Nature Gen* 2:21). The data obtained showed that when an epithelium is reconstituted with as few as 6–10% of corrected cells, chloride secretion is comparable to that observed with an epithelium containing 100% corrected cells. Although CFTR expression in the recombinant cells is probably higher than in normal cells, this result suggests that in vivo correction of all CF airway cells may not be required.

c. Recent observations show that CFTR containing some CF-associated mutations retains residual chloride channel activity (Sheppard, D. N. et al. (1992) *Pediatr. Pulmon Suppl.* 8:250; Strong, T. V. et al. (1991) *N. Eng. J. Med.* 325:1630). These mutations are associated with mild lung disease. Thus, even a very low level of CFTR activity may at least partly ameliorate the electrolyte transport abnormalities.

d. As indicated in experiments described below in Example 8, complementation of CF epithelia, under conditions that probably would not cause expression of CFTR in every cell, restored cAMP stimulated chloride secretion.

e. Levels of CFTR in normal human airway epithelia are very low and are barely detectable. It has not been detected using routine biochemical techniques such as immunoprecipitation or immunoblotting and has been exceedingly difficult to detect with immunocytochemical techniques (Denning, G. M. et al. (1992) *J. Cell Biol.* 118:551). Although CFTR has been detected in some cases using laser-scanning confocal microscopy, the signal is at the limits of detection and cannot be detected above background in every case. Despite that minimal levels of CFTR, this small amount is sufficient to generate substantial cAMP-stimulated chloride secretion. The reason that a very small number of CFTR chloride channels can support a large chloride secretory rate is that a large number of ions can pass through a single channel ($10^6$–$10^7$ ions/sec) (Hille, B. (1984) Sinauer Assoc. Inc., Sunderland, Mass. 420426).

f. Previous studies using quantitative PCR have reported that the airway epithelial cells contain at most one to two transcripts per cell (Trapnell, B. C. et al. (1991) *Proc. Natl. Acad Sci. USA* 88:6565).

Gene therapy for CF would appear to have a wide therapeutic index. Just as partial expression may be of therapeutic value, overexpression of wild-type CFTR appears unlikely to cause significant problems. This conclusion is based on both theoretical considerations and experimental results. Because CFTR is a regulated channel, and because it has a specific function in epithelia it is unlikely that overexpression of CFTR will lead to uncontrolled chloride secretion. First, secretion would require activation of CFTR by cAMP-dependent phosphorylation. Activation of this kinase is a highly regulated process. Second, even if CFTR chloride channels open in the apical membrane, secretion will not ensue without regulation of the basolateral membrane transporters that are required for chloride to enter the cell from the interstitial space. At the basolateral membrane, the sodium-potassium-chloride cotransporter and potassium channels serve as important regulators of transeptihelial secretion (Welsh, M. J. (1987) *Physio. Rev.* 67:1143–1184).

Human CFTR has been expressed in transgenic mice under the control of the surfactant protein C(SPC) gene promoter (Whitesett, J. A. et al. (1992) *Nature Gen.* 2:13) and the casein promoter (Ditullio, P. et al (1992) *Bio/Technology* 10:74 ). In those mice, CFTR was overexpressed in bronchiolar and alveolar epithelial cells and in the mammary glands, respectively. Yet despite the massive overexpression in the transgenic animals, there were no observable morphologic or functional abnormalities. In addition, expression of CFTR in the lungs of cotton rats produced no reported abnormalities (Rosenfeld, M. A. et al. (1992) *Cell* 68:143–155).

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example 1

Generation of Full Length CFTR cDNAs

Figure 1:
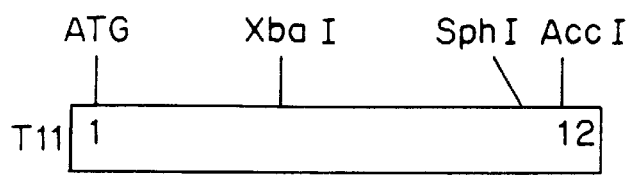
FIG. 1 shows alignment of CFTR partial cDNA clones used in construction of cDNA containing complete coding sequence of the CFTR; only restriction sites relevant to the DNA constructions described below are shown.
Figure 1:
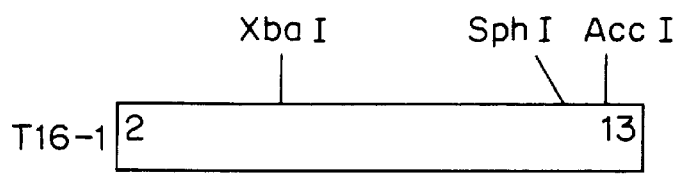
Figure 1:
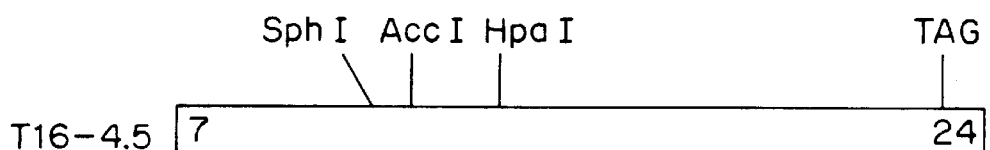
Figure 1:
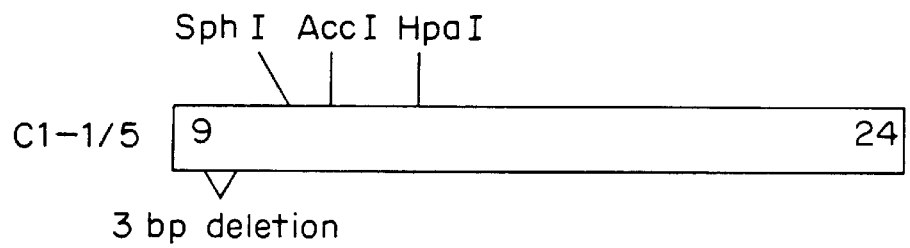
Figure 2:
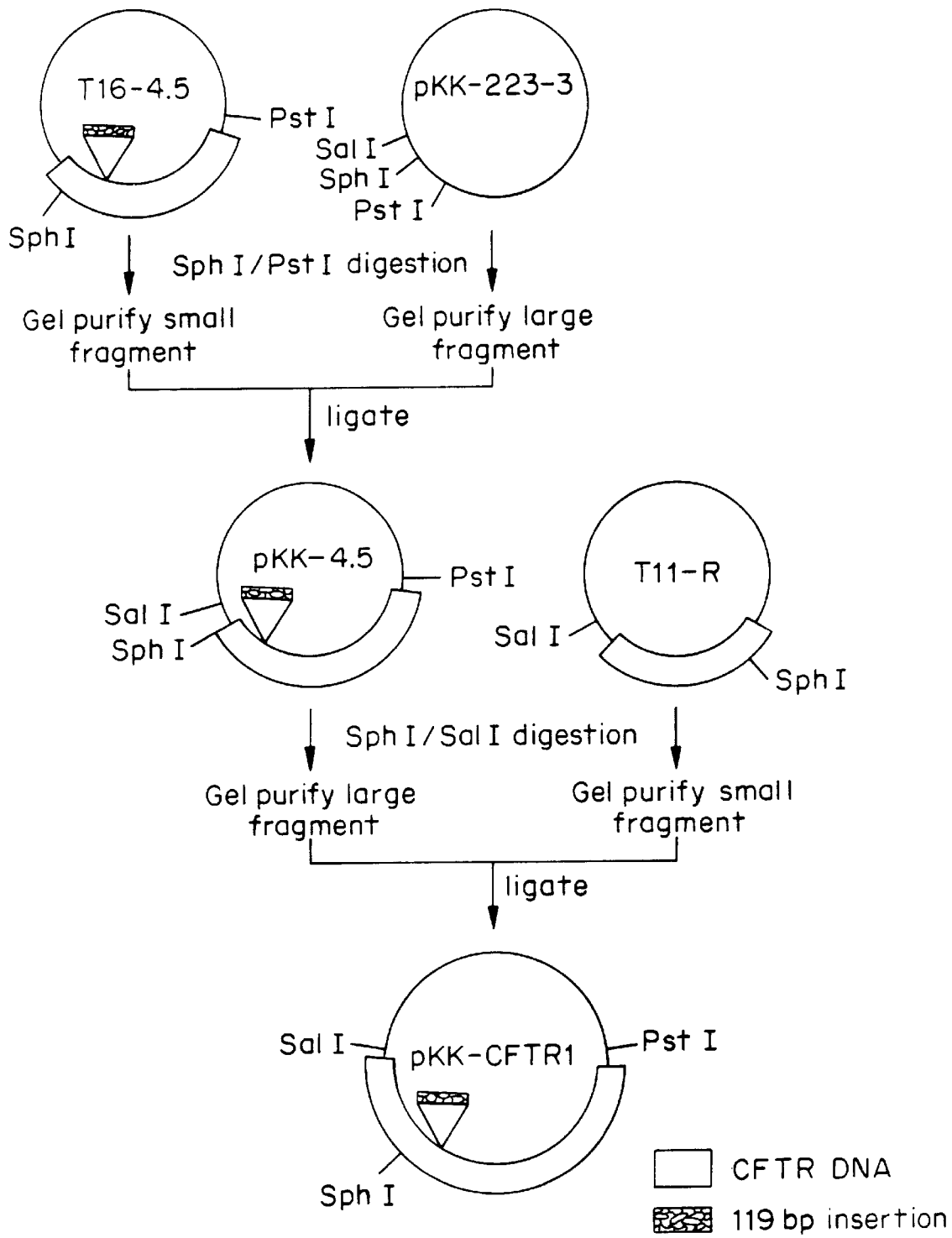
FIG. 2 depicts plasmid construction of the CFTR cDNA clone pKK-CFTR1.

Nearly all of the commonly used DNA cloning vectors are based on plasmids containing modified pMBI replication origins and are present at up to 500 to 700 copies per cell (Sambrook et al. Molecular Cloning: A Laboratory Manual (Cold Spring Harbor Laboratory Press 1989). The partial CFTR cDNA clones isolated by Riordan et al. were maintained in such a plasmid. It was postulated that an alternative theory to intrinsic clone instability to explain the apparent inability to recover clones encoding full length CFTR protein using high cot number plasmids, was that it was not possible to clone large segments of the CFTR cDNA at high gene dosage in *E coli*. Expression of the CFTR or portions of the CFTR from regulatory sequences capable of directing transcription and/or translation in the bacterial host cell might result in inviability of the host cell due to toxicity of the transcript or of the full length CFTR protein or fragments thereof. This inadvertent gene expression could occur from either plasmid regulatory sequences or cryptic regulatory sequences within the recombinant CFTR plasmid which are capable of functioning in *E. coli*. Toxic expression of the CFTR coding sequences would be greatly compounded if a large number of copies of the CFTR cDNA were present in cells because a high copy number plasmid was used. If the product was indeed toxic as postulated, the growth of cells containing fall length and correct sequence would be actively disfavored. Based upon this novel hypothesis, the following procedures were undertaken. With reference to FIG. 2, partial CFTR clone T164.5 was cleaved with restriction enzymes Sph 1 and Pst 1 and the resulting 3.9 kb restriction fragment containing exons 11 through most of exon 24 (including an uncharacterized 119 bp insertion reported by Riordan et al. between nucleotides 1716 and 1717), was isolated by agarose gel purification and ligated between the Sph 1 and Pst 1 sites of the pMB1 based vector pkk223-3 (Brosius and Holy, (1984) *Proc. Natl. Acad Sci* 81:6929). It was hoped that the pMB1 origin contained within this plasmid would allow it and plasmids constructed from it to replicate at 15–20 copies per host *E. coli* cell (Sambrook et al. Molecular Cloning: A Laboratory Manual (Cold Spring Harbor Laboratory Press 1989). The resultant plasmid clone was called pkk-4.5.

Partial CFTR clone T11 was cleaved with Eco R1 and Hinc II and the 1.9 kb band encoding the first 1786 nucleotides of the CFTR cDNA plus an additional 100 bp of DNA at the 5' end was isolated by agarose gel purification. This restriction fragment was inserted between the Eco R1 site and Sma 1 restriction site of the plamid Bluescript Sk- (Stratagene, catalogue number 212206), such that the CFTR sequences were now flanked on the upstream (5') side by a Sal 1 site from the cloning vector. This clone, designated T11-R, was cleaved with Sal 1 and Sph 1 and the resultant 1.8 kb band isolated by agarose gel purification. Plasmid pkk4.5 was cleaved with Sal 1 and Sph 1 and the large fragment was isolated by agarose gel purification. The purified T11-R fragment and pkk4.5 fragments were ligated to construct pkk-CFTR1. pkk-CFTR1 contains exons 1 through 24 of the CFTR cDNA. It was discovered that this plasmid is stably maintained in *E. coli* cells and confers no measureably disadvantageous growth characteristics upon host cells.

pkk-CFTR1 contains, between nucleotides 1716 and 1717, the 119 bp insert DNA derived from partial cDNA clone T164.5 described above. In addition, subsequent sequence analysis of pkk-CFTR1 revealed unreported differences in the coding sequence between that portion of CFTR1 derived from partial cDNA clone T11 and the published CFTR cDNA sequence. These undesired differences included a 1 base-pair deletion at position 995 and a C to T transition at position 1507.

Figure 3:
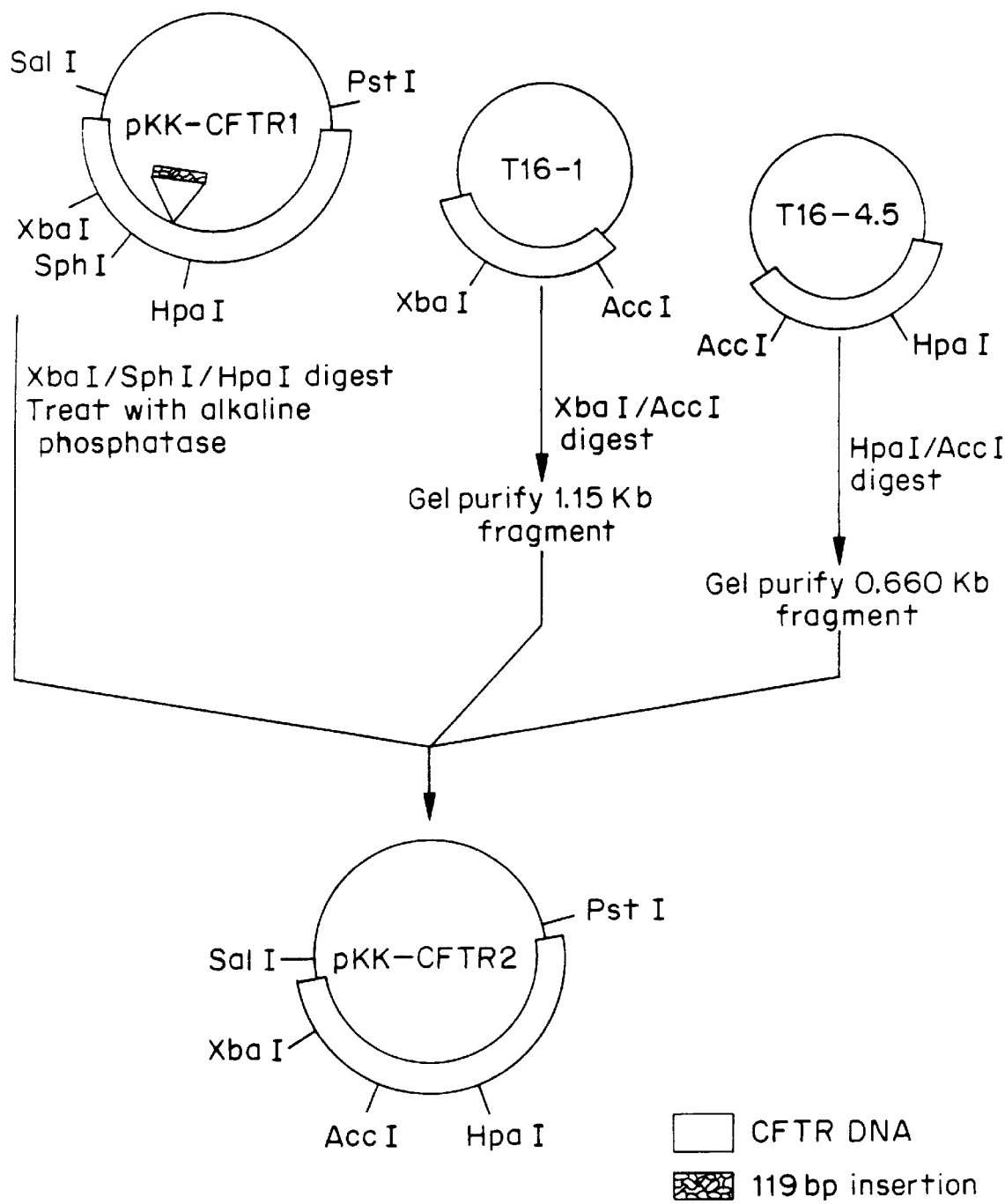
FIG. 3 depicts plasmid construction of the CFTR cDNA clone pKK-CFTR2.

To complete construction of an intact correct CFTR coding sequence without mutations or insertions and with reference to the construction scheme shown in FIG. 3, pkk-CFTR1 was cleaved with Xba I and Hpa I, and dephosphorylated with calf intestinal alkaline phosphatase. In addition, to reduce the likelihood of recovering the original

17 clone, the small unwanted Xba I/Hpa I restriction fragment from pKK-CFTR1 was digested with Sph I. T 16-1 was cleaved with Xba I and Acc I and the 1.15 kb fragment isolated by agarose gel purification. T164.5 was cleaved with Acc I and Hpa I and the 0.65 kb band was also isolated by agarose gel purification. The two agarose gel purified restriction fragments and the dephosphorylated pKK-CFTR1 were ligated to produce pKK-CFTR2. Alternatively, pKK-CFTR2 could have been constructed using corresponding restriction fragments from the partial CFTR cDNA clone C1-1/5. pKK-CFTR2 contains the uninterrupted CFTR protein coding sequence and conferred slow growth upon E. coli host cells in which it was inserted, whereas pKK-CFTR1 did not. The origin of replication of pKK-CFTR2 is derived from pMB1 and confers a plasmid copy number of 15–20 copies per host cell.

Example 2

Improving Host Cell Viability

An additional enhancement of host cell viability was accomplished by a further reduction in the copy number of CFTR cDNA per host cell. This was achieved by transferring the CFTR cDNA into the plasmid vector, pSC-3Z. pSC-3Z was constructed using the pSC101 replication origin of the low copy number plasmid pLG338 (Stoker et al., Gene 18, 335 (1982)) and the ampicillin resistance gene and polylinker of pGEM-3Z (available from Promega). pLG338 was cleaved with Sph I and pVu II and the 2.8 kb fragment containing the replication origin isolated by agarose gel purification. pGEM-3Z was cleaved with ALw NI, the resultant restriction fragment ends treated with T4 DNA polymerase and deoxynucleotide triphosphates, cleaved with Sph I and the 1.9 kb band containing the ampicillin resistance gene and the polylinker was isolated by agarose gel purification. The pLG338 and pGEM-3Z fragments were ligated together to produce the low copy number cloning vector pSC-3Z. pSC-3Z and other plasmids containing pSC101 origins of replication are maintained at approximately five copies per cell (Sambrook et al.).

Figure 4:
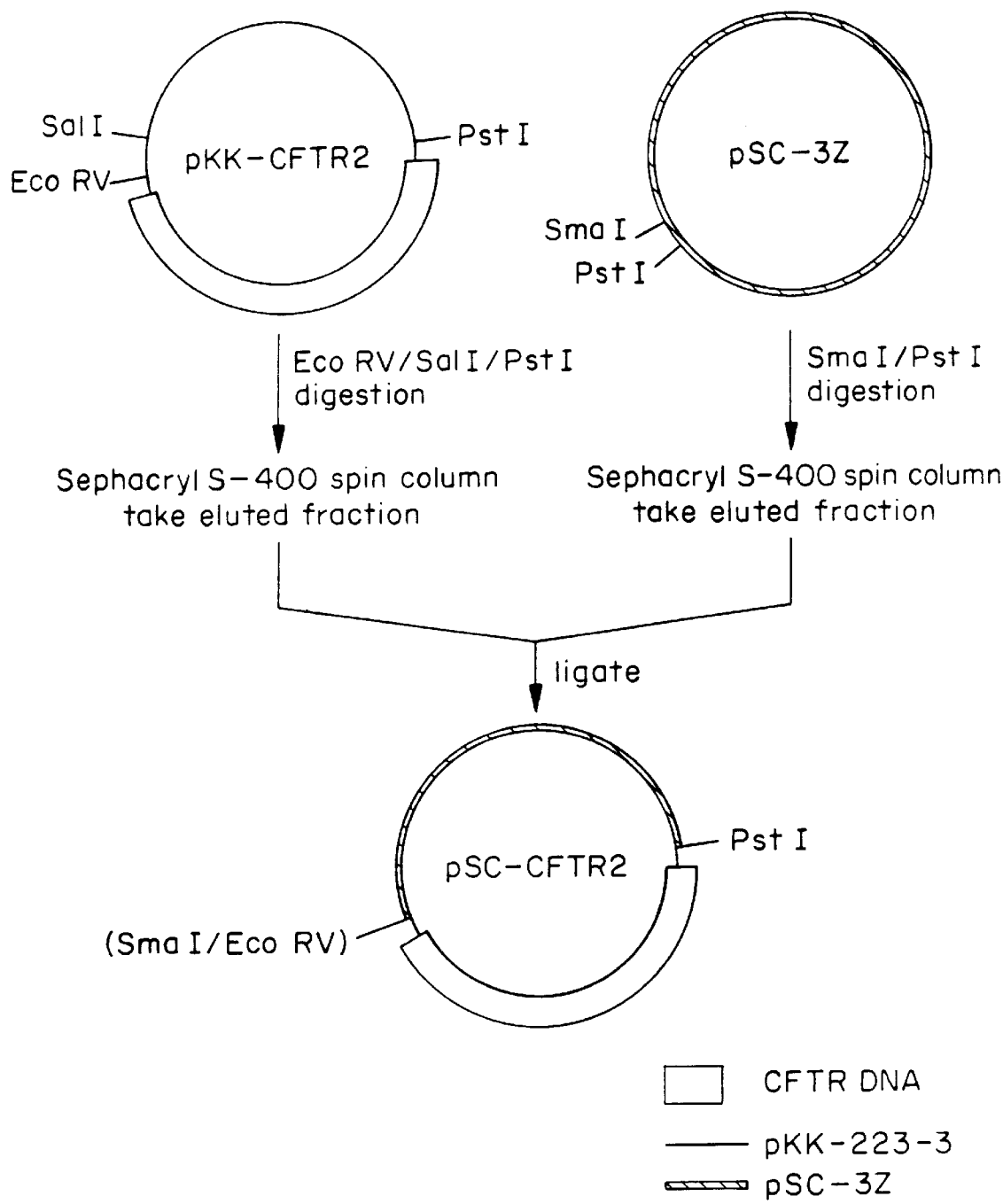
FIG. 4 depicts plasmid construction of the CFTR cDNA clone pSC-CFTR2.
Figure 5:
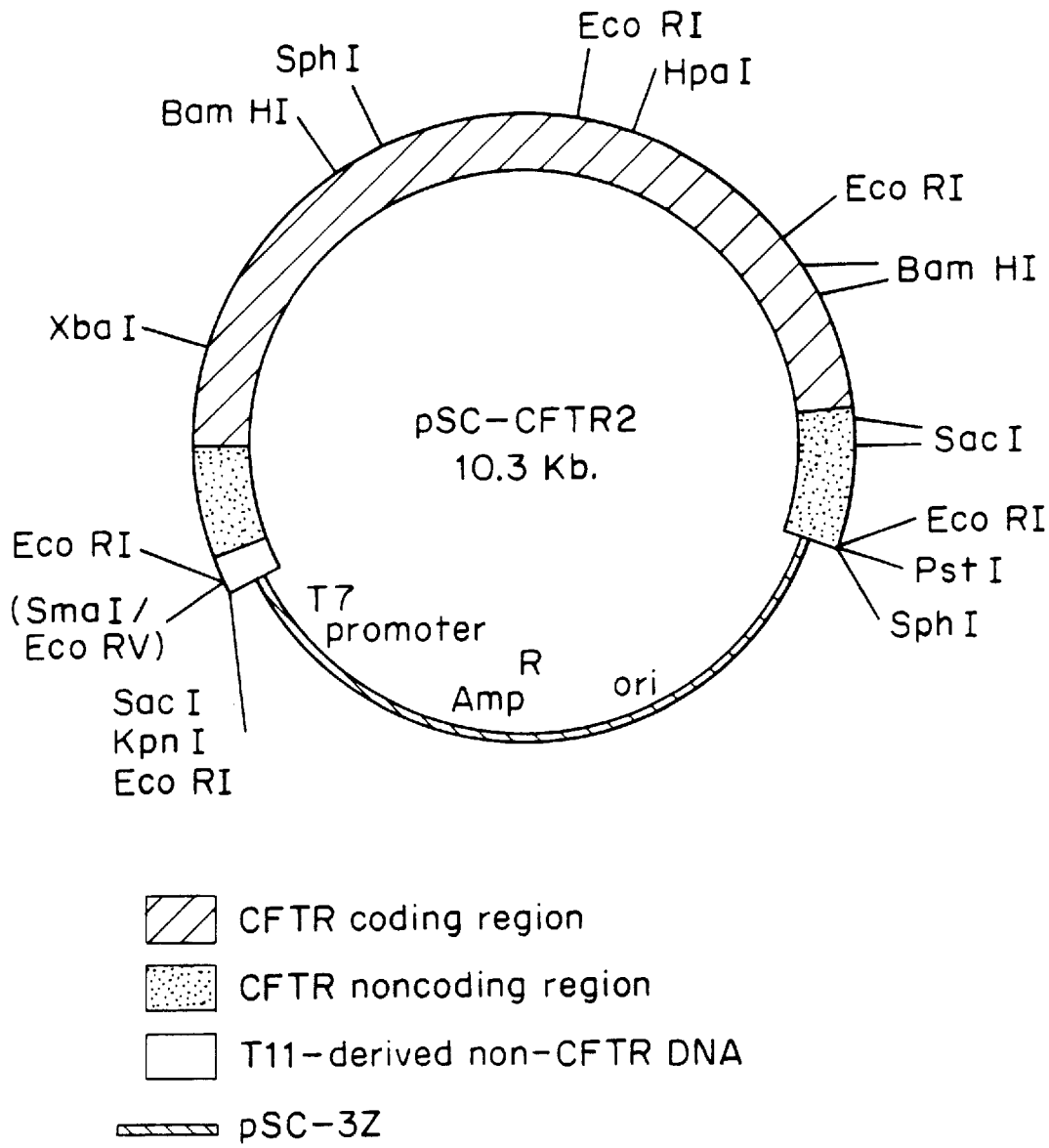
FIG. 5 shows a plasmid map of the CFTR cDNA clone pSC-CFTR2.

With additional reference to FIG. 4, pKK-CFTR2 was cleaved with Eco RV, Pst I and Sal I and then passed over a Sephacryl S400 spun column (available from Pharmacia) according to the manufacturer's procedure in order to remove the Sal I to Eco RV restriction fragment which was retained within the column. pSC-3Z was digested with Sma I and Pst I and also passed over a Sephacryl S400 spun column to remove the small Sma I/Pst I restriction fragment which was retained within the column. The column eluted fractions from the pKK-CFTR2 digest and the pSC-3Z digest were mixed and ligated to produce pSC-CFTR2. A map of this plasmid is presented in FIG. 5. Host cells containing CFTR cDNAs at this and similar gene dosages grow well and have stably maintained the recombinant plasmid with the full length CFTR coding sequence. In addition, this plasmid contains a bacteriophage T7 RNA polymerase promoter adjacent to the CFTR coding sequence and is therefore convenient for in vitro transcription/translation of the CFTR protein. The nucleotide sequence of CFTR coding region from pSC-CFTR2 plasmid is presented in Sequence Listing 1 as SEQ ID NO:1. Significantly, this sequence differs from the previously published (Riordan, J. R. et al. (1989) Science 245:1066–1073) CFTR sequence at position 1990, where there is C in place of the reported A. See Gregory, R. J. et al. (1990) Nature 347:382–386. E. coli host cells containing pSC-CFTR2, internally identified with the number pSC-CFTR2/AG1, have been deposited at the American Type Culture Collection and given the accession number: ATCC 68244.

18

Example 3

Alternate Method for Improving Host Cell Viability

A second method for enhancing host cell viability comprises disruption of the CFTR protein coding sequence. For this purpose, a synthetic intron was designed for insertion between nucleotides 1716 and 1717 of the CFTR cDNA. This intron is especially advantageous because of its easily manageable size. Furthermore, it is designed to be efficiently spliced from CFTR primary RNA transcripts when expressed in eukaryotic cells. Four synthetic oligonucleotides were synthesized (1195RG, 1196RG, 1197RG and 1198RG) collectively extending from the Sph I cleavage site at position 1700 to the Hinc II cleavage site at position 1785 and including the additional 83 nucleotides between 1716 and 1717 (see FIG. 6) SEQ ID NO. 10. These oligonucleotides were phosphorylated with T4 polynucleotide kinase as described by Sambrook et al., mixed together, heated to 95° C. for 5 minutes in the same buffer used during phosphorylation, and allowed to cool to room temperature over several hours to allow annealing of the single stranded oligonucleotides. To insert the synthetic intron into the CFTR coding sequence and with reference to FIGS. 7A and 7B, a subclone of plasmid T11 was made by cleaving the B11 site in the polylinker, repairing the recessed ends of the cleaved DNA with deoxynucleotide triphosphates and the large fragment of DNA Polymerase I and religating the DNA. This plasmid was then digested with Eco RV and Nru I and religated. The resulting plasmid T6-A5' extended from the Nru I site at position 490 of the CFTR cDNA to the 3' end of clone T16 and contained single sites for Sph I and Hinc II at positions corresponding to nucleotides 1700 and 1785 of the CFTR cDNA. T16-Δ5' plasmid was cleaved with Sph I and Hinc II and the large fragment was isolated by agarose gel purification. The annealed synthetic oligonucleotides were ligated into this vector fragment to generate T16-intron.

T16-intron was then digested with Eco RI and Sma I and the large fragment was isolated by agarose gel purification. T164.5 was digested with Eco RI and Sca I and the 790 bp fragment was also isolated by agarose gel purification. The purified T16-intron and T16-4.5 fragments were ligated to produce T16-intron-2. T16-intron-2 contains CFTR cDNA sequences extending from the Nru I site at position 490 to the Sca I site at position 2818, and includes the unique Hpa I site at position 2463 which is not present in T16-1 or T16-intron-1.

Figure 8:
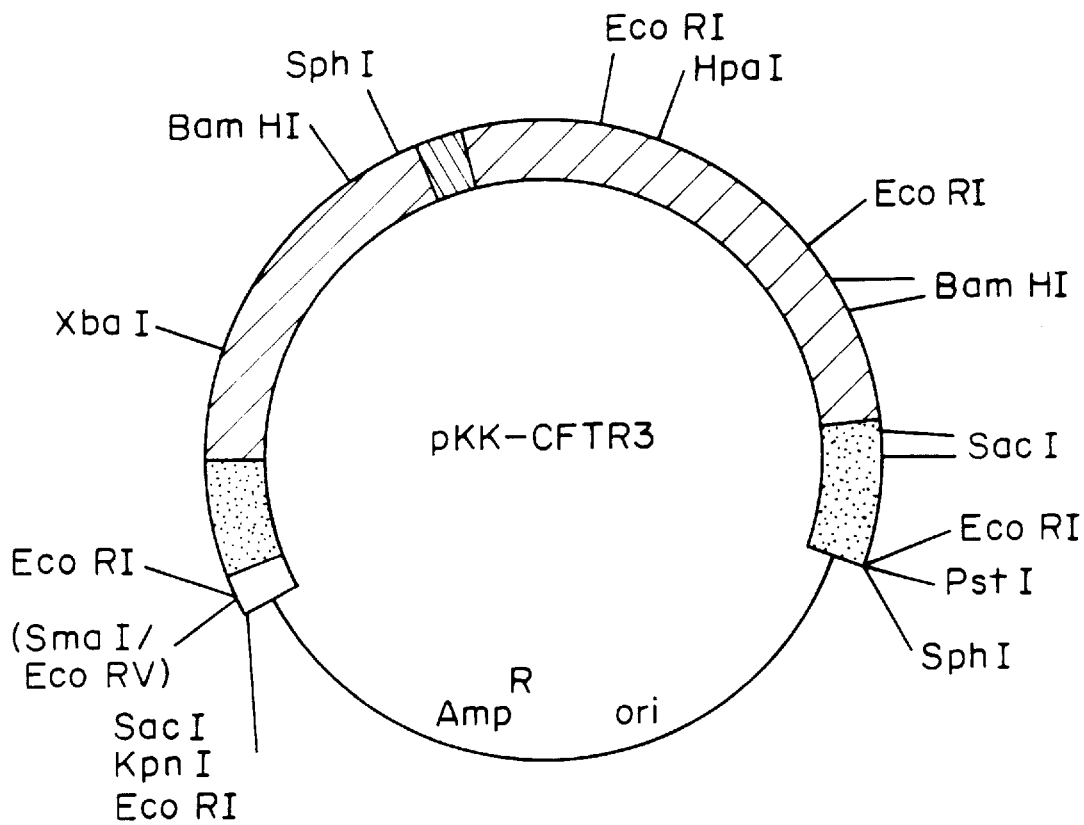
FIG. 8 shows a plasmid map of the CFTR cDNA pKK-CFTR3 containing an intron between nucleotides 1716 and 1717.
Figure 9:
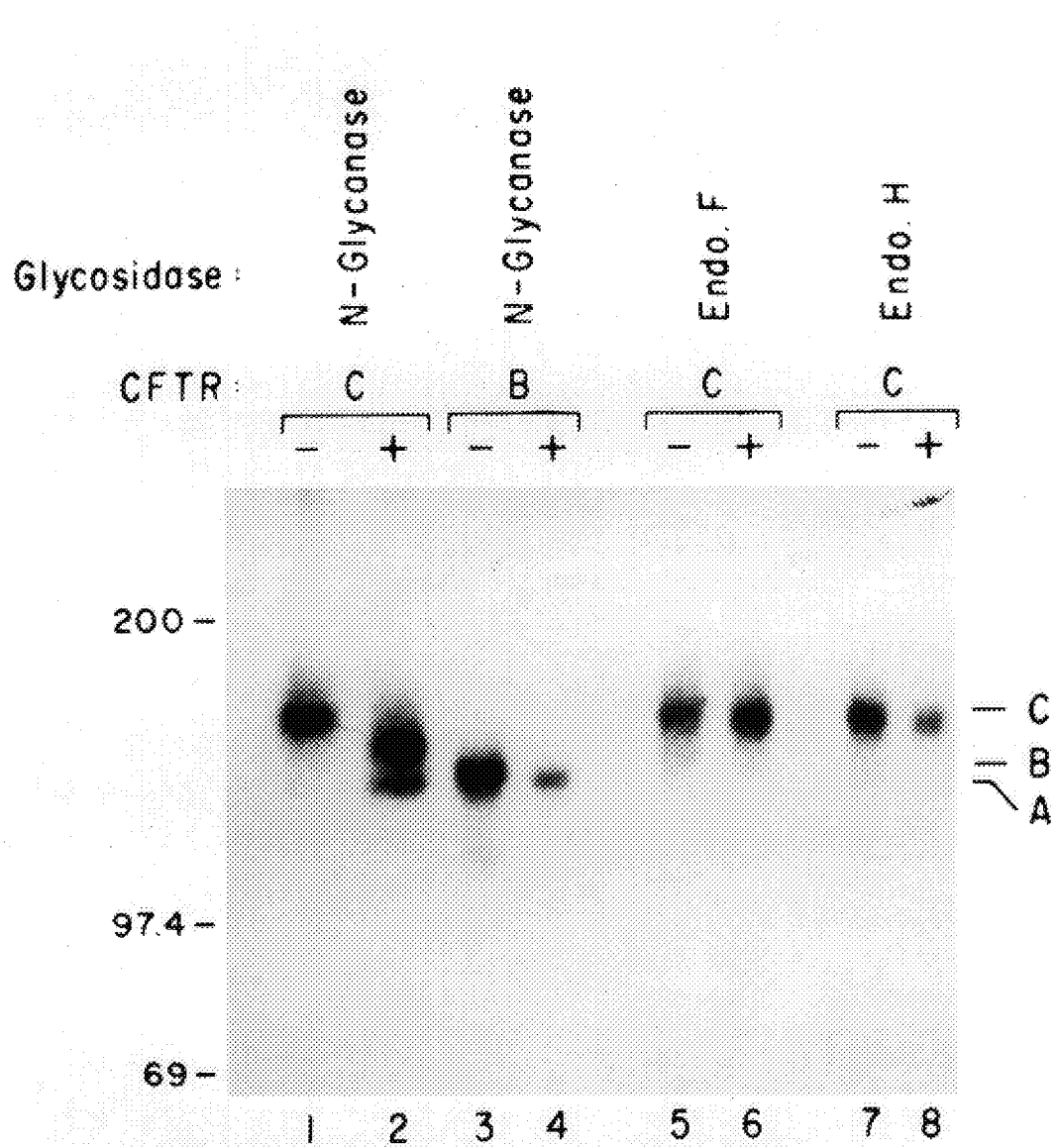
FIG. 9 shows treatment of CFTR with glycosidases.
Figure 10A:
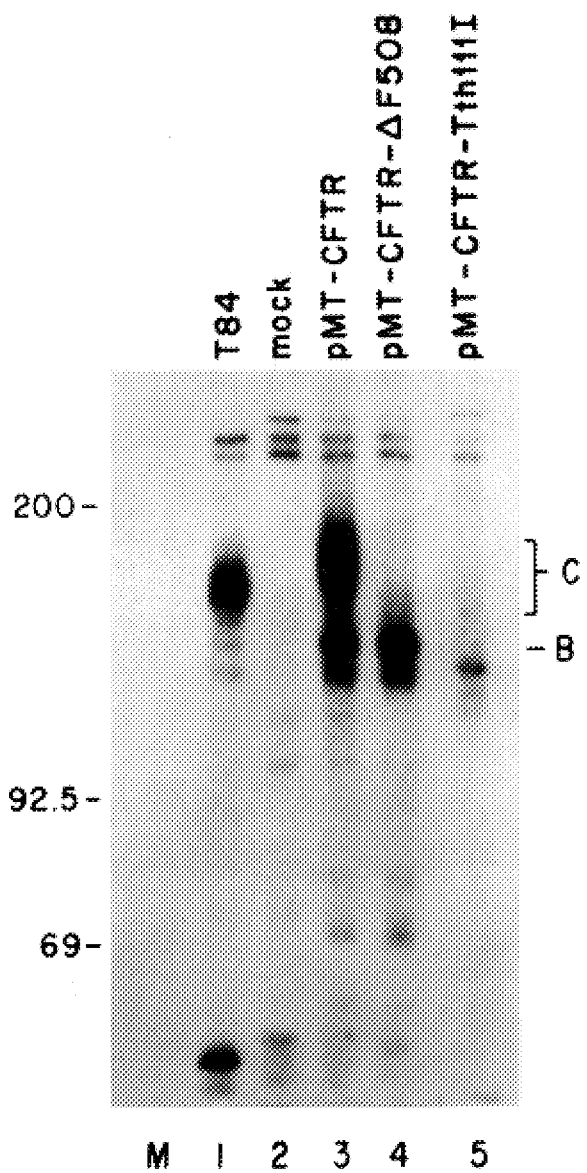
FIGS. 10A and 10B show an analysis of CFTR expressed from COS-7 transfected cells.
Figure 10B:
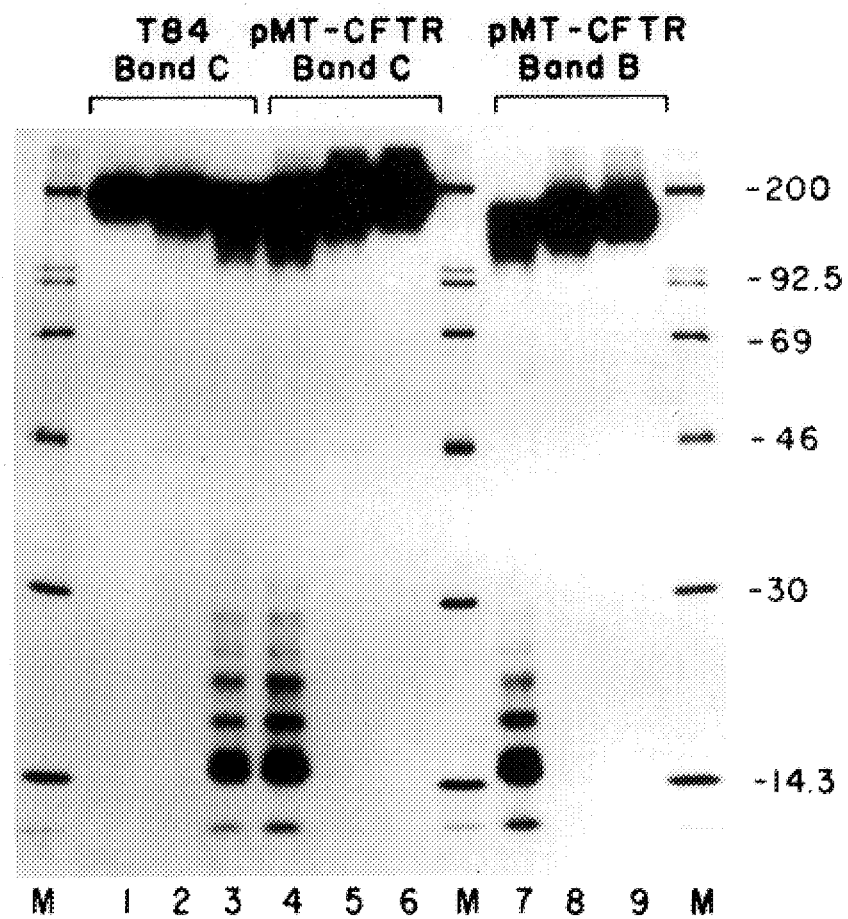
Figure 11A:
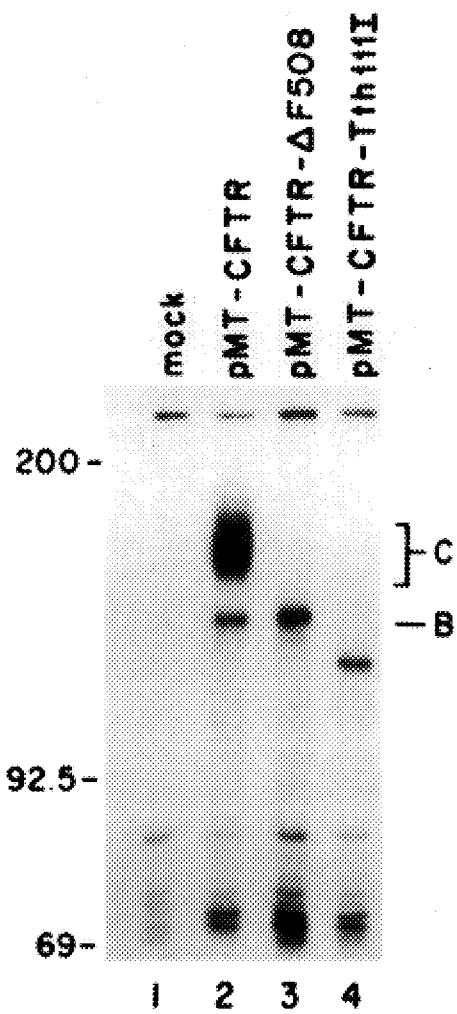
FIGS. 11A and 11B show pulse-chase labeling of wild type and ΔF508 mutant CFTR in COS-7 transfected cells.
Figure 11B:
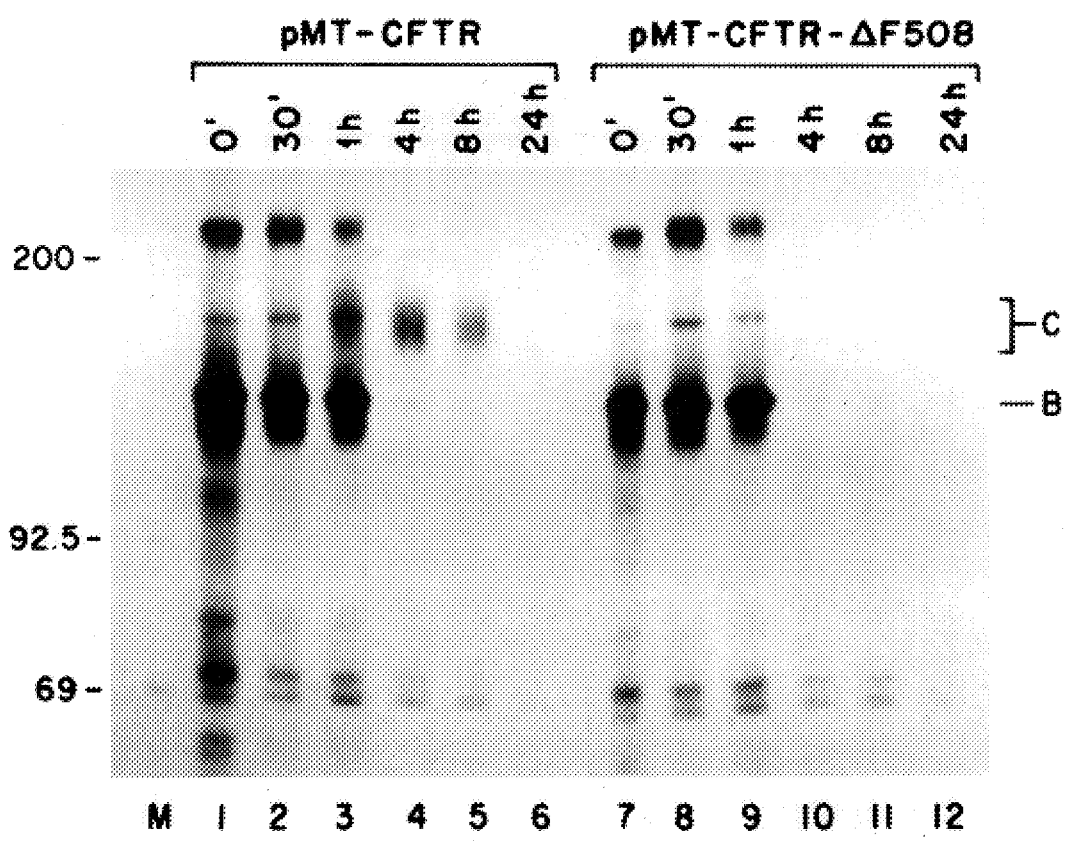
Figure 12A:
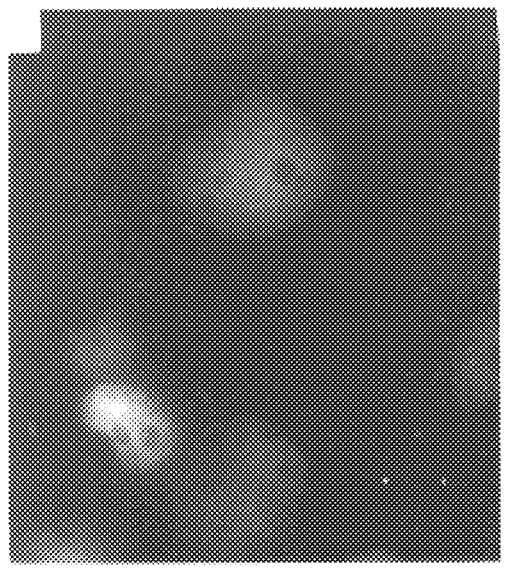
FIGS. 12A–12D show immunolocalization of wild type and ΔF508 mutant CFTR in COS-7 cells transfected with pMT-CFTR or pMT-CFTR-ΔF508.
Figure 12B:
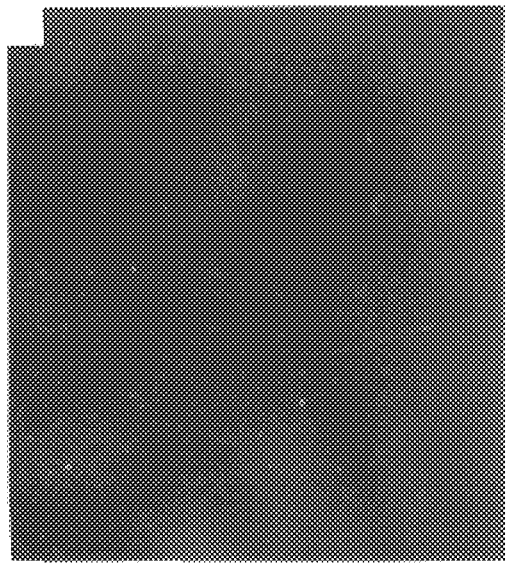
Figure 12C:
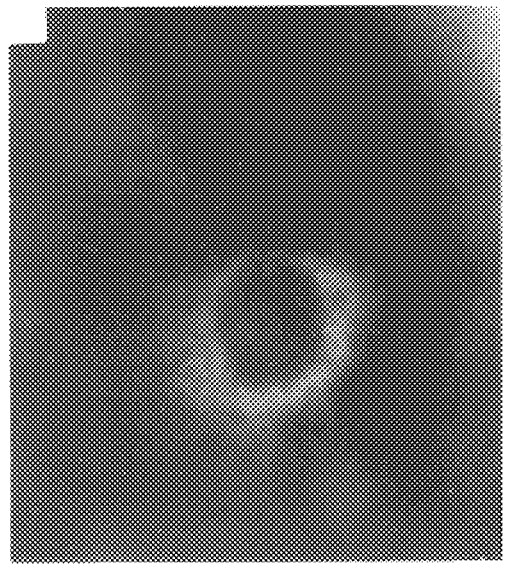
Figure 12D:
Figure 13:
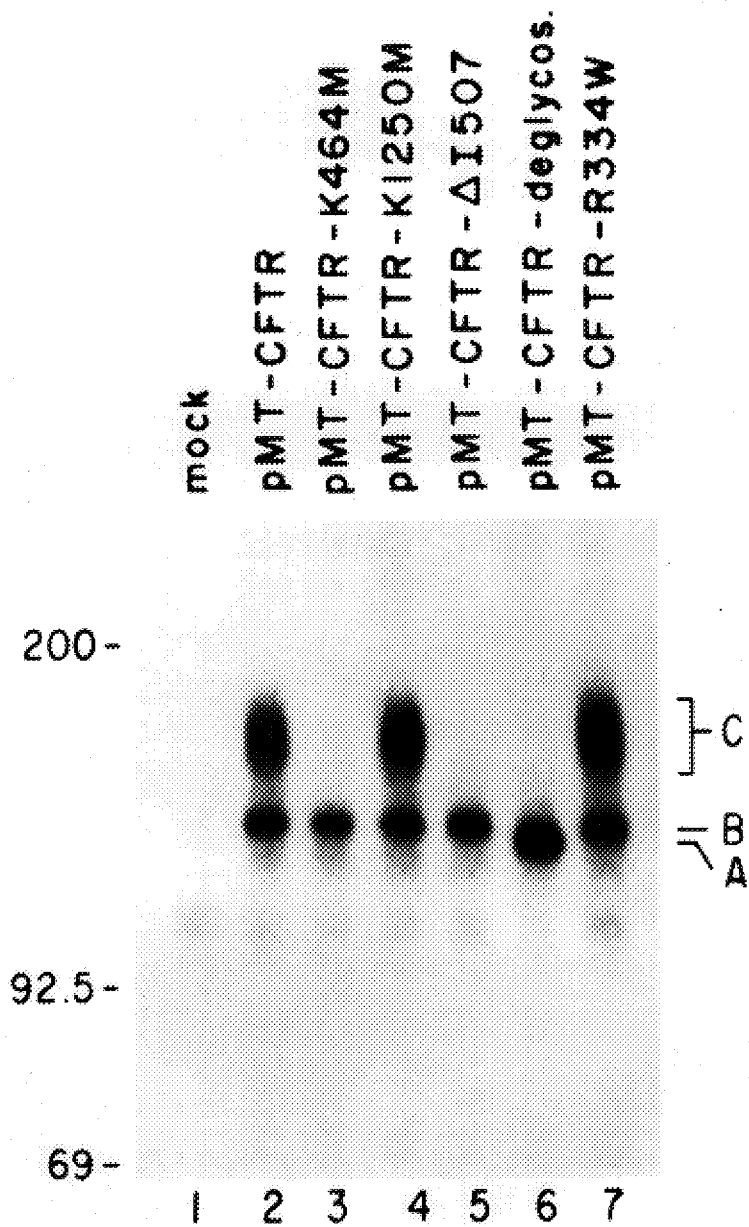
FIG. 13 shows an analysis of mutant forms of CFTR.

T-16-intron-2 was then cleaved with Xba I and Hpa I and the 1800 bp fragment was isolated by agarose gel purification. pKK-CFTR1 was digested with Xba I and Hpa I and the large fragment was also isolated by agarose gel purification and ligated with the fragment derived from T16-intron-2 to yield pKK-CFTR3, shown in FIG. 8. The CFTR cDNA within pKK-CFTR3 is identical to that within pSC-CFTR2 and pKK-CFTR2 except for the insertion of the 83 bp intron between nucleotides 1716 and 1717. The insertion of this intron resulted in improved growth characteristics for cells harboring pKK-CFTR3 relative to cells containing the unmodified CFTR cDNA in pKK-CFTR2.

Example 4

In vitro Transcription/Translation

In addition to sequence analysis, the integrity of the CFTR cDNA open reading frame was verified by in vitro transcription/translation. This method also provided the initial CFTR protein for identification purposes. 5 micrograms of pSC-CFTR2 plasmid DNA were linearized with Sal I and used to direct the synthesis of CFTR RNA transcripts with T7 RNA polymerase as described by the supplier (Stratagene). This transcript was extracted with phenol and chloroform and precipitated with ethanol. The transcript was resuspended in 25 microliters of water and varying amounts were added to a reticulocyte lysate in vitro translation system (Promega). The reactions were performed as described by the supplier in the presence of canine pancreatic microsomal membranes (Promega), using $^{35}$S-methionine to label newly synthesized proteins. In vitro translation products were analysed by discontinuous polyacrylamide gel electrophoresis in the presence of 0.1% SDS with 8% separating gels (Laemmii, U. K. (1970) Nature 227:680–685). Before electrophoresis, the in vitro translation reactions were denatured with 3% SDS, 8M urea and 5% 2-mercaptoethanol in 0.65M Tris-HCl, pH 6.8. Following electrophoresis, the gels were fixed in methanol:acetic acid:water (30:10:60), rinsed with water and impregnated with 1M sodium salicylate. $^{35}$S labelled proteins were detected by fluorgraphy. A band of approximately 180 kD was detected, consistent with translation of the full length CFTR insert.

Example 5

Elimination of Cryptic Regulatory Signals

Analysis of the DNA sequence of the CFTR has revealed the presence of a potential *E. coli* RNA polymerase promoter between nucleotides 748 and 778 which conforms well to the derived consensus sequence for *E. coli* promoters (Reznikoff and McClure, Maximizing Gene Expression, 1, Butterworth Publishers, Stoneham, Mass.). If this sequence functions as a promoter functions in *E. coli,* it could direct synthesis of potentially toxic partial CFTR polypeptides. Thus, an additional advantageous procedure for maintaining plasmids containing CFTR cDNAs in *E.coli* would be to alter the sequence of this potential promoter such that it will not function in *E. coli.* This may be accomplished without altering the amino acid sequence encoded by the CFTR cDNA. Specifically, plasmids containing complete or partial CFTR cDNA's would be altered by site-directed mutagenesis using synthetic olignucleotides (Zoller and Smith, (1983) *Methods Enzymol.* 10:468 ). More specifically, altering the nucleotide sequence at position 908 from a T to C and at position 774 from an A to a G effectively eliminates the activity of this promoter sequence without altering the amino acid coding potential of the CFTR open reading frame. Other potential regulatory signals within the CFTR cDNA for transcription and translation could also be advantageously altered and/or deleted by the same method.

Futher analysis has identified a sequence extending from nucleotide 908 to 936 which functions efficiently as a transcriptional promoter element in *E. coli* (Gregory, R. J. et al. (1990) *Nature* 347:382–386). Mutation at position 936 is capable of inactivating this promoter and allowing the CFTR cDNA to be stably maintained as a plasmid in *E. coli* (Cheng, S. H. et al. (1990) *Cell* 63:827–834). Specifically position 936 has been altered from a T to a C residue without the amino acid sequence encoded by the cDNA being altered Other mutations within this regulatory element described in Gregory, R. J. et al. (1990) *Nature* 347:382–386 could also be used to inactivate the transcriptional promoter activity. Specifically, the sequence from 908 to 913 (TTGTGA) and from 931 to 936 (GAAAAT) could be altered by site directed mutagenesis without altering the amino acid sequence encoded by the cDNA.

Example 6

Cloning of CFTR in Alternate Host Systems

Although the CFTR cDNA displays apparent toxicity in *E. coli* cells, other types of host cells may not be affected in this way. Alternative host systems in which the entire CFTR cDNA protein encoding region may be maintained and/or expressed include other bacterial species and yeast. It is not possible a priori to predict which cells might be resistant and which might not. Screening a number of different host/vector combinations is necessary to find a suitable host tolerant of expression of the full length protein or potentially toxic fragments thereof.

Example 7

Generation of Adenovirus Vector Encoding CFTR (Ad2/CFTR)

1. DNA preparation—Construction of the recombinant Ad2/CFTR-1 virus (shown as SEQ ID NO:3) was accomplished as follows: The CFTR cDNA was excised from the plasmid pCMV-CFTR-936C using restriction enzymes 1 and Ec11361. pCMV-CFTR-936C consists of a minimal CFTR cDNA encompassing nucleotides 123–4622 of the published CFTR sequence cloned into the multiple cloning site of pRC/CMV (Invitrogen Corp.) using synthetic linkers. The CFTR cDNA within this plasmid has been completely sequenced. The SpeI/EcII361 restriction fragment contains 47 bp of 5' sequence derived from synthetic linkers and the multiple cloning site of the vector.

The CFTR cDNA (the sequence of which is shown as SEQ ID NO:1 and the amino acid sequence encoded by the CFTR cDNA is shown as SEQ ID NO:2) was inserted between the NheI and SnaB1 restriction sites of the adenovirus gene transfer vector pBR-Ad2-7. pBR-Ad2-7 is a pBR322 based plasmid containing an approximately 7 kb insert derived from the 5' 10680 bp of Ad2 inserted between the ClaI and BamHI sites of pBR322. From this Ad2 fragment, the sequences corresponding to Ad2 nucleotides 546-3497 were deleted and replaced with a 12 bp multiple cloning site containing an NheI site, an MluI site, and a SnaBI site. The construct also contains the 5' inverted terminal repeat and viral packaging signals, the E1a enhancer and promoter, the E1b 3' intron and the 3' untranslated region and polyadenylation sites. The resulting plasmid was called pBR-Ad2-7/CFTR. Its use to assemble virus is described below.

2. Virus Preparation from DNA—To generate the recombinant Ad2/CFTR-1 adenovirus, the vector pBR-Ad2-7/CFTR was cleaved with BstB1 at the site corresponding to the unique BstB1 site at 10670 in Ad2. The cleaved plamid DNA was ligated to BstB1 restricted Ad2 DNA. Following ligation, the reaction was used to transfect 293 cells by the calcium phosphate procedure. Approximately 7–8 days following transfection, a single plaque appeared and was used to reinfect a dish of 293 cells. Following development of cytopathic effect (CPE), the medium was removed and saved. Total DNA was prepared from the infected cells and analyzed by restriction analysis with multiple enzymes to verify the integrity of the construct. Viral supernatant was then used to infect 293 cells and upon delvelopment of CPE, expression of CFTR was assayed by the protein kinase A (PKA) immunoprecipitation assay (Gregory, R. J. et al. (1990) *Nature* 347:382). Following these verification procedures, the virus was further purified by two rounds of plaque purification.

Plaque purified virus was grown into a small seed stock by inoculation at low multiplicities of infection onto 293 cells grown in monolayers in 925 medium supplemented with 10% bovine calf serum. Material at this stage was designated a Research Viral Seed Stock (RVSS) and was used in all preliminary experiments.

3. Virus Host Cell—Ad2/CFTR-1 is propagated in human 293 cells (ATCC CRL 1573). These cells are a human embryonal kidney cell line which were immortalized with sheared fragments of human Ad5 DNA. The 293 cell line expresses adenovirus early region 1 gene products and in consequence, will support the growth of E1 deficient adenoviruses. By analogy with retroviruses, 293 cells could be considered a packaging cell line, but they differ from usual retrovirus lines in that they do not provide missing viral structural proteins, rather, they provide only some missing viral early functions.

Production lots of virus are propagated in 293 cells derived from the Working Cell Bank (WCB). The WCB is in turn derived from the Master Cell Bank (MCB) which was grown up from a fresh vial of cells obtained from ATCC. Because 293 cells are of human origin, they are being tested extensively for the presence of biological agents. The MCB and WCB are being characterized for identity and the absence of adventitious agents by Microbiological Associates, Rockville, Md.

4. Growth of Production Lots of Virus

Production lots of Ad2/CFTR-1 are produced by inoculation of approximately $5-10 \times 10^7$ pfu of MVSS onto approximately $1-2 \times 10^7$ Wcb 293 cells grown in a T175 flask containing 25 mls of 925 medium. Inoculation is achieved by direct addition of the virus (approximately 2–5 mls) to each flask. Batches of 50–60 flasks constitute a lot.

Following 40–48 hours incubation at 37° C., the cells are shaken loose from the flask and transferred with medium to a 250 ml centrifuge bottle and spun at 1000 xg. The cell pellet is resuspended in 4 ml phosphate buffered saline containing 0.1 g/l $CaCl_2$ and 0.1 g/l $MgCl_2$ and the cells subjected to cycles of freeze-thaw to release virus. Cellular debris is removed by centrifugation at 1000 xg for 15 min. The supernatant from this centrifugation is layered on top of the CsCl step gradient: 2 ml 1.4 g/ml CsCl and 3 ml 1.25 g/ml CsCl in 10 mM Tris, 1 mM EDTA (TE) and spun for 1 hour at 35,000 rpm in a Beckman SW41 rotor. Virus is then removed from the interface between the two CsCl layers, mixed with 1.35 g/ml CsCl in TE and then subjected to a 2.5 hour equilibrium centrifugation at 75,000 rpm in a TLN-100 rotor. Virus is removed by puncturing the side of the tube with a hypodermic needle and gently removing the banded virus. To reduce the CsCl concentration, the sample is dialyzed against 2 changes of 2 liters of phosphate buffered saline with 10% sucrose.

Following this procedure, dialyzed virus is stable at 4° C. for several weeks or can be stored for-longer periods at –80° C. Aliquots of material for human use will be tested and while awaiting the results of these tests, the remainder will be stored frozen. The tests to be performed are described below:

5. Structure and Purity of Virus

SDS polyacrylamide gel electrophoresis of purified virions reveals a number of polypeptides, many of which have been characterized. When preparations of virus were subjected to one or two additional rounds of CsCl centrifugation, the protein profile obtained was indistinguishable. This indicates that additional equilibrium centrifugation does not purify the virus further, and may suggest that even the less intense bands detected in the virus preparations represent minor virion components rather than contaminating proteins. The identity of the protein bands is presently being established by N-terminal sequence analysis.

6. Contaminating Materials—The material to be administered to patients will be $2 \times 10^6$ pfu, $2 \times 10^7$ pfu and $5 \times 10^7$ pfu of purified Ad2/CFTR-1. Assuming a minimum particle to pfu ratio of 500, this corresponds to $1 \times 10^9$, $1 \times 10^{10}$ and $2.5 \times 10^{10}$ viral particles, these correspond to a dose by mass of 0.25 µg, 2.5 µg and 6.25 µg assuming a moleucular mass for adenovirus of $150 \times 10^6$.

Figure 6:
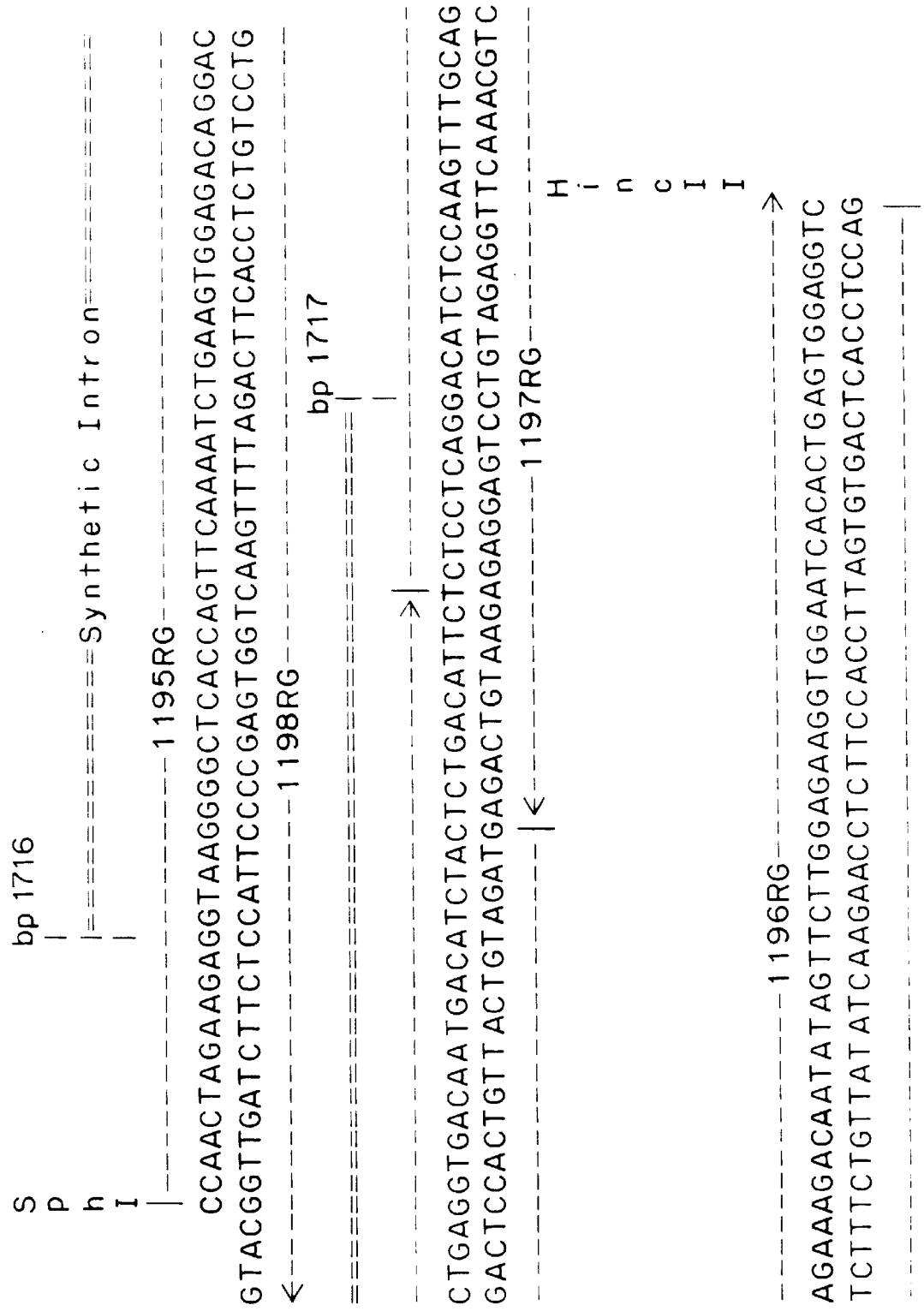
FIG. 6 shows the DNA sequence of synthetic DNAs used for insertion of an intron into the CFTR cDNA sequence, with the relevant restriction endonuclease sites and nucleotide positions noted.
Figure 7A:
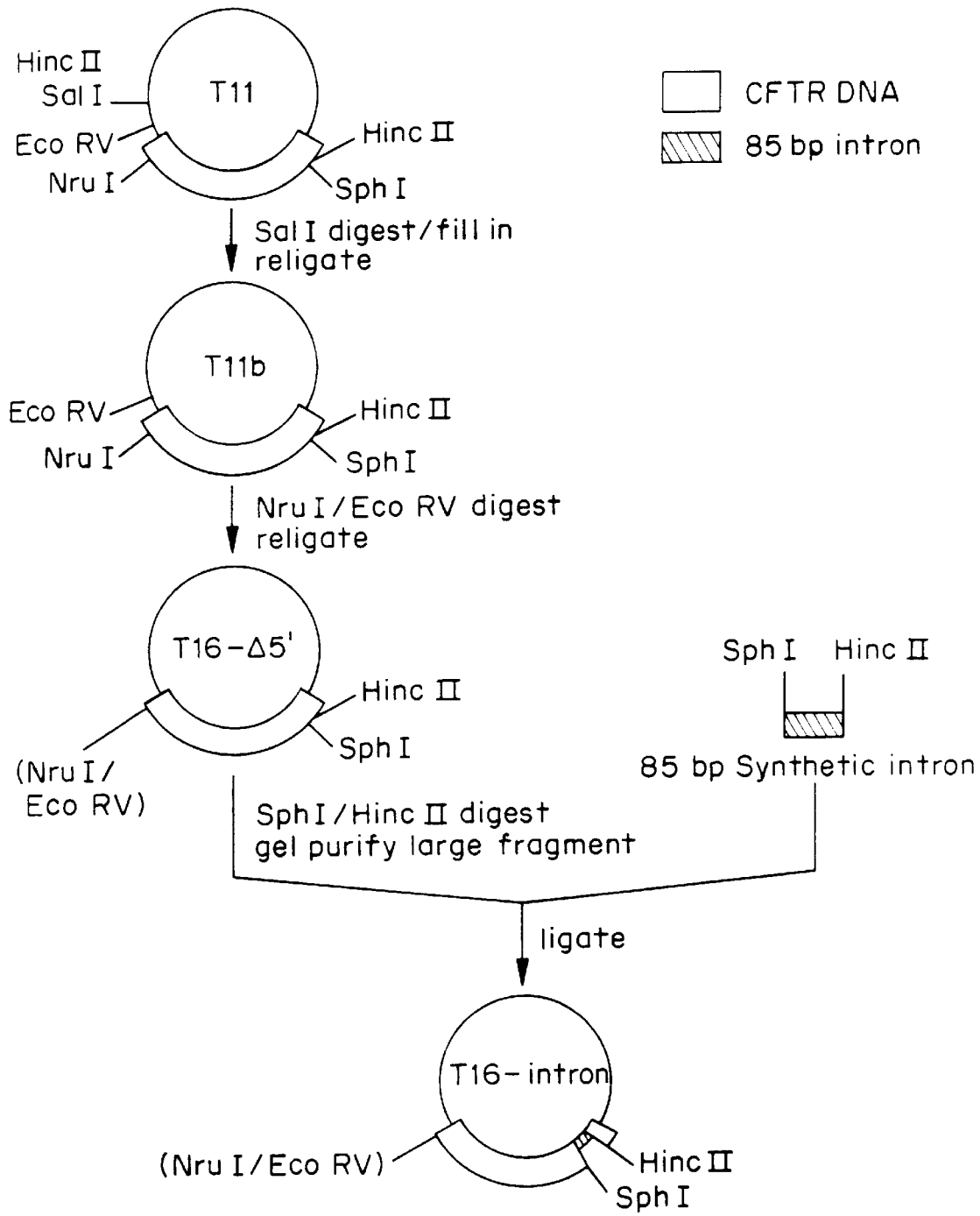
FIGS. 7A and 7B depict plasmid construction of the CFTR cDNA clone pKK-CFTR3.
Figure 7B:
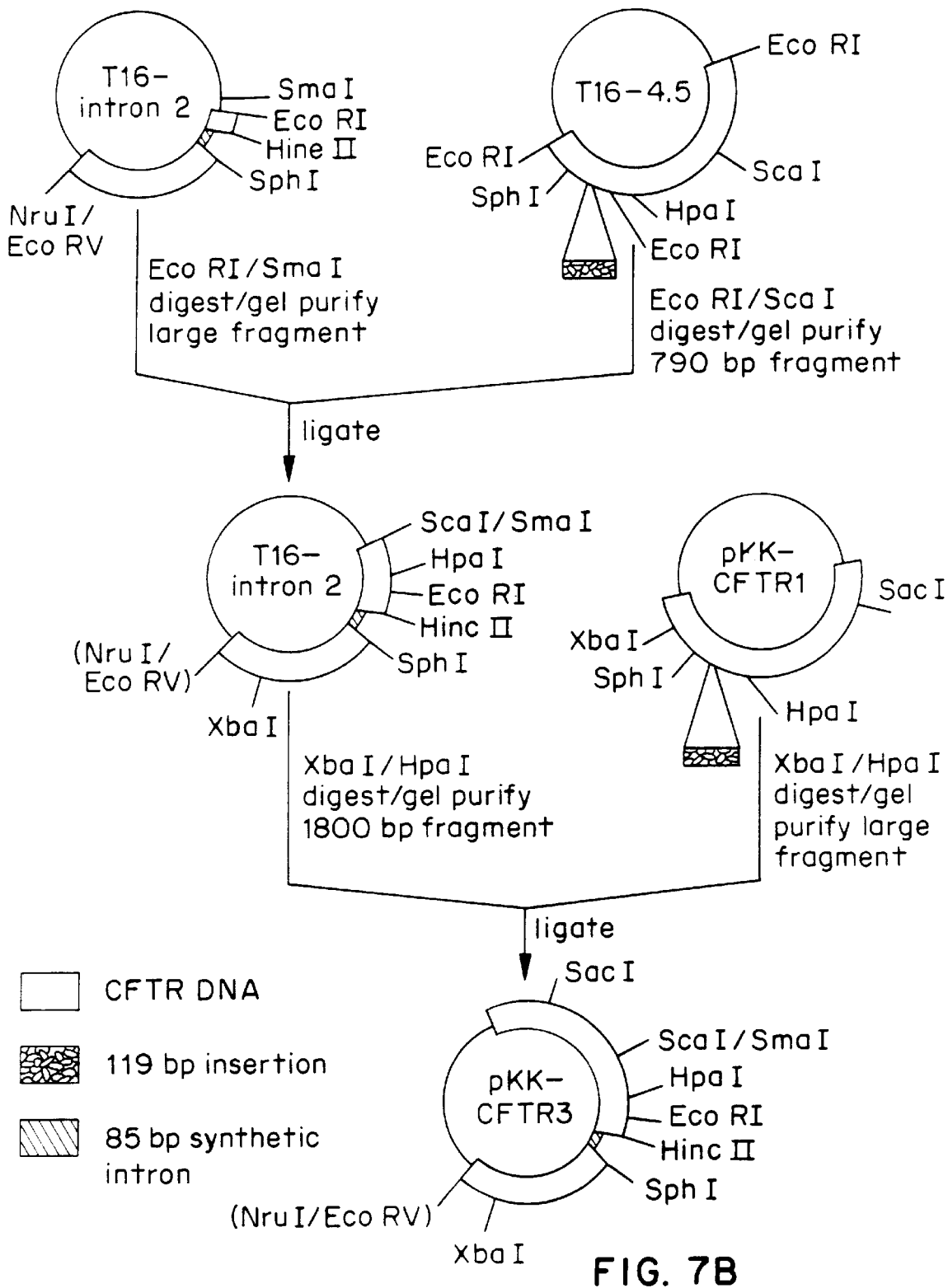

The origin of the materials from which a production lot of the purified Ad2/CFTR-1 is derived was described in detail above and is illustrated as a flow diagram in FIG. 6. All the starting materials from which the purified virus is made (i.e., MCB, and WCB, and the MVSS) will be extensively tested. Further, the growth medium used will be tested and the serum will be from only approved suppliers who will provide test certificates. In this way, all the components used to generate a production lot will have been characterized. Following growth, the production lot virus will be purified by two rounds of CsCl centrifugation, dialyzed, and tested. A production lot should constitute $1-5 \times 10^{10}$ pfu Ad2/CFTR-1.

As described above, to detect any contaminating material aliquots of the production lot will be analyzed by SDS gel electrophoresis and restriction enzyme mapping. However, these tests have limited sensitivity. Indeed, unlike the situation for purified single chain recombinant proteins, it is very difficult to quantitate the purity of the AD2/CFTR-1 using SDS polyacrylamide gel electrophoresis (or similar methods). An alternative is the immunological detection of contaminating proteins (IDCP). Such an assay utilizes antibodies raised against the proteins purified in a mock purification run. Development of such an assay has not yet been attempted for the CsCl purification scheme for Ad2/CFTR-1. However, initially an IDCP assay developed for the detection of contaminants in recombinant proteins produced in Chinese hamster ovary (CHO) cells will be used. In addition, to hamster proteins, these assays detect bovine serum albumin (BSA), transferrin and IgG heavy and light chain derived from the serum added to the growth medium. Tests using such reagents to examine research batches of Ad2/CFTR-1 by both ELISA and Western blots are in progress.

Other proteins contaminating the virus preparation are likely to be from the 293 cells—that is, of human origin. Human proteins contaminating therapeutic agents derived from human sources are usually not problematic. In this case, however, we plan to test the production lot for transforming factors. Such factors could be activities of contaminating human proteins or of the Ad2/CFR-1 vector or other contaminating agents. For the test, it is proposed that 10 dishes of Rat I cells containing $2 \times 10^6$ cells (the number of target cells in the patient) with 4 times the highest human dose of Ad2/CFTR-1 ($2 \times 10^8$ pfu) will be infected. Following infection, the cells will be plated out in agar and examined for the appearance of transformed foci for 2 weeks. Wild type adenovirus will be used as a control.

Nucleic acids and proteins would be expected to be separated from purified virus preparations upon equilibrium density centrifugation. Furthermore, the 293 cells are not expected to contain VL30 sequences. Biologically active nucleic cells should be detected.

Example 8

Preliminary Experiments Testing the Ability of Ad2/Gal Virus to Enter Airway Epithelial Cells a. Hamster Studies Initial studies involving the intratracheal instillation of the Ad-βGal viral vector into Syrian hamsters, which are reported to be permissive for human adenovirus are being performed. The first study, a time course assessment of the pulmonary and systemic acute inflammatory response to a single intratracheal administration of Ad-βGal viral vector, has been completed. In this study, a total of 24 animals distributed among three treatment groups, specifically, 8 vehicle control, 8 low dose virus ($1 \times 10^{11}$ particles; $3 \times 10^8$ pfu), and 8 high dose virus ($1.7 \times 10^{12}$ particles; $5 \times 10^9$ pfu), were used. Within each treatment group, 2 animals were analyzed at each of four time points after viral vector instillation: 6 hrs, 24 hrs, 48 hrs, and 7 days. At the time of sacrifice of each animal, lung lavage and blood samples were taken for analysis. The lungs were fixed and processed for normal light-level histology. Blood and lavage fluid were evaluated for total leukocyte count and leukocyte differential. As an additional measure of the inflammatory process, lavage fluid was also evaluated for total protein. Following embeddings, sectioning and hematoxylin/eosin staining, lung sections were evaluated for signs of inflammation and airway epithelial damage.

With the small sample size, the data from this preliminary study were not amenable to statistical analyses, however, some general trends could be ascertained. In the peripheral blood samples, total leukocyte counts showed no apparent dose- or time- dependent changes. In the blood leukocyte differential counts, there may have been a minor dose-related elevation in percent neutrophil at 6 hours; however, data from all other time points showed no elevation in neutrophil percentages. Taken together, these data suggest little or nor systemic inflammatory response to the viral administration.

From the lung lavage, some elevation in total neutrophil counts were observed at the first three time points (6 hr, 24 hr, 48 hr). By seven days, both total and percent neutrophil values had returned to normal range. The trends in lung lavage protein levels were more difficult to assess due to inter-animal variability; however, no obvious dose- or time-dependent effects were apparent. First, no damage to airway epithelium was observed at any time point or virus dose level. Second, a time- and dose- dependent mild inflammatory response was observed, being maximal at 48 hr in the high virus dose animals. By seven days, the inflammatory response had completely resolved, such that the lungs from animals in all treatment groups were indistinguishable.

In summary, a mild, transient, pulmonary inflammatory response appears to be associated with the intratracheal administration of the described doses of adenoviral vector in the Syrian Hamster.

A second, single intratracheal dose, hamster study has been initiated. This study is designed to assess the possibility of the spread of ineffective viral vectors to organs outside of the lung and the antibody response of the animals to the adenoviral vector. In this study, the three treatment groups (vehicle control, low dose virus, high dose virus) each contained 12 animals. Animals will be evaluated at three time points: I day, 7 days, and 1 month. In this study, viral vector persistence and possible spread will be evaluated by the assessment of the presence of infective virions in numerous organs including lung, gut, heart, liver, spleen, kidney, brain and gonads. Changes in adenoviral antibody titer will be measured in peripheral blood and lung lavage. Additionally, lung lavage, peripheral blood and lung histology will be evaluated as in the previous study.

b. Primate studies

Studies of recombinant adenovirus are also underway in primates. The goal of these studies is to assess the ability of recombinant adenoviral vectors to deliver genes to the respiratory epithelium in vivo and to assess the safety of the construct in primates. Initial studies in primates targeted nasal epithelia as the site of infection because of its similarity to lower airway epithelia, because of its accessibility, and because nasal epithelia was used for the first human studies. The Rhesus monkey (*Macaca mulatta*) has been chosen for studies, because it has a nasal epithelium similar to that of humans.

How expression of CFTR affects the electrolyte transport properties of the nasal epithelium can be studied in patients with cystic fibrosis. But because the primates have normal CFTR function, instead the ability to transfer a reporter gene was assessed. Therefore the Ad—βGal virus was used. The epithelial cell density in the nasal cavity of the Rhesus monkey is estimated to be $2 \times 10^6$ cells/cm (based on an average nasal epithelial cell diameter of 7 μm) and the surface near 25–50 cm². Thus, there are about $5 \times 10^7$ cells in the nasal epithelium of Rhesus monkey. To focus especially on safety, the higher viral doses (20–200 MOI) were used in vivo. Thus doses in the range of $10^9$–$10^{10}$ pfu were used.

In the first pilot study the right nostril of Monkey A was infected with Ad-β-Gal (~1 ml). This viral preparation was purified by CsCl gradient centrifugation and then by gel filtration chromatography one week later. Adenoviruses are typically stable in CsCl at 4° C. for one to two weeks. However, this viral preparation was found to be defective (i.e., it did not produce detectable β-galactosidase activity in the permissive 293 cells). Thus, it was concluded that there was no live viral activity in the material. β-galactosidase activity in nasal epithelial cells from Monkey A was also not detected. Therefore, in the next study, two different preparations of Ad-β-Gal virus: one that was purified on a CsCl gradient and then dialyzed against Tris-buffered saline to remove the CsCl, and a crude unpurified one was used. Titers of Ad-β-Gal viruses were ~$2 \times 10^{10}$ pfu/ml and >$1 \times 10^{13}$ pfu/ml, respectively, and both preparations produced detectable β-galactosidase activity in 293 cells.

Monkeys were anesthetized by intramuscular injection of ketamine (15 mg/kg). One week before administration of virus, the nasal mucosa of each monkey was brushed to establish baseline cell differentials and levels of β-galactosidase. Blood was drawn for baseline determination of cell differentials, blood chemistries, adenovirus antibody titers, and viral cultures. Each monkey was also examined for weight, temperature, appetite, and general health prior to infection.

The entire epithelium of one nasal cavity was used in each monkey. A foley catheter (size 10) was inserted through each nasal cavity into the pharynx, inflated with 2–3 ml of air. and then pulled anteriorly to obtain tight posterior occlusion at the posterior choana. Both nasal cavities were then irrigated with a solution (~5 ml) of 5 mM dithiothreitol plus 0.2 U/ml neuraminidase in phosphate-buffered saline (PBS) for five minutes. This solution was used to dissolve any residual mucus overlaying the epithelia (It was subsequently found that such treatment is not required.) The washing procedure also allowed the determination of whether the balloons were effectively isolating the nasal cavity. The virus (Ad-β-Gal) was then slowly instilled into the right nostril with the posterior balloon inflated. The viral solution remained in contact with the nasal mucosa for 30 minutes. At the end of 30 minutes, the remaining viral solution was removed by suction. The balloons were deflated, the catheters removed, and the monkey allowed to recover from anesthesia. Monkey A received the CsCl-purified virus (~1.5 ml) and Monkey B received the crude virus (~6 ml). (note that this was the second exposure of Monkey A to the recombinant adenovirus).

Both monkeys were followed daily for appearance of the nasal mucosa, conjunctivitis, appetite, activity, and stool consistency. Each monkey was subsequently anesthetized on days 1, 4, 7, 14, and 21 to obtain nasal, pharyngeal, and tracheal cell samples (either by swabs or brushes) as described below. Phlebotomy was performed over the same time course for hematology, ESR, general screen, antibody serology and viral cultures. Stools were collected every week to assess viral cultures.

To obtain nasal epithelial cells from an anesthetized monkey, the nasal mucosa was first impregnated with 5 drops of Afrin (0.05% oxymetazoline hydrochloride, Schering-Plough) and 1 ml of 2% Lidocaine for 5 min. A cytobrush (the kind typically used for Pap smears) was then used to gently rub the mucosa for about 10 seconds. For tracheal brushings, a flexible fiberoptic bronchoscope; a 3 mm cytology brush (Bard) was advanced through the bronchoscope into the trachea, and a small area was brushed for about 10 seconds. This procedure was repeated twice to obtain a total of ~$10^6$ cells/ml. Cells were then collected on slides (approximately $2 \times 10^4$ cells/slide using a Cytospin 3 (Shandon, Pa.)) for subsequent staining (see below).

To determine viral efficacy, nasal, pharyngeal, and tracheal cells were stained for β-galactosidase using X-gal (5 bromo-4chloro-3-indolyl-β-D-galactoside). Cleavage of X-gal by β-galactosidase produces a blue color that can be seen with light microscopy. The Ad-β-gal vector included a nuclear-localization signal (NLS) (from SV40 large T-antigen) at the amino-terminus of the β-galactosidase sequence to direct expression of this protein to the nucleus. Thus, the number of blue nuclei after staining was determined.

RT-PCR (reverse transcriptase-polymerase chain reaction) was also used to determine viral efficacy. This assay indicates the presence of β-galactosidase mRNA in cells obtained by brushings or swabs. PCR primers were used in both the adenovirus sequence and the LacZ sequence to distinguish virally-produced mRNA from endogenous mRNA. PCR was also used to detect the presence of the recombinant adenovirus DNA. Cytospin preparations was used to assess for the presence of virally produced β-galactosidase mRNA in the respiratory epithelial cells using in-situ hybridization. This technique has the advantage of being highly specific and will allow assessment which cells are producing the mRNA.

Whether there was any inflammatory response was assessed by visual inspection of the nasal epithelium and by cytological examination of Wright-stained cells (cytospin). The percentage of neutrophils and lymphocytes were compared to that of the control nostril and to the normal values from, four control monkeys. Systemic repsonses by white blood cell counts, sedimentation rate, and fever were also assessed.

Viral replication at each of the time points was assessed by testing for the presence of live virus in the supernatant of the cell suspension from swabs or brushes. Each supernatant was used to infect (at several dilutions) the virus-sensitive 293 cell line. Cytopathic changes in the 293 cells were monitored for 1 week and then the cells were fixed and stained for β-galactosidase. Cytopathic effects and blue-stained cells indicated the presence of live virus. Positive supernatants will also be subjected to analysis of nonintegrating DNA to identify (confirm) the contributing virus(es).

Antibody titers to type 2 adenovirus and to the recombinant adenovirus were determined by ELISA. Blood/serum analysis was performed using an automated chemistry analyzer Hitachi 737 and an automated hematology analyzer Technicom H6. The blood buffy coat was cultured in A549 cells for wild type adenovirus and was cultured in the permissive 293 cells.

Results: Both monkeys tolerated the procedure well. Daily examination revealed no evidence of coryza, conjunctivitis or diarrhea For both monkeys, the nasal mucosa was mildly erythematous in both the infection side and the control side; this was interpreted as being due to the instrumentation. Appetites and weights were not affected by virus administrated in either monkey. Physical examination on days 1, 4,7, 14 and 21 revealed no evidence of lymphadenopathy, tachypnea, or tachycardia. On day 21, monkey B had a temperature 39.1° C. (normal for Rhesus monkey 38.8° C.) but had no other abnormalities on physical exam or in laboratory data. Monkey A had a slight leukocytosis on day 1 post infection which returned to normal by day 4; the WBC was 4,920 on the day of infection, 8,070 on day 1, and 5,200 on day 4. The ESR did not change after the infection. Electrolytes and transaminases were normal throughout.

Wright stains of cells from nasal brushing were performed on days 4, 7, 14, and 21. They revealed less than 5% neutrophils and lymphocytes. There was no difference between the infected and the control side.

X-Gal stains of the pharyngeal swabs revealed blue-stained cells in both monkeys on days 4, 7, and 14; only a few of the cells had clear nuclear localization of the pigment and some pigment was seen in extracellular debris. On day 7 post infection, X-Gal stains from the right nostril of monkey A, revealed a total of 135 ciliated cells with nuclear-localized blue stain. The control side had only 4 blue cells Monkey B had 2 blue cells from the infected nostril and none from the control side. Blue cells were not seen on day 7, 14, or 21.

RT-PCR on day 3 post infection revealed a band of the correct size that hybridized with a β-Gal probe, consistent with β-Gal mRNA in the samples from Monkey A control nostril and Monkey B infected nostril. On day 7 there was a positive band in the sample from the infected nostril of Monkey A, the same specimen that revealed blue cells.

Fluid from each nostril, the pharynx, and trachea of both monkeys was placed on 293 cells to check for the presence of live virus by cytopathic effect and X-Gal stain. In Monkey A, live virus was detected in both nostrils on day 3 after infection; no live virus was detected at either one or two weeks post-infection. In Monkey B, live virus was detected in both nostrils, pharynx, and trachea on day 3, and only in the infected nostril on day 7 after infection. No live virus was detected 2 weeks after the infection.

c. Human Explant Studies

In a second type of experiment, epithelial cells from a nasal polyp of a CF patient were cultured on permeable filter supports. These cells form an electrically tight epithelial monolayer after several days in culture. Eight days after seeding, the cells were exposed to the Ad2/CFTR virus for 6 hours. Three days later, the short-circuit current (1 sc)

across the monolayer was measured. cAMP agonists did not increase the 1 sc, indicating that there was no change in chloride secretion. However, this defect was corrected after infection with recombinant Ad2/CFTR. Cells infected with Ad2/CFTR (MOI=5; MOI refers to multiplicity of infection; 1 MOI indicates one pfu/cell) express functional CFTR; cAMP agonists stimulated 1 sc, indicating stimulation of Cl$^-$ secretion. Ad2/CFTR also corrected the CF chloride channel defect in CF tracheal epithelial cells. Additional studies indicated that Ad2/CFTR was able to correct the chloride secretory defect without altering the transepithelial electrical resistance; this result indicates that the integrity of the epithelial cells and the tight junctions was not disrupted by infection with Ad2/CFTR Application of 1 MOI of Ad2/CFTR was also found to be sufficient to correct the CF chloride secretory defect The experiments using primary cultures of human airway epithelial cells indicate that the Ad2/CFTR virus is able to enter CF airway epithelial cells and express sufficient CFTR to correct the defect in chloride transport.

Example 9

In Vivo Delivery to and Expression of CFTR in Cotton Rat and Rhesus Monkey Epithelium

MATERIALS AND METHODS

Adenovirus vector

Ad2/CFTR-1 was prepared as described in Example 7. The DNA construct comprises a full length copy of the Ad2 genome of approximately 37.5 kb from which the early region 1 genes (nucleotides 546 to 3497) have been replaced by cDNA for CFTR (nucleotides 123 to 4622 of the published CFTR sequence with 53 additional linker nucleotides). The viral E1a promoter was used for CFTR cDNA. Termination/polyadenylation occurs at the site normally used by the E1b and protein IX transcripts. The recombinant virus E3 region was conserved. The size of the Ad2-CFTR-1 vector is approximately 104.5% that of wild-type adenovirus. The recombinant virus was grown in 293 cells that complement the E1 early viral promoters. The cells were frozen and thawed three times to release the virus and the preparation was purified on a CsCl gradient, then dialyzed against Tris-buffered saline (PBS) to remove the CsCl, as described.

Animals

Rats. Twenty two cotton rats (68 weeks old, weighing between 80–100 g) were used for this study. Rats were anesthetized by inhaled methoxyflurane (Pitman Moore, Inc., Mundelen, Ill.). Virus was applied to the lungs by nasal instillation during inspiration.

Two cotton rat studies were performed. In the first study, seven rats were assigned to a one time pulmonary infection with 100 µl solution containing 4.1×10$^9$ plaque forming units (pfa) of the Ad2/CFTR-1 virus and 3 rats served as controls. One control rat and either two or three experimental rats were sacrificed with methoxyflurane and studies at each of three time points: 4, 11, or 15 days after infection.

The second group of rats was used to test the effect of repeat administration of the recombinant virus. All 12 rats received 2.1×10$^8$pfu of the Ad2/CFTR-1 virus on day 0 and 9 of the rats received a second dose of 3.2×10$^8$ pfu of Ad2/CFTR-1 14 days later. Groups of one control rat and three experimental rats were sacrificed at 3, 7, or 14 days after the second administration of virus. Before necropsy, the trachea was cannulated and brochoaveolar lavage (BAL) was performed with 3 ml aliquots of phosphate-buffered saline. A median sternotomy was performed and the right ventricle cannulated for blood collection. The right lung and trachea were fixed in 4% formaldehyde and the left lung was frozen in liquid nitrogen and kept at ~70° C. for evaluation by immunochemistry, reverse transcriptase polymerase chain reaction (RT-PCR), and viral culture. Other organs were removed and quickly frozen in liquid nitrogen for evaluation by polymerase chain reaction (PCR).

Monkeys. Three female Rhesus monkeys were used for this study; a fourth female monkey was kept in the same room, and was used as control. For application of the virus, the monkeys were anesthetized by intramuscular injection of ketamine (15 mg/kg). The entire epithelium of one nasal cavity in each monkey was used for virus application. A foley catheter (size 10) was inserted through each nasal cavity into the pharynx, the balloon was inflated with 2–3 ml of air, and then pulled anteriorly to obtain a tight occlusion at the posterior choana. The Ad2/CFTR-1 virus was then instilled slowly in the right nostril with the posterior balloon inflated. The viral solution remained in contact with the nasal mucosa for 30 min. The balloons were deflated, the catheters were removed, and the monkeys were allowed to recover from anesthesia. A similar procedure was performed on the left nostril, except that TBS solution was instilled as a control. The monkeys received a total of three doses of the virus over a period of 5 months. The total dose given was 2.5×10$^9$ pfu the first time, 2.3×10$^9$ pfu the second time, and 2.8×10$^9$ pfu the third time. We estimated that the cell density of the nasal epithelia to be 2×10$^6$ cells/cm$^2$ and a surface area of 25 to 50 cm$^2$. This corresponds to a multiplicity of infection (MOI) of approximately 25.

The animals were evaluated 1 week before the first administration of virus, on the day of administration, and on days 1, 3, 6, 13, 21, 27, and 42 days after infection. The second administration of virus occurred on day 55. The monkeys were evaluated on day 55 and then on days 56, 59, 62, 69, 76, 83, 89, 96, 103, and 111. For the third administration, on day 134, only the left nostril was cannulated and exposed to the virus. The control monkey received instillations of PBS instead of virus. Biopsies of the left medial turbinate were carried out on day 135 in one of the infected monkeys, on day 138 on the second infected monkey, and on day 142 on the third infected monkey and on the control monkey.

For evaluations, monkeys were anesthetized by intramuscular injection of ketamine (15 mg/kg). To obtain nasal epithelial cells, the nasal mucosa was first impregnated with 5 drops of Afrin (0.05% oxymetazoline hydrochloride, Schering-Plough) and 1 ml of 2% Lidocaine for 5 minutes. A cytobrush was then used to gently rub the mucosa for about 3 sec. To obtain pharyngeal epithelial swabs, a cotton-tipped applicator was rubbed over the back of the pharynx 2–3 times. The resulting cells were dislodged from brushes or applicators into 2 ml of sterile PBS. Biopsies of the medial turbinate were performed using cupped forceps under direct endoscopic control.

Animals were evaluated daily for evidence of abnormal behavior of physical signs. A record of food and fluid intake was used to assess appetite and general health. Stool consistency was also recorded to check for the possibility of diarrhea. At each of the evaluation time points, we measured rectal temperature, respiratory rate, and heart rate. We visually inspected the nasal mucosa, conjunctivas, and pharynx. The monkeys were also examined for lymphadenopathy.

Venous blood from the monkeys was collected by standard venipuncture technique. Blood/serum analysis was performed in the clinical laboratory of the University of Iowa Hospitals and Clinics using a Hitachi 737 automated chemistry analyzer and a Technicom H6 automated hematology analyzer.

Serology

Sera were obtained and anti-adenoviral antibody titers were measured by an enzyme-linked immunoadsorbant assay (ELISA). For the ELISA, 50 ng/well of filled adenovirus (Lee Biomolecular Research Laboratories, San Diego, Calif.) in 0.1M $NaHCO_3$ were coated on 96 well plates at 4° C. overnight. The test samples at appropriate dilutions were added, starting at a dilution of 1/50. The samples were incubated for 1 hour, the plates washed, and a goat anti-human IgG HRP conjugate (Jackson ImmunoResearch Laboratories, West Grove, Pa.) was added and incubated for 1 hour. The plates were washed and O-Phenylenediamine (Sigma Chemical Co., St. Louis, Mo.) was added for 30 min. at room temperature. The assay was stopped with 4.5M $H_2SO_4$ and read 490 nm on a Molecular Devices microplate reader. The titer was calculated as the product of the reciprocal of the initial dilution and the reciprocal of the dilution in the last well with an OD>0.100.

Neutralizing antibodies measure the ability of the monkey serum to prevent infection of 293 cells by adenovirus. Monkey serum (1:25 dilution) [or nasal washings (1:2 dilutions)] were added in two-fold serial dilutions to a 96 well plate. Adenovirus ($2.5 \times 10^5$ pfu was added and incubated for 1 hour at 37° C. The 293 cells were then added to all wells and the plates were incubated until the serum-free control wells exhibited >95% cytopathic effect. The titer was calculated as the product of the reciprocal of the initial dilution times the reciprocal of the dilution in the last well showing >95% cytopathic effect.

Bronchoalveolar lavage and nasal brushings for cytology

Bronchoalveolar lavage (BAL) was performed by cannulating the trachea with a silastic catheter and injecting 5 ml of PBS. Gentle suction was applied to recover the fluid. The BAL sample was spun at 5000 rpm for 5 min. and cells were resuspended in 293 media at a concentration of $10^6$ cells/ml. Cells were obtained from the monkey's nasal epithelium by gently rubbing the nasal mucosa for about 3 sec. with a cytobrush. The resulting cells were dislodged from the brushes into 2 ml of PBS. Forty microliters of the cell suspension were cytocentrifuged onto slides and stained with Wright's stain. Samples were examined by light microscopy.

Histology of lung sections and nasal biopsies

The right lung of each cotton rat was removed, inflated with 4% formaldehyde, and embedded in paraffin for sectioning. Nasal biopsies from the monkeys were also fixed with 4% formaldehyde. Histologic sections were stained with hematoxylin and eosin (H&E). Sections were reviewed by at least one of the study personnel and by a pathologist who was unaware of the treatment each rat received.

Immunoytochemistry

Pieces of lung and trachea of the cotton rats and nasal biopsies were frozen in liquid nitrogen on O.C.T. compound. Cryosections and paraffin sections of the specimens were used for immunofluorescence rnicroscopy. Cytospin slides of nasal brushings were prepared on gelatin coated slides and fixed with paraformaldehyde. The tissue was permeabilized with Triton X-100, then a pool of monoclonal antibodies to CFTR (M13-1, M14) (Denning, G. M. et al. (1992) J. Clin. Invest. 89:339–349) was added and incubated for 12 hours. The primary antibody was removed and an anti-mouse biotinylated antibody (Biomeda, Foster City, Calif.) was added. After removal of the secondary antibody, streptavidin FITC (Biomeda, Foster City, Calif.) was added and the slides were observed under a laser scanning confocal microscope. Both control animal samples and non-immune IgG stained samples were used as controls.

PCR

PCR was performed on pieces of small bowel, brain, heart, kidney, liver, ovaries, and spleen from cotton rats. Approximately 1 g of the rat organs was mechanically ground and mixed with 50 μl sterile water, boiled for 5 min., and centrifuged. A 5 μl aliquot of the supernatant was removed for further analysis. Monkey nasal brushings suspensions were also used for PCR.

Nested PCR primer sets were designed to selectively amplify Ad2/CFTR-1 DNA over endogenous CFTR by placing one primer from each set in the adenovirus sequence and the other primer in the CFTR sequence. The first primer set amplifies a 723 bp fragment and is shown below:

Ad2 5' ACT CTT GAG TGC CAG CGA GTA GAG TTT TCT CCT CCG 3'(SEQ ID NO:4)

CFTR 5' GCA AAG GAG CGA TCC ACA CGA AAT GTG CC 3'(SEQ ID NO:5)

The nested primer set amplifies a 506 bp fragment and is shown below:

Ad2 5' CTC CTC CGA GCC GCT CCG AGC TAG 3'(SEQ ID NO:6)

CFTR 5' CCA AAA ATG GCT GGG TGT AGG AGC AGT GTC C 3'(SEQ ID NO:7)

A PCR reaction mix containing 10 mM Tris-Cl (pH 8.3), 50 mM KCl, 1.5 mM $MgCl_2$, 0.001% (w/v) gelatin, 400 μM each dNTP, 0.6 μM each primer (first set), and 2.5 units AmpliTaq (Perkin Elmer) was aliquoted into separate tubes. A 5 μl aliquot of each sample prep was then added and the mixture was overlaid with 50 μl of light mineral oil. The samples were processed on a Barnstead/Thermolyne (Dubuque, Iowa) thermal cycler programmed for 1 min. at 94° C., 1 min. at 65° C., and 2 min. at 72° C. for 40 cycles. Post-run dwell was for 7 min. at 72° C. A 5 μl aliquot was removed and added to a second PCR reaction using the nested set of primers and cycled as above. A 10 μl aliquot of the final amplification reaction was analyzed on a 1% agarose gel and visualized with ethidium bromide.

To determine the sensitivity of this procedure, a PCR mix containing control rat liver supernatant was aliquoted into several tubes and spiked with dilutions of Ad2/CFTR-1. Following the amplification protocols described above, it was determined that the nested PCR procedure could detect as little as 50 pfu of viral DNA.

RT-PCR

RT-PCR was used to detect vector-generated mRNA in cotton rat lung tissue and samples from nasal brushings from monkeys. A 200 μl aliquot of guanidine isothiocyanate solution (4M quanidine isothiocyanate 25 mM sodium citrate pH 7.0. 0.5% sarcosvl. and 0.1 M β-mercaptoethanol) was added to a frozen section of each lung and pellet from nasal brushings and the tissue was mechanically ground. Total RNA was isolated utilizing a single-step method (Chomczynski, P. and Sacchi, N. et al. (1987) Analytical Biochemistry 162:156–159; Hanson, C. A. et al. (1990) Am. J. Pathol. 137:1–6). The RNA was incubated with 1 unit RQ1 RNase-free DNase (Promega Corp., Madison Wis.)) at 37° C. for 20 min., denatured at 99° C. for 5 min., precipitated with ammonium acetate and ethanol, and redissolved in 4 μl diethylpyrocarbonate treated water containing 20 units RNase Block 1 (Stratagene, La Jolla Calif.). A 2 μl aliquot of the purified RNA was reverse transcribed using the GeneAmp RNA PCR kit (Perkin Elmer Cetus) and the downstream primer from the first primer set described in the previous section. Reverse transcriptase was omitted from the reaction with the remaining 2 µl of the purified RNA prep, as a control in which preparations (both +/- RT) were then amplified using nested primer sets and the PCR protocols described above. A 10 µl aliquot of the final amplification reaction was analyzed on a 1% agarose gel and visualized with ethidium bromide.

Southern analysis

To verify the identity of the PCR products, Southern analysis was performed. The DNA was transferred to a nylon membrane as described (Sambrook et al.). A fragment of CFTR cDNA (aminoacids #1–525) was labeled with [$^{32}$P]-dCTP (ICN Biomedicals, Inc. Irvine Calif.) using an oligolabeling kit (Pharmacia, Piscataway, N.J.) and purified over a NICK column (Pharmacia Piscataway, N.J.) for use as a hybridization probe. The labeled probe was denatured, cooled, and incubated with the prehybridized filter for 15 hours at 42° C. The hybridized filter was then exposed to film (Kodak XAR-5) for 10 min.

Culture of Ad2/CFTR-1

Viral cultures were performed on the permissive 293 cell line. For culture of virus from lung tissue, 1 g of lung was frozen/thawed 3–6 times and then mechanically disrupted in 200 µl of 293 media For culture of BAL and monkey nasal brushings, the cell suspension was spun for 5 min and the supernatant was collected. Fifty µl of the supernatant was added in duplicate to 293 cells grown in 96 well plates at 50% confluence. The 293 cells were incubated for 72 hr at 37° C., then fixed with a mixture of equal parts of methanol and acetone for 10 min. and incubated with FITC-labeled antiadenovirus monoclonal antibodies (Chemicon, Light Diagnostics, Temecuca, Calif.) for 30 min. Positive nuclear immunofluorescence was interpreted as positive culture. The sensitivity of the assay was evaluated by adding dilutions of Ad2/CFTR-1 to 50 µl of the lung homogenate from one of the control rats. Viral replication was detected when as little as 1 pfu was added.

RESULTS

Efficacy of Ad2/CFTR-1 in the lungs of cotton rats

To test the ability of Ad2/CFTR-1 to transfer CFTR cDNA to the intrapulmonary airway epithelium, several studies were performed. 4×10 pfu—I.U. of Ad2/CFTR-1 in 100 µl s adminstered to seven cotton rats; three control rats received 100 µl of TBS (the vehicle for the virus). The rats were sacrificed 4, 10 or 14 days later. To detect viral transcripts encoding CFTR, reverse transcriptase was used to prepare cDNA from lung homogenates. The cDNA was amplified with PCR using primers that span adenovirus and CFTR-encoded sequences. Thus, the procedure did not detect endogenous rat CFTR. The lungs of animals which received Ad2/CFTR-1 were positive for virally-encoded CFTR mRNA. The lungs of all control rats were negative.

To detect the protein, lung sections were immunostained with antibodies specific to CFTR. CFTR was detected at the apical membrane of bronchial epithelium from all rats exposed to Ad2/CFTR-1, but not from control rats. The location of recombinant CFTR at the apical membrane is consistent with the location of endogenous CFTR in human airway epithelium. Recombinant CFTR was detected above background levels because endogenous levels of CFTR in airway epithelia are very low and thus, difficult to detect by immunocytochemistry (Trapnell, B. et al. (1991) *Proc. Natl. Acad. Sci* USA 88:6565–6569; Denning, G. M. et al. (1992) *J Cell Biol.* 118:551–59).

These results show that Ad2/CFTR-1 directs the expression of CFTR mRNA in the lung of the cotton rat and CFTR protein in the intrapulmonary airways.

Safety of Ad2/CFTR-1 in cotton rats

Because the E1 region of Ad2 is deleted in the Ad2/CFTR-1 virus, the vector was expected to be replication-impaired (Berkner, K. L. (1988) *BioTechniques* 6:616–629) and that it would be unable to shut off host cell protein synthesis (Basuss, L. E. et al. (1989) *J. Virol.* 50:202–212). Previous in vitro studies have suggested that this is the case in a variety of cells including primary cultures of human airway epithelial cells (Rich, D. P. et al. (1993) *Human Gene Therapy* 4:461–476). However, it is important to confirm this in vivo in the cotton rat, which is the most permissive animal model for human adenovirus infection (Ginsberg, H. S. et al. (1989) *Proc. Natl. Acad. Sci* USA 86:3823–3827; Prince, G. A. et al. (1993) *J. Virol.* 67:101–111). Although dose of virus of $4.1 \times 10^{10}$ pfus per kg was used, none of the rats dies. More importantly, extracts from lung homogenates from each of the cotton rats were cultured in the permissive 293 cell line. With this assay 1 pfu of recombinant virus was detected in lung homogenate. However, virus was not detected by culture in the lungs of any of the treated animals. Thus, the virus did not appear to replicate in vivo.

It is also possible that administration of Ad2/CFTR-1 could cause an inflammatory response, either due to a direct effect of the virus or as a result of administration of viral particles. Several studies were performed to test this possibility. None of the rats had a change in the total or differential white blood cell count, suggesting that there was no major systemic inflammatory response. To assess the pulmonary inflammatory response more directly, bronchoalveolar lavage was performed on each of the rats. FIG. 18A shows that there was no change in the total number of cells recovered from the lavage or in the differential cell count.

Sections of the lung stained by H&E were also prepared. There was no evidence of viral inclusions or any other changes characteristic of adenoviral infection (Prince, G. A. et al. (1993) *J. Virol.* 67:101–111). When coded lung sections were evaluated by a skilled reader who was unaware of which sections were treated, she was unable to distinguish between sections from the treated and untreated lungs.

It seemed possible that the recombinant adenovirus could escape from the lung into other tissues. To test for this possibility, other organs from the rats were evaluated using nested PCR to detect viral DNA. All organs tested from infected rats were negative, with the exception of small bowel which was positive in 3 of 7 rats. The presence of viral DNA in the small bowel suggests that the rats may have swallowed some of the virus at the time of instillation or, alternatively, the normal airway clearance mechanisms may have resulted in deposition of viral DNA in the gastrointestinal tract. Despite the presence of viral DNA in homogenates of small intestine, none of the rats developed diarrhea. This result suggests that if the virus expressed CFTR in the intestinal epithelium, there was no obvious adverse consequence.

Repeat administration of Ad2/CFTR-1 to cotton rats

Because adenovirus DNA integration into chromosomal DNA is not necessary for gene expression and only occurs at very low frequency, expression following any given treatments was anticipated to be finite and that repeated administration of recombinant adenovirus would be required for treatment of CF airway disease. Therefore, the effect of repeated administration of Ad2/CFTR-1 cotton rats was examined. Twelve cotton rats received 50 µl of Ad2/CFTR-1. Two weeks later, 9 of the rats received a second dose of 50 µl of Ad2/CFTR-1 and 3 rats received 50 µl of TBS. Rats were sacrificed on day 3, 7, or 14 after virus administration. At the time of the second vector administration all cotton rats had an increased antibody titer to adenovirus.

After the second intrapulmonary administration of virus, none of the rats died. Moreover, the results of studies assessing safety and efficacy were similar to results obtained in animals receiving adenovirus for the first time. Viral cultures of rat lung homogenates on 293 cells were negative at all time points, suggesting that there was no virus replication. There was no difference between treated and control rats in the total or differential white blood count at any of the time points. The lungs were evaluated by histologic. sections stained with H&E; and found no observable differences between the control and treated rats when sections were read by us or by a blinded skilled reader. When organs were examined for viral DNA using PCR, viral DNA was found only in the small intestine of 2 rats. Despite seropositivity of the rats at the time of the second administration, expression of CFTR (as assessed by RT-PCR and by immunocytochemistry of sections stained with CFTR antibodies) similar to that seen in animals that received a single administration was observed.

These results suggest that prior administration of Ad2/CFTR-1 and the development of an antibody response did not cause an inflammatory response in the rats nor did it prevent virus-dependent production of CFTR.

Evidence that Ad2/CFTR-1 expresses CFTR in primate airway epithelium

The cells lining the respiratory tract and the immune system of primates are similar to those of humans. To test the ability of Ad2/CFTR-1 to transfer CFTR to the respiratory epithelium of primates, Ad2/CFTR was applied on three occasions as described in the methods to the nasal epithelium of three Rhesus monkeys. To obtain cells from the respiratory epithelium, the epithelium was brushed using a procedure similar to that used to sample the airway epithelium of humans during fiberoptic bronchoscopy.

To assess gene transfer, RT-PCR was used as described above for the cotton rats. RT —PCR was positive on cells brushed from the right nostril of all three monkeys, although it was only detectable for 18 days after virus administration. An example of the results are shown in FIG. 19A. The presence of a positive reaction in cells from the left nostril most likely represents some virus movement to the left side due to drainage, or possibly from the monkey moving the virus from one nostril to the other with its fingers after it recovered from anesthesia.

The specificity of the RT-PCR is shown in FIG. 23B. A Southern blot with a probe to CFTR hybridized with the RT-PCR product from the monkey infected with Ad2/CFTR-1. As a control, one monkey received a different virus (Ad2/βGal-1) which encodes β-galactosidase. When different primers were used to reverse transcribe the β-galactosidase mRNA and amplify the cDNA, the appropriate PCR product was detected. However, the PCR product did not hybridize to the CFTR probe on Southern blot. This result shows the specificity of the reaction for amplification of the adenovirus-directed CFTR transcript.

The failure to detect evidence of adenovirus-encoded CFTR mRNA at 18 days or beyond suggests that the sensitivity of the RT-PCR may be low because of limited efficacy of the reverse transcriptase or because RNAses may have degraded RNA after cell acquisition. Viral DNA, however, was detected by PCR in brushings from the nasal epithelium for seventy days after application of the virus. This result indicates that although mRNA was not detected after 2 weeks, viral DNA was present for a prolonged period and may have been transcriptionally active.

To assess the presence of CFTR proteins directly, cells obtained by brushing were plated onto slides by cytospin and stained with antibodies to CFTR. A positive reaction was clearly evident in cells exposed to Ad2/CFTR-1. The cells were scored as positive by immunocytochemistry when evaluated by a reader uninformed to the identity of the samples. Immunocytochemistry remained positive for five to six weeks for the three monkeys, even after the second administration of Ad2/CFTR-1. On occasion, a few positive staining cells were observed from the contralateral nostril of the monkeys. However, this was of short duration, lasting at most one week.

Sections of nasal turbinate biopsies obtained within a week after the third infection were also examined. In sections from the control monkey, little if any immunofluorescence from the surface epithelium was observed, but the submucosal glands showed significant staining of CFTR. These observations are consistent with results of previous studies (Engelhardt, J. F. and Wilson, J. M. (1992) Nature Gen. 2:240–248.) In contrast, sections from monkeys that received Ad2/CFTR-1 revealed increased immunofluorescence at the apical membrane of the surface epithelium. The submucosal glands did not appear to have greater immunostraining than was observed under control conditions. These results indicate that Ad2/CFTR-1 can transfer the CFTR cDNA to the airway epithelium of Rhesus monkeys, even in seropositive animals (see below).

Safety of Ad2/CFTR-1 administered to monkeys

FIG. 20 shows that all three treated monkeys developed antibodies against adenovirus. Antibody titers measured by ELISA rose within two weeks after the first infection. With subsequent infections the titer rose within days. The sentinel monkey had low antibody titers throughout the experiment. Tests for the presence of neutralizing antibodies were also performed. After the first administration, neutralizing antibodies were not observed, but they were detected after the second administration and during the third viral administration (FIG. 20).

To detect virus, supernatants from nasal brushings and swabs were cultured on 293 cells. All monkeys had positive cultures on day 1 and on day 3 or 4 from the infected nostril. Cultures remained positive in one of the monkeys at seven days after administration, but cultures were never positive beyond 7 days. Live virus was occasionally detected in swabs from the contra lateral nostril during the first 4 days after infection. The rapid loss of detectable virus suggests that there was not viral replication. Stools were routinely cultured, but virus was never detected in stools from any of the monkeys.

None of the monkeys developed any clinical signs of viral infection or inflammation. Visual inspection of the nasal epithelium revealed slight erythema in all three monkeys in both nostrils on the first day after infection; but similar erythema was observed in the control monkey and likely resulted from the instrumention. There was no visible abnormalities at days 3 or 4, or on weekly inspection thereafter. Physical examination revealed no fever, lymphadenopathy, conjunctivitis, tachypnea, or tachycardia at any of the time points. No abnormalities were found in a complete blood count or sedimentation rate, nor were abnormalities observed in serum electrolytes, transaminases, or blood urea nitrogen and creatinine.

Examination of Wright-stained cells from the nasal brushings showed that neutrophils and lymphocytes accounted for less than 5% of total cells in all three monkeys. Administration of the Ad2/CFTR-1 caused no change in the distribution or number of inflammatory cells at any of the time points following virus administration. H&E stains of the nasal turbinate biopsies specimens from the control monkey could not be differentiated from that of the experimental monkey when the specimens were reviewed by an independent pathologist.

These results demonstrate the ability of a recombinant adenovirus encoding CFTR (Ad2/CFTR-1) to express CFTR cDNA in the airway epithelium of cotton rats and monkeys during repeated administration. They also indicate that application of the virus involves little if any risk. Thus, they suggest that such a vector may be of value in expressing CFTR in the airway epithelium of humans with cystic fibrosis.

Two methods were used to show that Ad2/CFTR-1 expresses CFTR in the airway epithelium of cotton rats and primates: CFTR mRNA was detected using RT-PCR and protein was detected by immunocytochemistry. Duration of expression as assessed immunocytochemically was five to six weeks. Because very little protein is required to generate $Cl^-$ secretion (Welsh, M. J. (1987) *Physiol. Rev.* 67:1143–1184; Trapnell, B. C. et al. (1991) *Proc. Natl. Acad Sci.* USA 88:6565–6569; Denning, G. M. et al. (1992) *J. Cell Biol.* 118:551–559), it is likely that functional expression of CFTR persists substantially longer than the period of time during which CFTR was detected by immunocytochemistry. Support for this evidence comes from two consderations: first, it is very difficult to detect CFTR immuncytochemically in the airway epithelium, yet the expression of an apical membrane $Cl^-$ permeability due to the presence of CFTR $Cl^-$ channels is readily detected. The ability of a minimal amount of CFTR to have important functional effects is likely a result of the fact that a single ion channel conducts a very large number of ions ($10^6$–$10^7$ ions/sec). Thus, ion channels are not usually abundant proteins in epithelia Second, previous work suggests that the defective electrolyte transport of CF epithelia can be corrected when only 6–10% of cells in a CF airway epithelium overexpress wild-type CFTR (Johnson, L. G. et al. (1992) *Nature Gene* 2:21–25). Thus, correction of the biologic defect in CF patients may be possible when only a small percent of the cells express CFTR. This is also consistent with our previous studies in vitro showing that Ad2/CFTR-1 at relatively low multiplicities of infection generated a cAMP-stimulated $Cl^-$ secretory response in CF epithelia (Rich, D. P. et al. (1993) *Human Gene Therapy* 4:461–476).

This study also provides the first comprehensive data on the safety of adenovirus vectors for gene transfer to airway epithelium.—Several aspects of the studies are encouraging. There was no evidence of viral replication, rather infectious viral particles were rapidly cleared from both cotton rats and primates. These data, together with our previous in vitro studies, suggest that replication of recombinant virus in humans will likely not be a problem. The other major consideration for safety of an adenovirus vector in the treatment of CF is the possibility of an inflammatory response. The data indicate that the virus generated an antibody response in both cotton rats and monkeys. Despite this, no evidence of a systemic or local inflammatory response was observed. The cells obtained by bronchoalveolar lavage and by brushing and swabs were not altered by virus application. Moreover, the histology of epithelia treated with adenovirus was indistinguishable from that of control epithelia. These data suggest that at least three sequential exposures of airway epithelium to adenovirus does not cause a detrimental inflammatory response.

These data suggest that Ad2/CFTR-1 can effectively transfer CFTR cDNA to airway epithelium and direct the expression of CFTR. They also suggest that transfer is relatively safe in animals. Thus, they suggest that Ad2/CFTR-1 may be a good vector for treating patients with CF. This was confirmed in the following example.

Example 10

CFTR Gene Therapy in Nasal Epithelia from Human CF Subjects

EXPERIMENTAL PROCEDURES

Adenovirus vector. The recombinant adenovirus Ad2/CFTR-1 was used to deliver CFTR cDNA. The construction and preparation of Ad2/CFTR-1, and its use in vitro and in vivo in animals, has been previously described (Rich, D. P. et al. (1993) *Human Gene Therapy* 4:461–476; Zabner, J. et al. (1993) *Nature Gen.* (in press)). The DNA construct comprises a full length copy of the Ad2 genome from which the early region 1 genes (nucleotides 546 to 3497) have been replaced by cDNA for CFTR. The viral E1a promoter was used for CFTR cDNA; this is a low to moderate strength promoter. Termination/polyadenylation occurs at the site normally used by E1b and protein IX transcripts. The E3 region of the virus was conserved.

Patients

Three patients with CF were studied. Genotype was determined by IG Labs (Framingham, Mass.). All three patients had mild CF as defined by an NIH score >70 (Taussig, L. M. et al. (1973) *J Pediatr.* 82:380–390), a normal weight for height ratio, a forced expiratory volume in one second (FEV1) greater than 50% of predicted and an arterial $PO_2$ greater than 72. All patients were seropositive for type 2 adenovirus, and had no recent viral illnesses. Pretreatment cultures of nasal swabs, pharyngeal swabs, sputum, urine, stool, and blood leukocytes were negative for adenovirus. PCR of pretreatment nasal brushings using primers for the adenovirus E1 region were negative. Patients were evaluated at least twice by FEV1, cytology of nasal mucosa, visual inspection, and measurement of Vt before treatment. Prior to treatment, a coronal computed tomographic scan of the paranasal sinuses and a chest X-ray were obtained.

The first patient was a 21 year old woman who was diagnosed at 3 months after birth. She had pancreatic insufficiency, a positive sweat chloride test (101 mEq/1), and is homoygous for the ΔF508 mutation. Her NIH score was 90 and her FEV1 was 83% predicted. The second patient is a 36 year old man who was diagnosed at the age of 13 when he presented with symptoms of pancreatic insufficiency. A sweat chloride test revealed a chloride concentration of 70 mEq/1. He is a heteroygote with the ΔF508 and G55ID mutations. His NIH score was 88 and his FEV1 was 66% predicted. The third patient is a 50 year old woman, diagnosed at the age of 9 with a positive sweat chloride test (104 mEq/1). She has pancreatic insufficiency and insulin dependent diabetes mellitus. She is homozygous for the ΔF508 mutation. Her NIH score was 73 and her FEV1 was 65% predicted.

Transepithelial voltage

The transepithelial electric potential difference across the nasal epithelium was measured using techniques similar to those previously described (Alton, E. W. F. W. et al (1987) *Thorax* 42:815–817; Knowles, M. et al. (1981) *N. Eng. J Med.* 305:1489–1495). A 23 gauge subcutaneous needle connected with sterile normal saline solution to a silver/silver chloride pellet (E. W. Wright, Guilford, Conn.) was used as a reference electrode. The exploring electrode was a size 8 rubber catheter (modified Argyle[R] Foley catheter, St. Louis, Mo.) with one side hole at the tip. The catheter was filled with Ringer's solution containing (in mM), 135 NaCl, 2.4 $KH_2PO_2$, $K_2HPO_4$, $1.2 CaCL_2$, 1.2 $MgCl_2$ and 10 Hepes (titrated to pH 7.4 with NaOH) and was connected to a silver/silver chloride pellet. Voltage was measured with a voltmeter (Keithley Instruments Inc., Cleveland, Ohio) connected to a strip chart recorder (Servocorder, Watanabe Instruments, Japan). Prior to the measurements, the silver/silver chloride pellets were connected in series with the Ringer's solution; the pellets were changed if the recorded Vt was greater than ±4 mV. The rubber catheter was introduced into the nostril under telescopic guidance (Hopkins Telescope, Karl Storz, Tuttlingen West Germany) and the side hole of the catheter was placed next to the study area in the medical aspect of the inferior nasal turbinate. The distance from the anterior tip of the inferior turbinate and the spatial relationship with the medial turbinate, the maxillary sinus ostium, and in one patient a small polyp, were used to locate the area of Ad2/CFTR-1 administration for measurements; Photographs and video recorder images were also used. Basal Vt was recorded until no changes in Vt were observed after slow intermittent 100 $\mu$l/min infusion of the Ringer's solution. Once a stable baseline was achieved, 200 $\mu$l of a Ringer's solution containing 100 $\mu$M amiloride (Merck and Co. Inc., West Point, Pa.) was instilled through the catheter and changes in Vt were recorded until no further change were observed after intermittent instillations. Finally, 200 $\mu$l Ringer's solution containing 100 $\mu$M amiloride plus 10 $\mu$M terbutaline (Geigy Pharmaceuticals, Ardsley, N.Y.) was instilled and the changes in Vt were recorded.

Measurements of basal Vt were reproducible over time: in the three treated patients, the coefficients of variation before administration of Ad2/CFTR-1 were 3.6%, 12%, and 12%. The changes induced by terbutaline were also reproducible. In 30 measurements in 9 CF patients, the terbutaline-induced changes in Vt ($\Delta$Vt) ranged from 0 mV to +4 mV; hyperpolarization of Vt was never observed. In contrast, in 7 normal subjects $\Delta$Vt ranged from $-1$ mV to $-5$ mV; hyperpolarization was always observed.

Ad2/CFTR-1 application and cell acquisition.

The patients were taken to the operating room and monitoring was commenced using continuous EKG and pulse oximetry recording as well as automatic intermittent blood pressure measurement. After mild sedation, the nasal mucosa was anesthetized by atomizing 0.5 ml of 5% cocaine. The mucosa in the area of the inferior turbinate was then packed with cotton pledgets previously soaked in a mixture of 2 ml of 0.1% adrenaline and 8 ml of 1% tetracaine. The pledgets remained in place for 1040 min. Using endoscopic visualization with a television monitoring system, the applicator was introduced through the nostril and positioned on the medial aspect of the inferior turbinate, at least three centimeters from its anterior tip (FIGS. 21A–21I). The viral suspension was infused into the applicator through connecting catheters. The position of the applicator was monitored endoscopically to ensure that it did not move and that enough pressure was applied to prevent leakage. After the virus was in contact with the nasal epithelium for thirty minutes, the viral suspension was removed, and the applicator was withdrawn. In the third patient's right nasal cavity, the virus was applied using the modified Foley catheter used for Vt measurements. The catheter was introduced without anesthetic under endoscopic guidance until the side hole of the catheter was in contact with the area of interest in the inferior turbinate. The viral solution was infused slowly until a drop of solution was seen with the telescope. The catheter was left in place for thirty minutes and then removed.

Cells were obtained from the area of virus administration approximately 2 weeks before treatment and then at weekly intervals after treatment. The inferior turbinate was packed for 10 minutes with cotton pledgets previously soaked in 1 ml of 5% cocaine. Under endoscopic control, the area of administration was gently brushed for 5 seconds. The brushed cells were dislodged in PBS. Swabs of the nasal epithelia were collected using cotton tipped applicators without anesthesia. Cytospin slides were prepared and stained with Wright's—stain. Light microscopy was used to assess the respiratory epithelial cells and inflammatory cells. For biopsies, sedatives/anesthesia was administered as described for the application prodcure. After endosconic inspection and identification of the site to be biopsied the submucosa was injected with 1% xylocaine, with 1/100,000 epinephrine. The area of virus application on the inferior turbinate was removed. The specimen was fixed in 4% formaldehyde and stained.

RESULTS

On day one after Ad2/CFTR-1 administration and at all subsequent time points, Ad2/CFTR-1 from the nasal epithelium, pharynx, blood, urine, or stool could not be cultured. As a control for the sensitivity of the culture assay, samples were routinely spiked with 10 and 100 I.U. Ad2/CFTR- 1. In every case, the spiked samples were positive, indicating that, at a minimum, 10 I.U. of Ad/CFTR should have been detected. No evidence of a systemic response as assessed by history, physical examination, serum chemistries or cell counts, chest and sinus X-rays, pulmonary function tests, or arterial blood gases performed before and after Ad2/CFTR-1 administration. An increase in antibodies to adenovirus was not detectable by ELISA or by neutralization for 35 days after treatment.

Three to four hours after Ad2/CFTR-1 administration, at the time that local anesthesia and localized vasoconstriction abated, all patients began to complain of nasal congestion and in one case, mild rhinorrhea. These were isolated symptoms that diminished by 18 hours and resolved by 28 to 42 hours. Inspection of the nasal mucosa showed mild to moderate erythema, edema, and exudate (FIGS. 21A–21C). These physical findings followed a time course similar to the symptoms. The physical findings were not limited to the site of virus application, even though preliminary studies using the applicator showed that marker methylene blue was limited to the area of application. In two additional patients with CF, the identical anesthesia and application procedure were used, but saline was applied instead of virus, yet the same symptoms and physical findings were observed in these patients (FIGS. 21G–21I). Moreover, the local anesthesia and vasoconstriction generated similar changes even when the applicator was not used, suggesting that the anesthesia/vasoconstriction caused some, if not all the injury. Twenty-four hours after the application procedure, analysis of cells removed from nasal swabs revealed an equivalent increase in the percent neutrophils in patients treated with Ad2/CFTR-1 or with saline. One week after application, the neutrophilia had resolved in both groups. Respiratory epithelial cells obtained by nasal brushing appeared normal at one week and at subsequent time points, and showed no evidence of inclusion bodies. To further evaluate the mucosa, the epithelium was biopsied on day three in the first patient and day one in the second patient. Independent evaluation by two pathologists not otherwise associated with the study suggested changes consistent with mild trauma and possible ischemia (probably secondary to the anesthetic/vasoconstrictors used before virus administration), but there were no abnormalities suggestive of virus-mediated damage.

Because the application procedure produced some mild injury in the first two patients, the method of administration was altered in the third patient. The method used did not require the use of local anesthesia or vasoconstriction and which was thus less likely to cause injury, but which was also less certain in its ability to constrain Ad2/CFTR-1 in a precisely defined area. On the right side, Ad2/CFTR-1 was administered as in the first two patients, and on the left side, the virus was administered without anesthesia or the applicator, instead using a small Foley catheter to apply and maintain Ad2/CFTR-1 in a relatively defined area by surface tension (FIG. 21E). On the right side, the symptoms and physical findings were the same as those observed in the first two patients. By contrast, on the left side there were no symptoms and on inspection the nasal mucosa appeared normal (FIGS. 21D–21F). Nasal swabs obtained from the right side showed neutrophilia similar to that observed in the first two patients. In contrast, the left side which had no anesthesia and minimal manipulation, did not develop neutrophilia Biopsy of the left side on day 3 after administration (FIG. 22), showed morphology consistent with CF—a thickened basement membrane and occasional polymorphonuclear cells in the submucosa—but no abnormalities that could be attributed to the adenovirus vector.

The first patient developed symptoms of a sore throat and increased cough that began three weeks after treatment and persisted for two days. Six weeks after treatment she developed an exacerbation of her bronchitis/bronchiectasis and hemoptysis that required hospitalization. The second patient had a transient episode of minimal hemoptysis three weeks after treatment; it was not accompanied by any other symptoms before or after the episode. The third patient has an exacerbation of bronchitis three weeks after treatment for which she was given oral antibiotics. Based on each patient's pretreatment clinical history, evaluation of the episodes, and viral cultures, no evidence could be discerned that linked these episodes to administration of Ad2/CFTR-1. Rather the episodes appeared consistent with the normal course of disease in each individual.

The loss of CFTR $Cl^-$ channel function causes abnormal ion transport across affected epithelia, which in turn contributes to the pathogenesis of CF-associated airway disease (Boat, T. F. et al. in The Metabolic Basis of Inherited Diseases (Scriver, C. R. et al. eds., McGraw-Hill, New York (1989); Quinton, P. M. (1990) FASEBJ 4:2709–2717). In airway epithelia, ion transport is dominated by two electrically conductive processes: amiloride-sensitive absorption of $Na^+$ from the mucosal to the submucosal surface and cAMP-stimulated $Cl^-$ secretion in the opposite direction. (Quinton, P. M. (1990) FASEB J 4:2709–2717; Welsh, M. J. (1987) *Physio. Rev.* 67:1143–1184). These two transport processes can be assessed noninvasively by measuring the voltage across the nasal epithelium (Vt) in vivo (Knowles, M. et al (1981) *N. Eng. J. Med.* 305:1489–1495; Alton, E. W. F. W. et al.(1987) *Thorax* 42:815–817). FIG. 23 shows an example from a normal subject. Under basal conditions, Vt was electrically negative (lumen referenced to the submucosal surface). Perfusion of amiloride (100 $\mu$M) onto the mucosal surface inhibited Vt by blocking apical $Na^+$ channels (Knowles, M. et al (1981) *N. Eng. J. Med.* 305:1489–1495; Quinton, P. M. (1990) *FAVEB J.* 4:2709–2717: Welsh. M. J. (1992) *Neuron* 8:821–829). Subsequent perfusion of with terbutaline (10 $\mu$M) a β-adrenergic agonist, hyperpolarized Vt by increasing cellular levels of cAMP, opening CFTR $Cl^-$ channels, and stimulating chloride secretion (Quinton, P. M. (1990) FASEB J 4:2709–2717; Welsh, M. J. et al. (1992) *Neuron* 8:821–829). FIG. 24A shows results from seven normal subjects: basal Vt was $-10.5\pm1.0$ mV, and in the presence of amiloride, terbutaline hyperpolarized Vt by $-2.3\pm0.5$ mV.

In patients with CF, Vt was more electrically negative than in normal subjects (FIG. 24B), as has been previously reported (Knowles, M. et al. (1981) *N. Eng. J. Med.* 305:1489–1495). Basal Vt was $-37.0\pm2.4$ mV, much more negative than values in normal subjects (P<0.001). (Note the difference in scale in FIG. 24A and FIG. 24B). Amiloride inhibited Vt, as it did in normal subjects. However, Vt failed to hyperpolarize when terbutaline was perfused onto the epithelium in the presence of amiloride. Instead, Vt either did not change or became less negative: on average Vt depolarized by $+1.8\pm0.6$ mV, a result very different from that observed in normal subjects. (P<0.001).

After Ad2/CFTR-1 was applied, basal Vt became less negative in all three CF patients: FIG. 25A shows an example from the third patient before (FIG. 25A) and after (FIG. 25B) treatment and FIGS. 26A, 26C, and 26E show the time course of changes in basal Vt for all three patients. The decrease in basal Vt suggests that application of Ad2/CFTR-1 corrected the CF electolyte transport defect in nasal epithelium of all three patients. Additional evidence came from an examination of the response to terbutaline. FIG. 25B shows that in contrast to the response before Ad2/CFTR-1 was applied, after virus replication, in the presence of amiloride, terbutaline stimulated Vt. FIGS. 26B, 26D, and 26F show the time course of the response. These data indicate that Ad2/CFTR-1 corrected the CF defect in $Cl^-$ transport. Correction of the $Cl^-$ transport defect cannot be attributed to the anesthesia/application procedure because it did not occur in patients treated with saline instead of Ad2/CFTR-1 (FIG. 27). Moreover, the effects of the anesthesia were generalized on the nasal mucosa, but basal Vt decreased only in the area of virus administration. Finally, similar changes were observed in the left nasal mucosa of the third patient (FIGS. 26E and 26F), which had no symptomatic or physical response after the modified application procedure.

Unsuccessful attempts were made to detect CFTR transcripts by reverse transciptase-PCR and by immunocytochemistry in cells from nasal brushings and biopsies. Although similar studies in animals have been successful (Zabner, J. et al. (1993) *Nature Gen.* (in press)), those studies used much higher doses of Ad2/CFTR-1. The lack of success in the present case likely reflects the small amount of available tissue, the low MOI, the fact that only a fraction of cells may have been corrected, and the fact that Ad2/CFTR-1 contains a low to moderate strength promoter (E1a) which produces much less mRNA and protein than comparable constructs using a much stronger CMV promoter (unpublished observation). The E1a promoter was chosen because CFTR normally expressed at very low levels in airway epithelial cells (Trapnell B. C. et al (1991) *Proc. Natl. Acad Sci.* USA 88:6565–6569). It is also difficult to detect CFTR protein and mRNA in normal human airway epithelia, although function is readily detected because a single ion channel can conduct a very large number of ions per second and thus efficiently support $Cl^-$ transport.

With time, the electrical changes that indicate correction of the CF defect reverted toward pretreatment values. However, the basal Vt appeared to revert more slowly than did the change in Vt produced by terbutaline. The significance of this difference is unknown, but it may reflect the relative sensitivity of the two measurements to expression of normal CFTR. In any case, this study was not designed to test the duration of correction because the treated area was removed by biopsy on one side and the nasal mucosa on the other side was brushed to obtain cells for analysis at 7 to 10 days after virus administration, and then at approximately weekly intervals. Brushing the mucosa removes cells, disrupts the epithelium, and reduces basal Vt to zero for at least two days afterwards, thus preventing an accurate assessment of duration of the effect of Ad2/CFTR-1.

Efficacy of adenovirus-mediated gene transfer

The major conclusion of this study is that in vivo application of a recombinant adenovirus encoding CFTR can correct the defect in airway epithelial Cl⁻ transport that is characteristic of CF epithelia.

Complementation of the Cl⁻ channel defect in human nasal epithelium could be measured as a change in basal voltage and as a change in the response to cAMP agonists. Although the protocol was not designed to establish duration, changes in these parameters were detected for at least three weeks. These results represent the first report that administration of a recombinant adenovirus to humans can correct a genetic lesion as measured by a functional assay. This study contrasts with most earlier attempts at gene transfer to humans, in that a recombinant viral vector was administered directly to humans, rather than using a in vitro protocol involving removal of cells from the patient, transduction of the cells in culture, followed by reintroduction of the cells into the patient.

Evidence that the CF Cl⁻ transport defect was corrected at all three doses of virus, corresponding to 1, 3, and 25 MOI, was obtained. This result is consistent with earlier studies showing that similar MOIs reversed the CF fluid and electrolyte transport defects in primary cultures of CF airway cells grown as epithelia on permeable filter supports (Rich, D. P. et al. (1993) *Human Gene Therapy* 4:461–476 and Zabner et al. submitted for publication): at an MOI of less than 1, cAMP-stimulated Cl⁻ secretion was partially restored, and after treatment with 1 MOI Ad2/CFTR-1 cAMP agonists stimulated fluid secretion that was within the range observed in epithelia from normal subjects. At an MOI of 1, a related adenovirus vector produced β-galactosidase activity in 20% of infected epithelial cells as assessed by fluorescence-activated cell analysis (Zabner et al. submitted for publication). Such data would imply that pharmacologic dose of adenovirus in CF airways might correspond to an MOI of one. If it is estimated that there are $2\times10^6$ cells/cm² in the airway (Mariassy, A. T. in Comparative Biology of the Normal Lung (CRC Press, Boca Raton 1992), and that the airways from the trachea to the respiratory bronchioles have a surface area of 1400 cm² (Weibel, E. R. Morphometry of the Human Lung (Springer Verlag, Heidelberg, 1963) then there would be approximately $3\times10^9$ potential target cells. Assuming a particle to L.U. ratio of 100, this would correspond to approximately $3\times10^{11}$ particles of adenovirus with a mass of approximately 75 µg. While obviously only a crude estimate, such information is useful in designing animal experiments to establish the likely safety profile of a human dose.

It is possible that an efficacious MOI of recombinant adenovirus could be less than the lowest MOI tested here. Some evidence suggests that not all cells in an epithelial monolayer need to express CFTR to correct the CF electrolyte transport defects. Mixing experiments showed that when perhaps 5–10% of cells overexpress CFTR, the monolayer exhibits wild-type electrical properties (Johnson, L. G. et al. (1992) *Nature Gen.* 2:21–25). Studies using liposomes to express CFTR in mice bearing a disrupted CFTR gene also suggest that only a small proportion of cells need to be corrected (Hyde, S. C. et al. (1993) *Nature* 362:250–255). The results referred to above using airway epithelial monolayers and multiplicities of Ad2/CFTR-1 as low as 0.1 showed measurable changes in Cl⁻ secretion (Rich, D. P. et al. (1993) *Human Gene Therapy* 4:461476 and Zabner et al. submitted for publication).

Given the very high sensitivity of electrolyte transport assays (which result because a single Cl⁻ channel is capable of transporting large numbers of ions/sec) and the low activity of the E1a promoter used to transcribe CFTR, the inability to detect CFTR protein and CFTR mRNA are perhaps not surprising. Although CFTR mRNA could not be detected by reverse transcriptase-PCR, Ad2/CFTR-1 DNA could be detected in the samples by standard PCR, demonstrating the presence of input DNA and suggesting that the reverse transcriptase reaction may have been suboptimal. This could have occurred because of factors in the tissue that inhibit the reverse transcriptase. Although there is little doubt that the changes in electrolyte transport measured here result from expression of CFTR, it remains to be seen whether this will lead to measurable clinical changes in lung function.

Safety considerations

Application of the adenovirus vector to the nasal epithelium in these three patients was well-tolerated. Although mild inflammation was observed in the nasal epithelium of all three patients following administration of Ad2/CFTR-1, similar changes were observed in two volunteers who underwent a sham procedure using saline rather than the viral vector. Clearly a combination of anesthetic- and procedure-related trauma resulted in the changes in the nasal mucosa. There is insufficient evidence to conclude that no inflammation results from virus administration. However, using a modified administration of the highest MOI of virus tested (25 MOI) in one patient, no inflammation was observed under conditions that resulted in evidence of biophysical efficacy that lasted until the area was removed by biopsy at three days.

There was no evidence of replication of Ad2/CFTR-1. Earlier studies had established that replication of Ad2/CFTR-1 in tissue culture and experimental animals is severely impaired (Rich, D. P. et al. (1993) *Human Gene Therapy* 4:461476; Zabner, J. et al. (1993) *Nature Gen.* (in press)). Replication only occurs in cells that supply the missing early proteins of the E1 region of adenovirus, such as 293 cells, or under conditions where the E1 region is provided by coinfection with or recombination with an E1-containing adenovirus (Graham, F. L. and Prevec, L, Vaccines: New Approaches to Immunological Problems (R. W. Ellis, ed., Boston, Butterworth-Heinermann, 1992); Berkner, K. L. (1988) *Biotechniques* 6:616–629). The patients studied here where seropositive for adenovirus types 2 and 5 prior to the study were negative for adenovirus upon culture of nasal swabs prior to administration of Ad2/CFTR-1, and were shown by PCR methods to lack endogenous E1 DNA sequences such as have been reported in some human subjects (Matsuse T. et al. (1992) *Am. Rev. Respir. Dis.* 146:177–184).

Example 11

Construction and Packaging of Pseudo Adenoviral Vector (PAV)

With reference to FIG. 16, the PAV construct was made by inserting the Ad2 packaging signal and E1 enhancer region (0-358 nt) in Bluescript II SK- (Stratagene, LaJolla, Calif.). A variation of this vector, known as PAV II was constructed similarly, except the Ad2 packaging signal and E1 enhancer region contained 0-380 nt. The addition of nucleotides at the 5' end results in larger PAVs, which may be more efficiently packaged, yet would include more adenoviral sequences and therefore could potentially be more immunogenic or more capable of replicating.

To allow ease of manipulation for either the insertion of gene coding regions or complete excision and use in transfections for the purpose of generating infectious particles, a complementary plasmid was also built in p Bluescript SKII-. This complementary plasmid contains the Ad2 major late promoter (MLP) and tripartite leader (TPL) DNA and an SV40 T-antigen nuclear localization signal (NLS) and polyadenylation signal (SVpA). As can be seen in FIG. 16, this plasmid contains a convenient restriction site for the insertion of genes of interest between the MLP/TPL and SV40 poly A. This construct is engineered such that the entire cassette may be excised and inserted into the former PAV I or PAV II construct.

Generation of PAV infectious particles was performed by excision of PAV from the plasmid with the Apa I and Sac II restriction endonucleases and co-transfection into 293 cells (an E1a/E1b expressing cell line) (Graham, F. L. et al, (1977) *J. Gen Virol* 36:59–74) with either wild-type Ad2, or packaging/replication deficient helper virus. Purification of PAV from helper can be accompanied by CsCl gradient isolation as PAV viral particles will be of a lower density and will band at a higher position in the gradient.

For gene therapy, it is desirable to generate significant quantities of PAV virion free from contaminating helper virus. The primary advantage of PAV over standard adenoviral vectors is the ability to package large DNA inserts into virion (up to about 36 kb). However, PAV requires a helper virus for replication and packaging and this helper virus will be the predominant species in any PAV preparation. To increase the proportion of PAV in viral preparation several approaches can be employed. For example, one can use a helper virus which is partially defective for packaging into virions (either by virtue of mutations in the packaging sequences (Grable, M. and Hearing P. (1992) *J. Virol.* 66: 723–731)) or by virtue of its size -viruses with genome sizes greater than approximately 37.5 kb package inefficiently. In mixed infections with packaging defective virus, PAV would be expected to be represented at higher levels in the virus mixture than would occur with non-packaging defective helper viruses.

Another approach is to make the helper virus dependent upon PAV for its own replication. This may most easily be accomplished by deleting an essential gene from the helper virus (e.g. IX or a terminal protein) and placing that gene in the PAV vector. In this way neither PAV nor the helper virus is capable of independent replication—PAV and the helper virus are therefore co-dependent. This should result in higher PAV representation in the resulting virus preparation.

A third approach is to develop a novel packaging cell line, which is capable of generating significant quantities of PAV virion free from contaminating helper virus. A novel protein IX, (pIX) packaging system has been developed. This system exploits several documented features of adenovirus molecular biology. The first is that adenoviral defective particles are known to comprise up to 30% or more of standard wild-type adenoviral preparations. These defective or incomplete particles are stable and contain 15–95% of the adenoviral genome, typically 15–30%. Packaging of a PAV genome (15–30% of wild-type genome) should package comparably. Secondly, stable packaging of full-length Ad genome but not genomes <95% required the presence of the adenoviral gene designated pIX.

The novel packaging system is based on the generation of an Ad protein pIX expressing 293 cell line. In addition, an adenoviral helper virus engineered such that the E1 region is deleted but enough exogenous material is inserted to equal or slightly exceed the full length 36 kb size. Both of these two constructs would be introduced into the 293/pIX cell line as purified DNA. In the presence of pIX, yields of both predicted progeny viruses as seen in current PAV/Ad2 production experiments can be obtained. Virus containing lysates from these cells can then be titered independently (for the marker gene activity specific to either vector) and used to infect standard 293 (lacking pIX) at a multiplicity of infection of 1 relative to PAV. Since research with this line as well as from incomplete or defective particle research indicates that full length genomes have a competitive packaging advantage, it is expected that infection with an MOI of 1 relative to PAV will necessarily equate to an effective MOI for helper of greater than 1. All cells will presumably contain both PAV (at least 1) and helper (greater than 1). Replication and viral capsid production in this cell should occur normally but only PAV genomes should be packaged. Harvesting these 93/pIX cultures is expected to yield essentially helper-free PAV.

Example 12

Construction of Ad2-E4/ORF 6

Ad2-E4/ORF6 (FIG. 17 shows the plasmid construction of Ad2-E4/ORF6) is an adenovirus 2 based vector deleted for all Ad2 sequences between nucleotide 32815 and 35577. This deletion removes all open reading frames of E4 but leaves the E4 promoter and first 32–37 nucleotides of the E4 mRNA intact. In place of the deleted sequences, a DNA fragment encoding ORF6 (Ad2 nucleotides 34082–33178) which was derived by polymerase chain reaction of Ad2 DNA with ORF6 specific DNA primers (Genzyme oligo. # 2371 -CGGATCCTTTATTATAGGGGAAGTCCACGC-CTAC (SEQ. ID NO:8) and oligo. #2372 -CGGGATCCATCGATGAAATATGACTACGTCCG (SEQ. ID NO:9) were inserted). Additional sequences supplied by the oligonucleotides included a cloning site at the 5' and 3' ends of the PCR fragment (ClaI and BamHI respectively) and a polyadenylation sequence at the 3' end to ensure correct polyadenylation of the ORF6 mRNA. As illustrated in FIG. 17, the PCR fragment was first ligated to a DNA fragment including the inverted terminal repeat (ITR) and E4 promoter region of Ad2 (Ad2 nucleotides 35937-35577) and cloned in the bacterial plasmid pBluescript (Stratagene) to create plasmid ORF6. After sequencing to verify the integrity of the ORF6 reading frame, the fragment encompassing the ITR and ORF6 was subcloned into a second plasmid, pAd ΔE4, which contains the 3' end of Ad2 from a Sac I site to the 3' ITR (Ad2 nucleotides 28562–35937) and is deleted for all E4 sequences (promoter to poly A site Ad2 positions 32815–35641) using flunking restriction sites. In this second plasmid, virus expressing only E4 ORF6, pAdORF6 was cut with restriction enzyme PacI and ligated to Ad2 DNA digested with PacI. This PacI site corresponds to Ad2 nucleotide 28612. 293 cells were transfected with the ligation and the resulting virus was subjected to restriction analysis to verify that the Ad2 E4 region had been substituted with the corresponding region of pAdORF6 and that the only remaining E4 open reading frame was ORF6.

A cell line could in theory be established that would fully complement E4 functions deleted from a recombinant virus.

The problem with this approach is that E4 functions in the regulation of host cell protein synthesis and is therefore toxic to cells. Our current recombinant adenoviruses are deleted for the E1 region and must be grown in 293 cells which complement E1 functions. The E4 promoter is activated in by the E1a gene product, and therefore to prevent inadvertent toxic expression of E4 transcription of E4 must be tightly regulated. The requirements of such a promoter or transactivating system is that in the uninduced state expression must be low enough to avoid toxicity to the host cell, but in the induced state must be sufficiently activated to make enough E4 gene product to complement the E4 deleted virus during virus production.

Example 13

An adenoviral vector is prepared as described in Example 7 while substituting the PGK promoter for the E1a promoter.

Example 14

An adenoviral vector is prepared as described in Example 11 while substituting the PGK promoter for the Ad2 major late promoter (MLP).

Example 15

Generation of Ad2-ORF6/PGK-CFTR

This protocol uses a second generation adenovirus vector named Ad2-ORF6/PGK-CFTR. This virus lacks E1 and in its place contains a modified transcription unit with the phosphoglycerate kinase (PGK) promoter and a poly A addition site flanking the CFTR cDNA. The PGK promoter is of only moderate strength but is long lasting and not subject to shut off. The E4 region of the vector has also been modified in that the whole coding sequence has been removed and replaced by 0RF6, the only E4 gene essential for growth of Ad in tissue culture. This has the effect of generating a genome of 101% the size of wild type Ad2 and renders the vector more easy to grow in culture than Ad2-ORF6/PGK-CFTR.

The DNA construct comprises a full length copy of the Ad2 genome from which the early region 1 (E1) genes (present at the 5' end of the viral genome) have been deleted and replaced by an expression cassette encoding CFTR. The expression cassette includes the promoter for phosphoglycerate kinase (PGK) and a polyadenylation (poly A) addition signal from the bovine growth hormone gene (BGH). In addition, the E4 region of Ad2 has been deleted and replaced with only open reading frame 6 (ORF6) of the Ad2 E4 region. The Adenovirus vector is referred to as AD2-ORF6/PGK-CFTR and is illustrated schematically in FIG. 28. The entire wild-type Ad2 genome has been previously sequenced (Roberts, R. J., (1986) In Adenovirus DNA, W. Oberfler, editor, Matinus Nihoff Publishing, Boston) and we have adopted the existing numbering system when referring to the wild type genome. Ad2 genomic regions flanking E1 and E4 deletions, and insertions into the genome are being completely sequenced.

The Ad2-ORF6/PGK-CFTR construct differs from the one used in our earlier protocol (Ad2/CFTR-l) in that the latter utilized the endogenous E1a promoter, had no poly A addition signal directly downstream of CFTR and retained an intact E4 region. The properties of Ad2/CFTR-1 in tissue culture and in animal studies h have been reported (Rich et al., (1993) *Human Gene Therapy*, 4:461–467; and Zabner et al. (1993) *Nature Genetics*, In Press).

At the 5' end of the genome, nucleotides 357 to 3328 of Ad2 have been deleted and replaced with (in order 5' to 3') 22 nucleotides of linker, 534 nucleotides of the PGK promoter, 86 nucleotides of linker, nucleotides 123–4622 of the published CFTR sequence (Riordan et al. (1989) *Science*, 245:1066–1073), 21 nucleotides of linker, and a 32 nucleotide synthetic BGH poly A addition signal followed by a final 11 nucleotides of linker. The topology of the 5' end of the recombinant molecule is illustrated in FIG. 28.

At the 3' end of the genome of Ad2-ORF6/PGK-CFTR, Ad2 sequences between nucleotides 32815 and 35577 have been deleted to remove all open reading frames of E4 but retain the E4 promoter, the E4 cap sites and first 32–37 nucleotides of E4 mRNA. The deleted sequences were replaced with a fragment derived by PCR which contains open reading frame 6 of Ad2 (nucleotides 34082–33178) and a synthetic poly A addition signal. The topology of the 3' end of the molecule is shown in FIG. 28. The predicted sequence of this region of the molecule is given at the end of this appendix. The sequence of this segment of the molecule will be confirmed. The remainder of the Ad2 viral DNA sequence is published in Roberts, R. J. in Adenovirus DNA. (W. Oberfler, Matinus Nihoff Publishing, Boston, 1986 ). The overall size of the Ad2-ORF6/PGK-CFTR vector is 36,336 bp which is 101.3% of full length Ad2.

The CFTR transcript is predicted to initiate at one of three closely spaced transcriptional start sites in the cloned PGK promoter (Singer-Sam et al. (1984) *Gene*, 32:409–417) at nucleotides 828, 829 and 837 of the recombinant vector (Singer-Sam et al. (1984) *Gene*, 32:409–417). A hybrid 5' untranslated region is comprised of 72, 80 or 81 nucleotides of PGK promoter region, 86 nucleotide of linker sequence, and 10 nucleotides derived from the CFTR insert. Transcriptional termination is expected to be directed by the BGH poly A addition signal at recombinant vector nucleotide 5530 yielding an approximately 4.7 kb transcript. The CFTR coding region comprises nucleotides 1010–5454 of the recombinant virus and nucleotides 182, 181 or 173 to 4624, 4623, or 4615 of the PGK-CFTR-BGH mRNA respectively, depending on which transcriptional initiation site is used. Within the CFTR cDNA there are two differences from the published (Riordan et al, cited supra) cDNA sequence. An A to C change at position 1990 of the CFTR cDNA (published CFTR cDNA coordinates) which was an error in the original published sequence, and a T to C change introduced at position 936. The change at position 936 is translationally silent but increases the stability of the cDNA when propagated in bacterial plasmids (Gregory et al. (1990) *Nature*, 347:382–386; and Cheng et al. (1990) *Cell*, 63:827–834). The 3' untranslated region of the predicted CFTR transcript comprises 21 nucleotides of linker sequence and approximately 10 nucleotides of synthetic BGH poly A additional signal.

Although the activity of CFTR can be measured by electrophysiological methods, it is relatively difficult to detect biochemically or immunocytochemically, particularly at low levels of expression (Gregory et al., cited supra; and Denning et al. (1992) *J. Cell Biol.*, 118:551–559). A high expression level reporter gene encoding the *E. coli* β galactosidase protein fused to a nuclear localization signal derived from the SV40 T-antigen was therefore constructed. Reporter gene transcription is driven by the powerful CMV early gene constitutive promoter. Specifically, the E1 region of wild type Ad2 between nucleotides 357– 3498 has been deleted and replaced it with a 515 bp fragment containing the CMV promoter and a 3252 bp fragment encoding the β galactosidase gene.

Regulatory Characteristics of the Elements of the AD2-ORF6/PGK-CFTR

In general terms, the vector is similar to several earlier adenovirus vectors encoding CFTR but it differs in three specific, ways from our earlier Ad2/CFTR-1 construct.

PGK Promoter

Transcription of CFTR is from the PGK promoter. This is a promoter of only moderate strength but because it is a so-called house keeping promoter we considered it more likely to be capable of long term albeit perhaps low level expression. It may also be less likely to be subject to "shut-down" than some of the very strong promoters used in other studies especially with retroviruses. Since CFTR is not an abundant protein we believe longevity of expression is probably more critical than high level expression. Expression from the PGK promoter in a retrovirus vector has been shown to be long lasting (Apperley et al. (1991) *Blood*, 78:310–317).

Polyadenylation Signal

Ad2-ORG6/PGK-CFTR contains an exogenous poly A addition signal after the CFTR coding region and prior to the protein IX coding sequence of the Ad2 E1 region. Since protein is believed to be involved in packaging of virions, we retained this coding region. Furthermore, since protein IX is synthesized from a separate transcript with its own promoter, to prevent possible promoter occlusion at the protein IX promoter, we inserted the BGH poly A addition signal. We have indirect evidence that promoter occlusion can be problematic in that Ad2/CMV βGal grows to lower viral titers on 293 cells than does Ad2/βgal-1. These constructs are identical except for the promoter used for β galactosidase expression. Since the CMV promoter is much stronger than the E1a promoter we assume that abundant transcription from the CMV promoter through the β galactosidase DNA into the protein IX coding region reduces expression of protein IX from its own promoter by promoter occlusion and that this is responsible for the lower titer of Ad2/CMV-βgal we obtain.

Alterations of the E4 Region

A large portion of the E4 region of the Ad2 genome has been deleted for two reasons. The first reason is to decrease the size of the vector used or expression of CFTR. Adenovirus vectors with genomes much larger than wild type are packaged less efficiently and are therefore difficult to grow to high titer. The combination of the deletions in the E1 and E4 regions in Ad2-ORF6/PGK-CFTR reduce the genome size to 101% of wild type. In practice we find that it is straightforward to prepare high tier lots of this virus.

The second reason to remove E4 sequences relates to the safety of adenovirus vectors. It is our goal to remove as many viral genes as possible to inactive the Ad2 virus backbone in as many ways as possible. The OF 6/7 gene of the E4 region encodes a protein that is involved in activation of the cellular transcription factor E2-F which is in turn implicated in the activation of the E2 region of adenovirus (Hemstrom et al. (1991) *J. Virol.*, 65:1440–1449). Therefore removal of ORF6/7 from adenovirus vectors may provide a further margin of safety at least when grown in non-proliferating cells. The removal of the E1 region already renders such vectors disabled, in part because E1a, if present, is able to displace E2-F from the retinoblastoma gene product, thereby also contributing to the stimulation of E2 transcription. The ORF6 reading frame of Ad2 was added back to the E1–E4 backbone of the Ad2-ORF6/PGK-CFTR vector because ORF6 function is essential for production of the recombinant virus in 293 cells. ORF6 is believed to be involved in DNA replication, host cell shut off and late mRNA accumulation in the normal adenovirus life cycle. The E1-E4-ORF6$^+$ backbone Ad2 vector does replicate in 293 cells.

The promoter/enhancer use to drive transcription of ORF6 of E4 is the endogenous E4 promoter. This promoter requires E1a for activation and contains E1a core enhancer elements and SP1 transcription factor binding sites (reviewed in Berk, A. J. (1986) *Ann. Rev. Genet.*, 20:75–79).

Replication Origin

The only replication origins present in Ad2-ORF6/PGK-CFTR are those present in the Ad2 parent genome. Replication of Ad2-ORF6/PGK-CFTR sequences has not been detected except when complemented with wild type E1 activity.

Steps Used to Derive the DNA Construct

Construction of the recombinant Ad2-ORF6/PGK-CFTR virus was accomplished by in vivo recombination of Ad2-ORF6 DNA and a plasmid containing the 5' 10.7 Kb of adenovirus engineered to have an expression cassette encoding the human CFTR cDNA driven by the PGK promoter and a BGH poly A signal in place of the E1 coding region.

The generation of the plasmid, pBRAd2/PGK/CFTR is described here. The starting plasmid contains an approximately 7.5 Kb insert cloned into the ClaI and BamHI sites of pBR322 and comprises the first 10,680 nucleotides of Ad2 with a deletion of the Ad2 sequences between nucleotides 356 and 3328. This plasmid contains a CMV promoter inserted into the ClaI and SpeI sites at the region of the E1 deletion and is designated pBRAd2/CMV. The plasmid also contains the Ad2 5' ITR, packaging and replication sequences and E1 enhancer. The E1 promoter, E1a and most of E1b coding region has been deleted. The 3' terminal portion of the E1b coding region coincides with the pIX promoter which was retained. The CMV promoter was removed and replaced with the PGK promoter as a ClaI and SpeI fragment from the plasmid PGK-GCR. The resulting plasmid, pBRAd2/PGK, was digested with AvrII and BstBI and the excised fragment replaced with the SpeI to BstBI fragment from the plasmid construct pAd2E1a/CFTR. This transferred a fragment containing the CFTR cDNA, BGH poly A signal and the Ad2 genomic sequences from 3327 to 10,670. The resulting plasmid is designated pBRAd2/PGK/CFTR. The CFTR cDNA fragment was originally derived from the plasmid pCMV-CFTR-936C using restriction enzymes SpeI and Ecl13611. pCMV-CFTR-936C consists of a minimal CFTR cDNA encompassing nucleotides 123–4622 of the published CFTR sequence cloned into the multiple cloning site of pRC/CMV (Invitrogen Corp.) using synthetic linkers. The CFTR cDNA within this plasmid has been completely sequenced.

The Ad2 backbone virus with the E4 region that expresses only open reading frame 6 was constructed as follows. A DNA fragment encoding ORF6 (Ad2 nucleotides 34082-33178) was derived by PCR with ORF6 specific DNA primers. Additional sequences supplied by the oligonucleotides include cloning sites at the 5' and 3' ends of the PCR fragment. (ClaI and BamHI respectively) and a poly A addition sequence AATAAA at the 3' end to ensure correct polyadenylation of ORF6 mRNA. The PCR fragment was cloned into pBluescript (Stratagene) along with an Ad2 fragment (nucleotides 35937–35577) containing the inverted terminal repeat, E4 promoter, E4 mRNA cap sites and first 32–37 nucleotides of E4 mRNA to create pORF6. A SalI-BamHI fragment encompassing the ITR and ORF6 was used to replace the SalI-BamHI fragment encompassing the ITR and E4 deletion in pAdΔE4 contains the 3' end of Ad2 from a SpeI site to the 3' ITR (nucleotides 27123-35937) and is deleted for all E4 sequences including the promoter and poly A signal (nucleotides 32815–35641). The resulting construct, pAdE4ORF6 was cut with PacI and ligated to Ad2 DNA digested with PacI nucleotide 28612). 293 cells were transfected with the ligation reaction to generate virus containing only open reading frame 6 from the E4 region.

In Vitro Studies with Ad2-ORF6/PGK-CFTR

The ability of Ad2-ORF6/PGK-CFTR to express CFTR in several cell lines, including human HeLa cells, human 293 cells, and primary cultures of normal and CF human airway epithelia. As an example, the results from the human 293 cells is related here. When human 293 cells were grown on culture dishes, the vector was able to transfer CFTR cDNA and express CFTR as assessed by immunoprecipitation and by functional assays of halide efflux. Gregory, R. J. et al. (1990) Nature 347:382–386; Cheng, S. H. et al. (1990) Cell 63:827–834. More specifically, procedures for preparing cell lysates, immunoprecipitation of proteins using anti-CFTR antibodies, one-dimensional peptide analysis and SDS-polyacrylamide gel electrophoresis were as described by Cheng et al. Cheng, S. H. et al. (1990) Cell 63:827–834.

Halide efflux assays were performed as described by Cheng, S. H. et al. (1991) Cell 66:1027–1036. cAMP-stimulated CFTR chloride channel activity using the halide sensitive fluorophore SPQ in 293 cells treated with 500 IU/cell Ad2-ORF6/PGK-CFTR. Stimulation of the infected cells with forskolin (20 $\mu$M) and IBMX (100 $\mu$m) increased SPQ fluorescence indicating the presence of functional chloride channels produced by the vector.

Additional studies using primary cultures of human airway (nasal polyp) epithelial cells (from CF patients) infected with Ad2-ORF6/PGK-CFTR demonstrated that Ad2-ORF6/PGK-CFTR infection of the nasal polyp epithelial cells resulted in the expression of cAMP dependent Cl$^-$ channels. FIG. 29 is an example of the results obtained from such studies. Primary cultures of CF nasal polyp epithelial cells were infected with Ad2-ORF6/PGK-CFTR at multiplicities of 0.3,3,and 50. Three days post infection, monlayers were mounted in Ussing chambers and short-circuit current was measured. At the indicated times: (1) 10 $\mu$M amiloride, (2) cAMP agonists (10 $\mu$M forskolin and 100 $\mu$M IBMX), and (3) 1 mM diphenylamine-2-carboxylate were addied to the mucosal solution.

In Vivo Studies with Ad2-ORF6/PGK-CFTR

Virus preparation

Two preparations of Ad2-ORF6/PGK-CFTR virus were used in this study. Both were prepared at Genzyme Corporation, in a Research Laboratory. The preparations were purified on a CsCl gradient and then dialyzed against tris-buffered saline to remove the CsCl. The preparation for the first administration (lot #2) had a titer of $2\times10^{10}$ IU/ml. The preparation for the second administration (lot #6) had a titer of $4\times10^{10}$ IU/ml.

Animals

Three female Rhesus monkeys, Macaca mulatta, were used for this study. Monkey C (#20046) weighed 6.4 kg. Monkey D (#20047) weighed 6.25 kg. Monkey E (#20048) weighed 10 kg. The monkeys were housed in the University of Iowa at least 360 days before the start of the study. The animals were maintained with free access to food and water throughout the study. The animals were part of a safety study and efficacy study for a different viral vector (Ad2/CFTR-1) and they were exposed to 3 nasal viral instillation throughout the year. The previous instillation of Ad2/CFTR-1) has been done 116 days prior to the initiation of this study. All three Rhesus monkeys had an anti-adenoviral antibody response detected by ELISA after each viral instillation. There are no known contaminants that are expected to interfere with the outcome of this study. Fluorescent lighting was controlled to automatically provide alternate light/dark cycles of approximately 12 hours each. The monkeys were housed in an isolation room in separate cages. Strict respiratory and body fluid isolation precautions were taken.

Virus administration

For application of the virus, the monkeys were anesthetized by intramuscular injection of ketamine (15 mg/kg). The entire epithelium of one nasal cavity in each monkey was used for this study. A foley catheter (size 10) was inserted through each nasal cavity into the pharynx, the balloon was inflated with a 2–3 ml of air, and then pulled anteriorly to obtain a tight occlusion at the posterior choana. The Ad2-ORF6/PGK-CFTR virus was then instilled slowly into the right nostril with the posterior balloon inflated. The viral solution remained in contact with the nasal mucosa for 30 min. The balloons were deflated, the catheters were removed, and the monkeys were allowed to recover from anesthesia.

On the first administration, the viral preparation had a titer of $2\times10^{10}$ IU/ml. and each monkey received approximately 0.3 ml. Thus the total dose applied to each monkey was approximately $6.5\times10^9$ IU. This total dose is approximately half the highest dose proposed for the human study. When considered on a IU/kg basis, a 6 kg monkey received a dose approximately 3 times greater that the highest proposed dose for a 60 kg human.

Timing of evaluations

The animals were evaluated on the day of administration, and on days 3, 7, 24, 38, and 44 days after infection. The second administration of virus occurred on day 44. The monkeys were evaluated on day 48 and then on days 55, 62, and 129.

For evaluations, monkeys were anesthetized by intramuscular injection of ketamine (15 mg/kg). To obtain nasal epithelial cells after the first viral administration, the nasal mucosa was first impregnated with 5 drops of Afrin (0.05% oxymetazoline hydrochloride, Schering-Plough) and 1 ml of 2% Lidocaine for 5 minutes. A cytobrush was then used to gently rub the mucosa for about 3 sec. To obtain pharyngeal epithelial swabs, a cotton-tipped applicator was rubbed over the back of the pharynx 2–3 times. The resulting cells were dislodged from brushes or applicators into 2 ml of sterile PBS. After the second administration of Ad2-ORF6/PGK-CFTR, the monkeys were followed clinically for 3 weeks, and mucosal biopsies were obtained from the monkeys medial turbinate at days 4, 11 and 18.

Animal evaluation

Animals were evaluated daily for evidence of abnormal behavior of physical signs. A record of food and fluid intake was used to assess appetite and general health. Stool consistency was also recorded to check for the possibility of diarrhea. At each of the evaluation time points, we measured rectal temperature, respiratory rate, and heart rate. The nasal mucosa, conjuctivas and pharynx were visually inspected. The monkeys were also examined for lymphadenopathy.

Hematology and serum chemistry

Venous blood from the monkeys was collected by standard venipuncture technique. Blood/serum analysis was performed in the clinical laboratory of the University of Iowa Hospitals and Clinics using a Hitatchi 737 automated chemistry analyzer and a Technicom H6 automated hematology analyzer.

Serology

Sera from the monkeys were obtained and antiadenoviral antibody titers were measured by ELISA. For the ELISA, 50 ng/well of killed adenovirus (Lee Biomolecular Research Laboratories, San Diego, Calif.) was coated in 0.1M NaHCO$_3$ at 4° C. overnight on 96 well plates. The test samples at appropriate dillutions were added, starting at a dillution of 1/50. The samples were incubated for 1 hour, the plates washed, and a Goat anti-human IgG HRP conjugate (Jackson ImmunoResearch Laboratories, West Grove, Pa.) was added for 1 hour. The plates were washed and O-Phenylenediamine (OPD) (Sigma Chemical Co., St. Louis, Mo.) was added for 30 min. at room temperature. The assay was stopped with 4.5M H$_2$SO$_4$ and read at 490 nm on a Molecular Devises microplate reader. The titer was calculated as the product of the reciprocal of the initial dilution and the reciprocal of the dilution in the last well with an OD>0.100. Nasal washings from the monkeys were obtained and antiadenoviral antibody titers were measured by ELISA, starting at a dilution of ¼.

Nasal Washings

Nasal washings were obtained to test for the possibility of secretory antibodies that could act as neutralizing antibodies. Three ml of sterile PBS as slowly instilled into the nasal cavity of the monkeys, the fluid was collected by gravity. The washings were centrifuged at 1000 RPM for 5 minutes and the supernatant was used for anti-adenoviral, and neutralizing antibody measurement.

Cytolog

Cells were obtained from the monkey's nasal epithelium by gently rubbing the nasal mucosa for about 3 seconds with a cytobrush. The resulting cells were dislodged from the brushes into 2 ml of PBS. The cell suspension was spun at 5000 rpm for 5 min. and resuspended in 293 media at a concentration of 10$^6$ cells/ml. Forty μl of the cell suspension was placed on slides using a Cytospin. Cytospin slides were stained with Wright's stain and analyzed for cell differential using light microscopy.

Culture for Ad2-ORF6/PFK-CFTRB

To assess for the presence of infectious viral particles, the supernatant from the nasal brushings and pharyngeal swabs of the monkeys were used. Twenty-five μL of the supernatant was added in duplicate to 293 cells. 293 cells were used at 50% confluence and were seeded in 96 well plates. 293 cells were incubated for 72 hours at 37° C., then fixed with a mixture of equal parts of methanol and acetone for 10 min and incubated with an FITC label antiadenovirus monoclonal antibodies (Chemicon, Light Diagnostics, Temecuca, Calif.) for 30 min. Positive nuclear immunofluorescence was interpreted as positive culture.

Immunocytochemistry for the detection of CFTR

Cells were obtained by brushing. Eighty μl of cell suspension were spun onto gelatin-coated slides. The slides were allowed to air dry, and then fixed with 4% paraformaldehyde. The cells were permeabilized with 0.2 Triton-X (Pierce, Rockford, Ill.) and then blocked for 60 minutes with 5% goat serum (Sigma, Mo.). A pool of monoclonal antibodies (M13-1, M1-4, and M6-4) (Gregory et al., 1990; Denning et al., 1992b; Denning et al., 1992a) were added and incubated for 12 hours. The primary antibody was washed off and an antimouse biotinylated antibody (Biomeda, Foster City, Calif.) was added. After washing, the secondary antibody, streptavidin FITC (Biomeda, Foster City, Calif.) was added and the slides were observed with a laser scanning confocal microscope.

Biopsies

To assess for histologic evidence of safety, nasal medial turbinate biopsies were obtained on day 4, 11 and 18 after the second viral administration as described before (Zabner et al (1993) Human Gene Therapy, in press). Nasal biopsies were fixed in 4% formaldehyde and H&E stained sections were reviewed.

RESULTS

Studies of efficacy

To directly assess the presence of CFTR, cells obtained by brushing were plated onto slides by cytospin and stained with antibodies to CFTR. A positive reaction is clearly evident in cells exposed to Ad2-ORF6/PGK-CFTR. The cells were scored as positive by immunocytochemistry when evaluated by a reader blinded to the identity of the samples. Cells obtained prior to infection and from other untreated monkeys were used as negative controls.

Studies of safety

None of the monkeys developed any clinical signs of viral infections or inflammation. There were no visible abnormalities at days 3, 4, 7 or on weekly inspection thereafter. Physical examination revealed no fever, lymphadenopathy, conjunctivitis, ocryza, tachypnea, or tachycardia at any of the time points. There was no cough, sneezing or diarrhea. The monkeys had no fever. Appetites and weights were not affected by virus administration in either monkey. The data are summarized in FIGS. 30A–30C.

The presence of live virus was tested in the supernatant of cell suspensions from swabs and brushes from each nostril and the pharynx. Each supernatant was used to infect the virus-sensitive 293 cell line. Live virus was never detected at any of the time points. The rapid loss of live virus suggests that there was no viral replication.

The results of complete blood counts, sedimentation rate, and clinical chemistries are shown in FIG. 31A–31C. There was no evidence of a systemic inflammatory response or other abnormalities of the clinical chemistries.

Epithelial inflammation was assessed by cytological examination of Wright-stained cells (cytospin) obtained from brushings of the nasal epithelium. The percentage of neutrophils and lymphocytes from the infected nostrils were compared to those of the control nostrils and values from four control monkeys. Wright stains of cells from nasal brushing were performed on each of the evaluation days. Neutrophils and lymphocytes accounted for less than 5% of total cells at all time points. The data are shown in FIGS. 32A–32C. The data indicate that administration of Ad2-ORF6/PGK-CFTR caused no change in the distribution or number of inflammatory cells at any of the time points following virus administration, even during a second administration of the virus. The biopsies slides obtained after the second Ad2-ORF6/PGK-CFTR administration were reviewed by an independent pathologist, who found no evidence of inflammation or any other cytopathic effects.

FIGS. 33A–33C shows that all three monkeys had developed antibody titers to adenovirus prior to the first infection with Ad2-ORF6/PGK-CFTR (Zabner et al. (1993) Human Gene Therapy (in press)). Antibody titers measured by ELISA rose within one week after the first and second administration and peaked at day 24. No antiadenoviral antibodies were detected by ELISA or neutralizing assay in nasal washings of any of the monkeys.

These results combined with demonstrate the ability of a recombinant adenovirus encoding CFTR (Ad2-ORF6/PGK-CFTR) to express CFTR cDNA in the airway epithelium of monkeys. These monkeys have been followed clinically for 12 months after the first viral administration and no complications have been observed.

The results of the safety studies are encouraging. We found no evidence of viral replication; infectious viral particles were rapidly cleared. The other major consideration for safety of an adenovirus vector in the treatment of CF is the possibility of an inflammatory response. The data indicate that the virus generated an antibody response, but despite this, we observed no evidence of a systemic or local inflammatory response. The cells obtained by brushings and swabs were not altered by virus application. Since these Monkeys had been previously exposed three times to Ad2/CFTR- 1, these data suggests that at least five sequential exposures of airway epithelium to adenovirus does not cause a detrimental inflammatory response.

These data indicate that Ad2-ORF6/PGK-CFTR can effectively transfer CFTR cDNA to airway epithelium and direct the expression of CFTR. They also indicate that transfer and expression is safe in primates.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. An adenoviral vector comprising an adenovirus genome from which the E1, E2, E3 and E4 regions and late genes of the adenovirus genome have been deleted and additionally comprising a nucleic acid of interest operably linked to expression control sequences.

2. The vector of claim 1 wherein the vector comprises the 5' and 3' inverted terminal repeat sequences, 5' packaging sequences and the E1A enhancer sequences of the adenovirus genome.

3. The vector of claim 2 wherein the vector further comprises a nuclear localization signal and a polyadenylation signal.

4. The vector of claim 3 wherein the expression control sequences comprise a PGK promoter.

5. The vector of claim 3 wherein the expression control sequences comprise the adenovirus major late promoter and the adenovirus tripartite leader, the nuclear localization signal comprises the SV40 T-antigen nuclear localization signal and the polyadenylation signal comprises the SV40 polyadenylation signal.

6. The vector of claim 5 wherein the vector further comprises an internal ribosomal entry site.

7. The vector of claim 6 wherein the internal initiation signal is the EMC internal ribosomal entry signal.

8. An adenoviral vector comprising the 5' and 3' inverted terminal repeat (ITR) sequences, the 5' packaging sequences and the E1A enhancer sequences of the adenovirus genome, wherein the vector can accommodate a foreign nucleic acid of up to 36 kb in length.

9. The vector of claim 8 further comprising a foreign nucleic acid of interest operably linked to expression control sequences.

10. The vector of claim 8 wherein the 5' inverted terminal repeat sequences, the 5' packaging sequences and the E1A enhancer sequence comprise nucleotides 0–358 of the adenoviral genome.

11. The vector of claim 8 wherein the 5' inverted terminal repeat sequences, the 5' packaging sequences and the E1A enhancer sequence comprise nucleotides 0–380 of the adenoviral genome.

12. A PAV I vector.

13. A PAV II vector.

14. A method for producing an adenoviral vector comprising an adenovirus genome from which the E1, E2, E3 and E4 regions and late genes of the adenovirus genome have been deleted and additionally comprising a foreign nucleic acid of interest operably linked to expression control sequences, the method comprising introducing the adenoviral vector nucleic acid and a helper virus nucleic acid into an adenovirus producer cell line and purifying the adenoviral vector and helper virus from said cell line.

15. A method for producing an adenoviral vector comprising the 5' and 3' inverted terminal repeat (ITR) sequences, the 5' packaging sequences and the E1A enhancer sequences of the adenoviral genome, wherein the vector can accommodate a foreign nucleic acid of up to 36 kb in length, the vector additionally comprising a foreign nucleic acid of interest operably linked to expression control sequences, the method comprising introducing the adenoviral vector nucleic acid and a helper virus nucleic acid into an adenovirus producer cell line and purifying the adenoviral vector and helper virus from said cell line.

16. The method of claim 14 or 15, further comprising purifying the adenoviral vector by cesium chloride gradient centrifugation.

17. The method of claim 14 or 15, wherein the helper virus supplies adenovirus replication and/or adenoviral structural proteins to the adenoviral vector, thereby allowing said adenoviral vector to be replicated and packaged.

18. The method of claim 17, wherein the helper virus is a packaging and/or replication deficient adenovirus.

19. The method of claim 17, wherein the helper virus is a packaging defective adenovirus.

20. The method of claim 19 wherein the helper virus has mutations in the adenovirus packaging sequences.

21. The method of claim 17, wherein the helper virus is a replication deficient adenovirus.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 6129 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 133..4572

( x i ) SEQUENCE DESCRIPTION: SEQ ID NO:1:

| | | | | | | | | | | | | | |
|---|---|---|---|---|---|---|---|---|---|---|---|---|---|
| AATTGGAAGC | AAATGACATC | ACAGCAGGTC | AGAGAAAAAG | GGTTGAGCGG | CAGGCACCCA | | | | | | | | 60 |
| GAGTAGTAGG | TCTTTGGCAT | TAGGAGCTTG | AGCCCAGACG | GCCCTAGCAG | GGACCCCAGC | | | | | | | | 120 |

| GCC CGA GAGA | CC ATG | CAG | AGG | TCG | CCT | CTG | GAA | AAG | GCC | AGC | GTT | GTC | 168 |
|---|---|---|---|---|---|---|---|---|---|---|---|---|---|
| | Met | Gln | Arg | Ser | Pro | Leu | Glu | Lys | Ala | Ser | Val | Val | |
| | 1 | | | | 5 | | | | | 10 | | | |

| TCC | AAA | CTT | TTT | TTC | AGC | TGG | ACC | AGA | CCA | ATT | TTG | AGG | AAA | GGA | TAC | 216 |
|---|---|---|---|---|---|---|---|---|---|---|---|---|---|---|---|---|
| Ser | Lys | Leu | Phe | Phe | Ser | Trp | Thr | Arg | Pro | Ile | Leu | Arg | Lys | Gly | Tyr | |
| | | 15 | | | | | 20 | | | | | 25 | | | | |

| AGA | CAG | CGC | CTG | GAA | TTG | TCA | GAC | ATA | TAC | CAA | ATC | CCT | TCT | GTT | GAT | 264 |
|---|---|---|---|---|---|---|---|---|---|---|---|---|---|---|---|---|
| Arg | Gln | Arg | Leu | Glu | Leu | Ser | Asp | Ile | Tyr | Gln | Ile | Pro | Ser | Val | Asp | |
| | 30 | | | | | 35 | | | | | 40 | | | | | |

| TCT | GCT | GAC | AAT | CTA | TCT | GAA | AAA | TTG | GAA | AGA | GAA | TGG | GAT | AGA | GAG | 312 |
|---|---|---|---|---|---|---|---|---|---|---|---|---|---|---|---|---|
| Ser | Ala | Asp | Asn | Leu | Ser | Glu | Lys | Leu | Glu | Arg | Glu | Trp | Asp | Arg | Glu | |
| 45 | | | | | 50 | | | | | 55 | | | | | 60 | |

| CTG | GCT | TCA | AAG | AAA | AAT | CCT | AAA | CTC | ATT | AAT | GCC | CTT | CGG | CGA | TGT | 360 |
|---|---|---|---|---|---|---|---|---|---|---|---|---|---|---|---|---|
| Leu | Ala | Ser | Lys | Lys | Asn | Pro | Lys | Leu | Ile | Asn | Ala | Leu | Arg | Arg | Cys | |
| | | | | 65 | | | | | 70 | | | | | 75 | | |

| TTT | TTC | TGG | AGA | TTT | ATG | TTC | TAT | GGA | ATC | TTT | TTA | TAT | TTA | GGG | GAA | 408 |
|---|---|---|---|---|---|---|---|---|---|---|---|---|---|---|---|---|
| Phe | Phe | Trp | Arg | Phe | Met | Phe | Tyr | Gly | Ile | Phe | Leu | Tyr | Leu | Gly | Glu | |
| | | | 80 | | | | | 85 | | | | | 90 | | | |

| GTC | ACC | AAA | GCA | GTA | CAG | CCT | CTC | TTA | CTG | GGA | AGA | ATC | ATA | GCT | TCC | 456 |
|---|---|---|---|---|---|---|---|---|---|---|---|---|---|---|---|---|
| Val | Thr | Lys | Ala | Val | Gln | Pro | Leu | Leu | Leu | Gly | Arg | Ile | Ile | Ala | Ser | |
| | | 95 | | | | | 100 | | | | | 105 | | | | |

| TAT | GAC | CCG | GAT | AAC | AAG | GAG | GAA | CGC | TCT | ATC | GCG | ATT | TAT | CTA | GGC | 504 |
|---|---|---|---|---|---|---|---|---|---|---|---|---|---|---|---|---|
| Tyr | Asp | Pro | Asp | Asn | Lys | Glu | Glu | Arg | Ser | Ile | Ala | Ile | Tyr | Leu | Gly | |
| | 110 | | | | | 115 | | | | | 120 | | | | | |

| ATA | GGC | TTA | TGC | CTT | CTC | TTT | ATT | GTG | AGG | ACA | CTG | CTC | CTA | CAC | CCA | 552 |
|---|---|---|---|---|---|---|---|---|---|---|---|---|---|---|---|---|
| Ile | Gly | Leu | Cys | Leu | Leu | Phe | Ile | Val | Arg | Thr | Leu | Leu | Leu | His | Pro | |
| 125 | | | | | 130 | | | | | 135 | | | | | 140 | |

| | | | | | | | | | | | | | | | | |
|---|---|---|---|---|---|---|---|---|---|---|---|---|---|---|---|---|
| GCC | ATT | TTT | GGC | CTT | CAT | CAC | ATT | GGA | ATG | CAG | ATG | AGA | ATA | GCT | ATG | 600 |
| Ala | Ile | Phe | Gly | Leu | His | His | Ile | Gly | Met | Gln | Met | Arg | Ile | Ala | Met | |
| | | | 145 | | | | | 150 | | | | | 155 | | | |
| TTT | AGT | TTG | ATT | TAT | AAG | AAG | ACT | TTA | AAG | CTG | TCA | AGC | CGT | GTT | CTA | 648 |
| Phe | Ser | Leu | Ile | Tyr | Lys | Lys | Thr | Leu | Lys | Leu | Ser | Ser | Arg | Val | Leu | |
| | | | 160 | | | | | 165 | | | | | 170 | | | |
| GAT | AAA | ATA | AGT | ATT | GGA | CAA | CTT | GTT | AGT | CTC | CTT | TCC | AAC | AAC | CTG | 696 |
| Asp | Lys | Ile | Ser | Ile | Gly | Gln | Leu | Val | Ser | Leu | Leu | Ser | Asn | Asn | Leu | |
| | | 175 | | | | | 180 | | | | | 185 | | | | |
| AAC | AAA | TTT | GAT | GAA | GGA | CTT | GCA | TTG | GCA | CAT | TTC | GTG | TGG | ATC | GCT | 744 |
| Asn | Lys | Phe | Asp | Glu | Gly | Leu | Ala | Leu | Ala | His | Phe | Val | Trp | Ile | Ala | |
| | 190 | | | | | 195 | | | | | 200 | | | | | |
| CCT | TTG | CAA | GTG | GCA | CTC | CTC | ATG | GGG | CTA | ATC | TGG | GAG | TTG | TTA | CAG | 792 |
| Pro | Leu | Gln | Val | Ala | Leu | Leu | Met | Gly | Leu | Ile | Trp | Glu | Leu | Leu | Gln | |
| 205 | | | | | 210 | | | | | 215 | | | | | 220 | |
| GCG | TCT | GCC | TTC | TGT | GGA | CTT | GGT | TTC | CTG | ATA | GTC | CTT | GCC | CTT | TTT | 840 |
| Ala | Ser | Ala | Phe | Cys | Gly | Leu | Gly | Phe | Leu | Ile | Val | Leu | Ala | Leu | Phe | |
| | | | | 225 | | | | | 230 | | | | | 235 | | |
| CAG | GCT | GGG | CTA | GGG | AGA | ATG | ATG | ATG | AAG | TAC | AGA | GAT | CAG | AGA | GCT | 888 |
| Gln | Ala | Gly | Leu | Gly | Arg | Met | Met | Met | Lys | Tyr | Arg | Asp | Gln | Arg | Ala | |
| | | | 240 | | | | | 245 | | | | | 250 | | | |
| GGG | AAG | ATC | AGT | GAA | AGA | CTT | GTG | ATT | ACC | TCA | GAA | ATG | ATT | GAA | AAT | 936 |
| Gly | Lys | Ile | Ser | Glu | Arg | Leu | Val | Ile | Thr | Ser | Glu | Met | Ile | Glu | Asn | |
| | | 255 | | | | | 260 | | | | | 265 | | | | |
| ATC | CAA | TCT | GTT | AAG | GCA | TAC | TGC | TGG | GAA | GAA | GCA | ATG | GAA | AAA | ATG | 984 |
| Ile | Gln | Ser | Val | Lys | Ala | Tyr | Cys | Trp | Glu | Glu | Ala | Met | Glu | Lys | Met | |
| | 270 | | | | | 275 | | | | | 280 | | | | | |
| ATT | GAA | AAC | TTA | AGA | CAA | ACA | GAA | CTG | AAA | CTG | ACT | CGG | AAG | GCA | GCC | 1032 |
| Ile | Glu | Asn | Leu | Arg | Gln | Thr | Glu | Leu | Lys | Leu | Thr | Arg | Lys | Ala | Ala | |
| 285 | | | | | 290 | | | | | 295 | | | | | 300 | |
| TAT | GTG | AGA | TAC | TTC | AAT | AGC | TCA | GCC | TTC | TTC | TTC | TCA | GGG | TTC | TTT | 1080 |
| Tyr | Val | Arg | Tyr | Phe | Asn | Ser | Ser | Ala | Phe | Phe | Phe | Ser | Gly | Phe | Phe | |
| | | | | 305 | | | | | 310 | | | | | 315 | | |
| GTG | GTG | TTT | TTA | TCT | GTG | CTT | CCC | TAT | GCA | CTA | ATC | AAA | GGA | ATC | ATC | 1128 |
| Val | Val | Phe | Leu | Ser | Val | Leu | Pro | Tyr | Ala | Leu | Ile | Lys | Gly | Ile | Ile | |
| | | | 320 | | | | | 325 | | | | | 330 | | | |
| CTC | CGG | AAA | ATA | TTC | ACC | ACC | ATC | TCA | TTC | TGC | ATT | GTT | CTG | CGC | ATG | 1176 |
| Leu | Arg | Lys | Ile | Phe | Thr | Thr | Ile | Ser | Phe | Cys | Ile | Val | Leu | Arg | Met | |
| | | 335 | | | | | 340 | | | | | 345 | | | | |
| GCG | GTC | ACT | CGG | CAA | TTT | CCC | TGG | GCT | GTA | CAA | ACA | TGG | TAT | GAC | TCT | 1224 |
| Ala | Val | Thr | Arg | Gln | Phe | Pro | Trp | Ala | Val | Gln | Thr | Trp | Tyr | Asp | Ser | |
| | 350 | | | | | 355 | | | | | 360 | | | | | |
| CTT | GGA | GCA | ATA | AAC | AAA | ATA | CAG | GAT | TTC | TTA | CAA | AAG | CAA | GAA | TAT | 1272 |
| Leu | Gly | Ala | Ile | Asn | Lys | Ile | Gln | Asp | Phe | Leu | Gln | Lys | Gln | Glu | Tyr | |
| 365 | | | | | 370 | | | | | 375 | | | | | 380 | |
| AAG | ACA | TTG | GAA | TAT | AAC | TTA | ACG | ACT | ACA | GAA | GTA | GTG | ATG | GAG | AAT | 1320 |
| Lys | Thr | Leu | Glu | Tyr | Asn | Leu | Thr | Thr | Thr | Glu | Val | Val | Met | Glu | Asn | |
| | | | | 385 | | | | | 390 | | | | | 395 | | |
| GTA | ACA | GCC | TTC | TGG | GAG | GAG | GGA | TTT | GGG | GAA | TTA | TTT | GAG | AAA | GCA | 1368 |
| Val | Thr | Ala | Phe | Trp | Glu | Glu | Gly | Phe | Gly | Glu | Leu | Phe | Glu | Lys | Ala | |
| | | | 400 | | | | | 405 | | | | | 410 | | | |
| AAA | CAA | AAC | AAT | AAC | AAT | AGA | AAA | ACT | TCT | AAT | GGT | GAT | GAC | AGC | CTC | 1416 |
| Lys | Gln | Asn | Asn | Asn | Asn | Arg | Lys | Thr | Ser | Asn | Gly | Asp | Asp | Ser | Leu | |
| | | 415 | | | | | 420 | | | | | 425 | | | | |
| TTC | TTC | AGT | AAT | TTC | TCA | CTT | CTT | GGT | ACT | CCT | GTC | CTG | AAA | GAT | ATT | 1464 |
| Phe | Phe | Ser | Asn | Phe | Ser | Leu | Leu | Gly | Thr | Pro | Val | Leu | Lys | Asp | Ile | |
| | 430 | | | | | 435 | | | | | 440 | | | | | |
| AAT | TTC | AAG | ATA | GAA | AGA | GGA | CAG | TTG | TTG | GCG | GTT | GCT | GGA | TCC | ACT | 1512 |
| Asn | Phe | Lys | Ile | Glu | Arg | Gly | Gln | Leu | Leu | Ala | Val | Ala | Gly | Ser | Thr | |
| 445 | | | | | 450 | | | | | 455 | | | | | 460 | |

| | | | | | | | | | | | | | | | | |
|---|---|---|---|---|---|---|---|---|---|---|---|---|---|---|---|---|
| GGA | GCA | GGC | AAG | ACT | TCA | CTT | CTA | ATG | ATG | ATT | ATG | GGA | GAA | CTG | GAG | 1560 |
| Gly | Ala | Gly | Lys | Thr | Ser | Leu | Leu | Met | Met | Ile | Met | Gly | Glu | Leu | Glu | |
| | | | 465 | | | | | 470 | | | | | 475 | | | |
| CCT | TCA | GAG | GGT | AAA | ATT | AAG | CAC | AGT | GGA | AGA | ATT | TCA | TTC | TGT | TCT | 1608 |
| Pro | Ser | Glu | Gly | Lys | Ile | Lys | His | Ser | Gly | Arg | Ile | Ser | Phe | Cys | Ser | |
| | | | 480 | | | | | 485 | | | | | 490 | | | |
| CAG | TTT | TCC | TGG | ATT | ATG | CCT | GGC | ACC | ATT | AAA | GAA | AAT | ATC | ATC | TTT | 1656 |
| Gln | Phe | Ser | Trp | Ile | Met | Pro | Gly | Thr | Ile | Lys | Glu | Asn | Ile | Ile | Phe | |
| | | 495 | | | | | 500 | | | | | 505 | | | | |
| GGT | GTT | TCC | TAT | GAT | GAA | TAT | AGA | TAC | AGA | AGC | GTC | ATC | AAA | GCA | TGC | 1704 |
| Gly | Val | Ser | Tyr | Asp | Glu | Tyr | Arg | Tyr | Arg | Ser | Val | Ile | Lys | Ala | Cys | |
| 510 | | | | | 515 | | | | | 520 | | | | | | |
| CAA | CTA | GAA | GAG | GAC | ATC | TCC | AAG | TTT | GCA | GAG | AAA | GAC | AAT | ATA | GTT | 1752 |
| Gln | Leu | Glu | Glu | Asp | Ile | Ser | Lys | Phe | Ala | Glu | Lys | Asp | Asn | Ile | Val | |
| 525 | | | | | 530 | | | | | 535 | | | | | 540 | |
| CTT | GGA | GAA | GGT | GGA | ATC | ACA | CTG | AGT | GGA | GGT | CAA | CGA | GCA | AGA | ATT | 1800 |
| Leu | Gly | Glu | Gly | Gly | Ile | Thr | Leu | Ser | Gly | Gly | Gln | Arg | Ala | Arg | Ile | |
| | | | | 545 | | | | | 550 | | | | | 555 | | |
| TCT | TTA | GCA | AGA | GCA | GTA | TAC | AAA | GAT | GCT | GAT | TTG | TAT | TTA | TTA | GAC | 1848 |
| Ser | Leu | Ala | Arg | Ala | Val | Tyr | Lys | Asp | Ala | Asp | Leu | Tyr | Leu | Leu | Asp | |
| | | | 560 | | | | | 565 | | | | | 570 | | | |
| TCT | CCT | TTT | GGA | TAC | CTA | GAT | GTT | TTA | ACA | GAA | AAA | GAA | ATA | TTT | GAA | 1896 |
| Ser | Pro | Phe | Gly | Tyr | Leu | Asp | Val | Leu | Thr | Glu | Lys | Glu | Ile | Phe | Glu | |
| | | 575 | | | | | 580 | | | | | 585 | | | | |
| AGC | TGT | GTC | TGT | AAA | CTG | ATG | GCT | AAC | AAA | ACT | AGG | ATT | TTG | GTC | ACT | 1944 |
| Ser | Cys | Val | Cys | Lys | Leu | Met | Ala | Asn | Lys | Thr | Arg | Ile | Leu | Val | Thr | |
| | 590 | | | | | 595 | | | | | 600 | | | | | |
| TCT | AAA | ATG | GAA | CAT | TTA | AAG | AAA | GCT | GAC | AAA | ATA | TTA | ATT | TTG | CAT | 1992 |
| Ser | Lys | Met | Glu | His | Leu | Lys | Lys | Ala | Asp | Lys | Ile | Leu | Ile | Leu | His | |
| 605 | | | | | 610 | | | | | 615 | | | | | 620 | |
| GAA | GGT | AGC | AGC | TAT | TTT | TAT | GGG | ACA | TTT | TCA | GAA | CTC | CAA | AAT | CTA | 2040 |
| Glu | Gly | Ser | Ser | Tyr | Phe | Tyr | Gly | Thr | Phe | Ser | Glu | Leu | Gln | Asn | Leu | |
| | | | | 625 | | | | | 630 | | | | | 635 | | |
| CAG | CCA | GAC | TTT | AGC | TCA | AAA | CTC | ATG | GGA | TGT | GAT | TCT | TTC | GAC | CAA | 2088 |
| Gln | Pro | Asp | Phe | Ser | Ser | Lys | Leu | Met | Gly | Cys | Asp | Ser | Phe | Asp | Gln | |
| | | | 640 | | | | | 645 | | | | | 650 | | | |
| TTT | AGT | GCA | GAA | AGA | AGA | AAT | TCA | ATC | CTA | ACT | GAG | ACC | TTA | CAC | CGT | 2136 |
| Phe | Ser | Ala | Glu | Arg | Arg | Asn | Ser | Ile | Leu | Thr | Glu | Thr | Leu | His | Arg | |
| | | 655 | | | | | 660 | | | | | 665 | | | | |
| TTC | TCA | TTA | GAA | GGA | GAT | GCT | CCT | GTC | TCC | TGG | ACA | GAA | ACA | AAA | AAA | 2184 |
| Phe | Ser | Leu | Glu | Gly | Asp | Ala | Pro | Val | Ser | Trp | Thr | Glu | Thr | Lys | Lys | |
| | 670 | | | | | 675 | | | | | 680 | | | | | |
| CAA | TCT | TTT | AAA | CAG | ACT | GGA | GAG | TTT | GGG | GAA | AAA | AGG | AAG | AAT | TCT | 2232 |
| Gln | Ser | Phe | Lys | Gln | Thr | Gly | Glu | Phe | Gly | Glu | Lys | Arg | Lys | Asn | Ser | |
| 685 | | | | | 690 | | | | | 695 | | | | | 700 | |
| ATT | CTC | AAT | CCA | ATC | AAC | TCT | ATA | CGA | AAA | TTT | TCC | ATT | GTG | CAA | AAG | 2280 |
| Ile | Leu | Asn | Pro | Ile | Asn | Ser | Ile | Arg | Lys | Phe | Ser | Ile | Val | Gln | Lys | |
| | | | | 705 | | | | | 710 | | | | | 715 | | |
| ACT | CCC | TTA | CAA | ATG | AAT | GGC | ATC | GAA | GAG | GAT | TCT | GAT | GAG | CCT | TTA | 2328 |
| Thr | Pro | Leu | Gln | Met | Asn | Gly | Ile | Glu | Glu | Asp | Ser | Asp | Glu | Pro | Leu | |
| | | | 720 | | | | | 725 | | | | | 730 | | | |
| GAG | AGA | AGG | CTG | TCC | TTA | GTA | CCA | GAT | TCT | GAG | CAG | GGA | GAG | GCG | ATA | 2376 |
| Glu | Arg | Arg | Leu | Ser | Leu | Val | Pro | Asp | Ser | Glu | Gln | Gly | Glu | Ala | Ile | |
| | | 735 | | | | | 740 | | | | | 745 | | | | |
| CTG | CCT | CGC | ATC | AGC | GTG | ATC | AGC | ACT | GGC | CCC | ACG | CTT | CAG | GCA | CGA | 2424 |
| Leu | Pro | Arg | Ile | Ser | Val | Ile | Ser | Thr | Gly | Pro | Thr | Leu | Gln | Ala | Arg | |
| | 750 | | | | | 755 | | | | | 760 | | | | | |
| AGG | AGG | CAG | TCT | GTC | CTG | AAC | CTG | ATG | ACA | CAC | TCA | GTT | AAC | CAA | GGT | 2472 |
| Arg | Arg | Gln | Ser | Val | Leu | Asn | Leu | Met | Thr | His | Ser | Val | Asn | Gln | Gly | |
| 765 | | | | | 770 | | | | | 775 | | | | | 780 | |

| | | | | | | | | | | | | | | | | |
|---|---|---|---|---|---|---|---|---|---|---|---|---|---|---|---|---|
| CAG | AAC | ATT | CAC | CGA | AAG | ACA | ACA | GCA | TCC | ACA | CGA | AAA | GTG | TCA | CTG | 2520 |
| Gln | Asn | Ile | His | Arg | Lys | Thr | Thr | Ala | Ser | Thr | Arg | Lys | Val | Ser | Leu | |
| | | | | 785 | | | | 790 | | | | | | 795 | | |
| GCC | CCT | CAG | GCA | AAC | TTG | ACT | GAA | CTG | GAT | ATA | TAT | TCA | AGA | AGG | TTA | 2568 |
| Ala | Pro | Gln | Ala | Asn | Leu | Thr | Glu | Leu | Asp | Ile | Tyr | Ser | Arg | Arg | Leu | |
| | | | 800 | | | | | 805 | | | | | 810 | | | |
| TCT | CAA | GAA | ACT | GGC | TTG | GAA | ATA | AGT | GAA | GAA | ATT | AAC | GAA | GAA | GAC | 2616 |
| Ser | Gln | Glu | Thr | Gly | Leu | Glu | Ile | Ser | Glu | Glu | Ile | Asn | Glu | Glu | Asp | |
| | | | 815 | | | | | 820 | | | | | 825 | | | |
| TTA | AAG | GAG | TGC | CTT | TTT | GAT | GAT | ATG | GAG | AGC | ATA | CCA | GCA | GTG | ACT | 2664 |
| Leu | Lys | Glu | Cys | Leu | Phe | Asp | Asp | Met | Glu | Ser | Ile | Pro | Ala | Val | Thr | |
| | | 830 | | | | | 835 | | | | | 840 | | | | |
| ACA | TGG | AAC | ACA | TAC | CTT | CGA | TAT | ATT | ACT | GTC | CAC | AAG | AGC | TTA | ATT | 2712 |
| Thr | Trp | Asn | Thr | Tyr | Leu | Arg | Tyr | Ile | Thr | Val | His | Lys | Ser | Leu | Ile | |
| 845 | | | | | 850 | | | | | 855 | | | | | 860 | |
| TTT | GTG | CTA | ATT | TGG | TGC | TTA | GTA | ATT | TTT | CTG | GCA | GAG | GTG | GCT | GCT | 2760 |
| Phe | Val | Leu | Ile | Trp | Cys | Leu | Val | Ile | Phe | Leu | Ala | Glu | Val | Ala | Ala | |
| | | | | 865 | | | | | 870 | | | | | 875 | | |
| TCT | TTG | GTT | GTG | CTG | TGG | CTC | CTT | GGA | AAC | ACT | CCT | CTT | CAA | GAC | AAA | 2808 |
| Ser | Leu | Val | Val | Leu | Trp | Leu | Leu | Gly | Asn | Thr | Pro | Leu | Gln | Asp | Lys | |
| | | | 880 | | | | | 885 | | | | | 890 | | | |
| GGG | AAT | AGT | ACT | CAT | AGT | AGA | AAT | AAC | AGC | TAT | GCA | GTG | ATT | ATC | ACC | 2856 |
| Gly | Asn | Ser | Thr | His | Ser | Arg | Asn | Asn | Ser | Tyr | Ala | Val | Ile | Ile | Thr | |
| | | 895 | | | | | 900 | | | | | 905 | | | | |
| AGC | ACC | AGT | TCG | TAT | TAT | GTG | TTT | TAC | ATT | TAC | GTG | GGA | GTA | GCC | GAC | 2904 |
| Ser | Thr | Ser | Ser | Tyr | Tyr | Val | Phe | Tyr | Ile | Tyr | Val | Gly | Val | Ala | Asp | |
| | | 910 | | | | | 915 | | | | | 920 | | | | |
| ACT | TTG | CTT | GCT | ATG | GGA | TTC | TTC | AGA | GGT | CTA | CCA | CTG | GTG | CAT | ACT | 2952 |
| Thr | Leu | Leu | Ala | Met | Gly | Phe | Phe | Arg | Gly | Leu | Pro | Leu | Val | His | Thr | |
| 925 | | | | | 930 | | | | | 935 | | | | | 940 | |
| CTA | ATC | ACA | GTG | TCG | AAA | ATT | TTA | CAC | CAC | AAA | ATG | TTA | CAT | TCT | GTT | 3000 |
| Leu | Ile | Thr | Val | Ser | Lys | Ile | Leu | His | His | Lys | Met | Leu | His | Ser | Val | |
| | | | | 945 | | | | | 950 | | | | | 955 | | |
| CTT | CAA | GCA | CCT | ATG | TCA | ACC | CTC | AAC | ACG | TTG | AAA | GCA | GGT | GGG | ATT | 3048 |
| Leu | Gln | Ala | Pro | Met | Ser | Thr | Leu | Asn | Thr | Leu | Lys | Ala | Gly | Gly | Ile | |
| | | | 960 | | | | | 965 | | | | | 970 | | | |
| CTT | AAT | AGA | TTC | TCC | AAA | GAT | ATA | GCA | ATT | TTG | GAT | GAC | CTT | CTG | CCT | 3096 |
| Leu | Asn | Arg | Phe | Ser | Lys | Asp | Ile | Ala | Ile | Leu | Asp | Asp | Leu | Leu | Pro | |
| | | 975 | | | | | 980 | | | | | 985 | | | | |
| CTT | ACC | ATA | TTT | GAC | TTC | ATC | CAG | TTG | TTA | TTA | ATT | GTG | ATT | GGA | GCT | 3144 |
| Leu | Thr | Ile | Phe | Asp | Phe | Ile | Gln | Leu | Leu | Leu | Ile | Val | Ile | Gly | Ala | |
| | | 990 | | | | | 995 | | | | | 1000 | | | | |
| ATA | GCA | GTT | GTC | GCA | GTT | TTA | CAA | CCC | TAC | ATC | TTT | GTT | GCA | ACA | GTG | 3192 |
| Ile | Ala | Val | Val | Ala | Val | Leu | Gln | Pro | Tyr | Ile | Phe | Val | Ala | Thr | Val | |
| 1005 | | | | | 1010 | | | | | 1015 | | | | | 1020 | |
| CCA | GTG | ATA | GTG | GCT | TTT | ATT | ATG | TTG | AGA | GCA | TAT | TTC | CTC | CAA | ACC | 3240 |
| Pro | Val | Ile | Val | Ala | Phe | Ile | Met | Leu | Arg | Ala | Tyr | Phe | Leu | Gln | Thr | |
| | | | | 1025 | | | | | 1030 | | | | | 1035 | | |
| TCA | CAG | CAA | CTC | AAA | CAA | CTG | GAA | TCT | GAA | GGC | AGG | AGT | CCA | ATT | TTC | 3288 |
| Ser | Gln | Gln | Leu | Lys | Gln | Leu | Glu | Ser | Glu | Gly | Arg | Ser | Pro | Ile | Phe | |
| | | | 1040 | | | | | 1045 | | | | | 1050 | | | |
| ACT | CAT | CTT | GTT | ACA | AGC | TTA | AAA | GGA | CTA | TGG | ACA | CTT | CGT | GCC | TTC | 3336 |
| Thr | His | Leu | Val | Thr | Ser | Leu | Lys | Gly | Leu | Trp | Thr | Leu | Arg | Ala | Phe | |
| | | | 1055 | | | | | 1060 | | | | | 1065 | | | |
| GGA | CGG | CAG | CCT | TAC | TTT | GAA | ACT | CTG | TTC | CAC | AAA | GCT | CTG | AAT | TTA | 3384 |
| Gly | Arg | Gln | Pro | Tyr | Phe | Glu | Thr | Leu | Phe | His | Lys | Ala | Leu | Asn | Leu | |
| | | 1070 | | | | | 1075 | | | | | 1080 | | | | |
| CAT | ACT | GCC | AAC | TGG | TTC | TTG | TAC | CTG | TCA | ACA | CTG | CGC | TGG | TTC | CAA | 3432 |
| His | Thr | Ala | Asn | Trp | Phe | Leu | Tyr | Leu | Ser | Thr | Leu | Arg | Trp | Phe | Gln | |
| 1085 | | | | | 1090 | | | | | 1095 | | | | | 1100 | |

| | | | | | | | | | | | | | | | | |
|---|---|---|---|---|---|---|---|---|---|---|---|---|---|---|---|---|
| ATG | AGA | ATA | GAA | ATG | ATT | TTT | GTC | ATC | TTC | TTC | ATT | GCT | GTT | ACC | TTC | 3480 |
| Met | Arg | Ile | Glu | Met | Ile | Phe | Val | Ile | Phe | Phe | Ile | Ala | Val | Thr | Phe | |
| | | | | 1105 | | | | | 1110 | | | | | 1115 | | |
| ATT | TCC | ATT | TTA | ACA | ACA | GGA | GAA | GGA | GAA | GGA | AGA | GTT | GGT | ATT | ATC | 3528 |
| Ile | Ser | Ile | Leu | Thr | Thr | Gly | Glu | Gly | Glu | Gly | Arg | Val | Gly | Ile | Ile | |
| | | | 1120 | | | | | 1125 | | | | | | 1130 | | |
| CTG | ACT | TTA | GCC | ATG | AAT | ATC | ATG | AGT | ACA | TTG | CAG | TGG | GCT | GTA | AAC | 3576 |
| Leu | Thr | Leu | Ala | Met | Asn | Ile | Met | Ser | Thr | Leu | Gln | Trp | Ala | Val | Asn | |
| | | | 1135 | | | | | 1140 | | | | | 1145 | | | |
| TCC | AGC | ATA | GAT | GTG | GAT | AGC | TTG | ATG | CGA | TCT | GTG | AGC | CGA | GTC | TTT | 3624 |
| Ser | Ser | Ile | Asp | Val | Asp | Ser | Leu | Met | Arg | Ser | Val | Ser | Arg | Val | Phe | |
| | | | 1150 | | | | | 1155 | | | | | 1160 | | | |
| AAG | TTC | ATT | GAC | ATG | CCA | ACA | GAA | GGT | AAA | CCT | ACC | AAG | TCA | ACC | AAA | 3672 |
| Lys | Phe | Ile | Asp | Met | Pro | Thr | Glu | Gly | Lys | Pro | Thr | Lys | Ser | Thr | Lys | |
| 1165 | | | | | 1170 | | | | | 1175 | | | | | 1180 | |
| CCA | TAC | AAG | AAT | GGC | CAA | CTC | TCG | AAA | GTT | ATG | ATT | ATT | GAG | AAT | TCA | 3720 |
| Pro | Tyr | Lys | Asn | Gly | Gln | Leu | Ser | Lys | Val | Met | Ile | Ile | Glu | Asn | Ser | |
| | | | | 1185 | | | | | 1190 | | | | | 1195 | | |
| CAC | GTG | AAG | AAA | GAT | GAC | ATC | TGG | CCC | TCA | GGG | GGC | CAA | ATG | ACT | GTC | 3768 |
| His | Val | Lys | Lys | Asp | Asp | Ile | Trp | Pro | Ser | Gly | Gly | Gln | Met | Thr | Val | |
| | | | 1200 | | | | | 1205 | | | | | 1210 | | | |
| AAA | GAT | CTC | ACA | GCA | AAA | TAC | ACA | GAA | GGT | GGA | AAT | GCC | ATA | TTA | GAG | 3816 |
| Lys | Asp | Leu | Thr | Ala | Lys | Tyr | Thr | Glu | Gly | Gly | Asn | Ala | Ile | Leu | Glu | |
| | | | 1215 | | | | | 1220 | | | | | 1225 | | | |
| AAC | ATT | TCC | TTC | TCA | ATA | AGT | CCT | GGC | CAG | AGG | GTG | GGC | CTC | TTG | GGA | 3864 |
| Asn | Ile | Ser | Phe | Ser | Ile | Ser | Pro | Gly | Gln | Arg | Val | Gly | Leu | Leu | Gly | |
| | | 1230 | | | | | 1235 | | | | | 1240 | | | | |
| AGA | ACT | GGA | TCA | GGG | AAG | AGT | ACT | TTG | TTA | TCA | GCT | TTT | TTG | AGA | CTA | 3912 |
| Arg | Thr | Gly | Ser | Gly | Lys | Ser | Thr | Leu | Leu | Ser | Ala | Phe | Leu | Arg | Leu | |
| 1245 | | | | | 1250 | | | | | 1255 | | | | | 1260 | |
| CTG | AAC | ACT | GAA | GGA | GAA | ATC | CAG | ATC | GAT | GGT | GTG | TCT | TGG | GAT | TCA | 3960 |
| Leu | Asn | Thr | Glu | Gly | Glu | Ile | Gln | Ile | Asp | Gly | Val | Ser | Trp | Asp | Ser | |
| | | | | 1265 | | | | | 1270 | | | | | 1275 | | |
| ATA | ACT | TTG | CAA | CAG | TGG | AGG | AAA | GCC | TTT | GGA | GTG | ATA | CCA | CAG | AAA | 4008 |
| Ile | Thr | Leu | Gln | Gln | Trp | Arg | Lys | Ala | Phe | Gly | Val | Ile | Pro | Gln | Lys | |
| | | | | 1280 | | | | | 1285 | | | | | 1290 | | |
| GTA | TTT | ATT | TTT | TCT | GGA | ACA | TTT | AGA | AAA | AAC | TTG | GAT | CCC | TAT | GAA | 4056 |
| Val | Phe | Ile | Phe | Ser | Gly | Thr | Phe | Arg | Lys | Asn | Leu | Asp | Pro | Tyr | Glu | |
| | | | | 1295 | | | | | 1300 | | | | | 1305 | | |
| CAG | TGG | AGT | GAT | CAA | GAA | ATA | TGG | AAA | GTT | GCA | GAT | GAG | GTT | GGG | CTC | 4104 |
| Gln | Trp | Ser | Asp | Gln | Glu | Ile | Trp | Lys | Val | Ala | Asp | Glu | Val | Gly | Leu | |
| | | | 1310 | | | | | 1315 | | | | | 1320 | | | |
| AGA | TCT | GTG | ATA | GAA | CAG | TTT | CCT | GGG | AAG | CTT | GAC | TTT | GTC | CTT | GTG | 4152 |
| Arg | Ser | Val | Ile | Glu | Gln | Phe | Pro | Gly | Lys | Leu | Asp | Phe | Val | Leu | Val | |
| 1325 | | | | | 1330 | | | | | 1335 | | | | | 1340 | |
| GAT | GGG | GGC | TGT | GTC | CTA | AGC | CAT | GGC | CAC | AAG | CAG | TTG | ATG | TGC | TTG | 4200 |
| Asp | Gly | Gly | Cys | Val | Leu | Ser | His | Gly | His | Lys | Gln | Leu | Met | Cys | Leu | |
| | | | | 1345 | | | | | 1350 | | | | | 1355 | | |
| GCT | AGA | TCT | GTT | CTC | AGT | AAG | GCG | AAG | ATC | TTG | CTG | CTT | GAT | GAA | CCC | 4248 |
| Ala | Arg | Ser | Val | Leu | Ser | Lys | Ala | Lys | Ile | Leu | Leu | Leu | Asp | Glu | Pro | |
| | | | | 1360 | | | | | 1365 | | | | | 1370 | | |
| AGT | GCT | CAT | TTG | GAT | CCA | GTA | ACA | TAC | CAA | ATA | ATT | AGA | AGA | ACT | CTA | 4296 |
| Ser | Ala | His | Leu | Asp | Pro | Val | Thr | Tyr | Gln | Ile | Ile | Arg | Arg | Thr | Leu | |
| | | | 1375 | | | | | 1380 | | | | | 1385 | | | |
| AAA | CAA | GCA | TTT | GCT | GAT | TGC | ACA | GTA | ATT | CTC | TGT | GAA | CAC | AGG | ATA | 4344 |
| Lys | Gln | Ala | Phe | Ala | Asp | Cys | Thr | Val | Ile | Leu | Cys | Glu | His | Arg | Ile | |
| | | | 1390 | | | | | 1395 | | | | | 1400 | | | |
| GAA | GCA | ATG | CTG | GAA | TGC | CAA | CAA | TTT | TTG | GTC | ATA | GAA | GAG | AAC | AAA | 4392 |
| Glu | Ala | Met | Leu | Glu | Cys | Gln | Gln | Phe | Leu | Val | Ile | Glu | Glu | Asn | Lys | |
| 1405 | | | | | 1410 | | | | | 1415 | | | | | 1420 | |

-continued

| | | | | | | | | | | | | | | | | |
|---|---|---|---|---|---|---|---|---|---|---|---|---|---|---|---|---|
| GTG | CGG | CAG | TAC | GAT | TCC | ATC | CAG | AAA | CTG | CTG | AAC | GAG | AGG | AGC | CTC | 4440 |
| Val | Arg | Gln | Tyr | Asp | Ser | Ile | Gln | Lys | Leu | Leu | Asn | Glu | Arg | Ser | Leu | |
| | | | | 1425 | | | | | 1430 | | | | | 1435 | | |
| TTC | CGG | CAA | GCC | ATC | AGC | CCC | TCC | GAC | AGG | GTG | AAG | CTC | TTT | CCC | CAC | 4488 |
| Phe | Arg | Gln | Ala | Ile | Ser | Pro | Ser | Asp | Arg | Val | Lys | Leu | Phe | Pro | His | |
| | | | 1440 | | | | | 1445 | | | | | 1450 | | | |
| CGG | AAC | TCA | AGC | AAG | TGC | AAG | TCT | AAG | CCC | CAG | ATT | GCT | GCT | CTG | AAA | 4536 |
| Arg | Asn | Ser | Ser | Lys | Cys | Lys | Ser | Lys | Pro | Gln | Ile | Ala | Ala | Leu | Lys | |
| | | 1455 | | | | | 1460 | | | | | 1465 | | | | |
| GAG | GAG | ACA | GAA | GAA | GAG | GTG | CAA | GAT | ACA | AGG | CTT | TAGAGAGCAG | | | | 4582 |
| Glu | Glu | Thr | Glu | Glu | Glu | Val | Gln | Asp | Thr | Arg | Leu | | | | | |
| | 1470 | | | | | 1475 | | | | | 1480 | | | | | |

| | | | | |
|---|---|---|---|---|
| CATAAATGTT | GACATGGAC | ATTTGCTCAT | GGAATTGGAG | CTCGTGGGAC AGTCACCTCA | 4642 |
| TGGAATTGGA | GCTCGTGGAA | CAGTTACCTC | TGCCTCAGAA | AACAAGGATG AATTAAGTTT | 4702 |
| TTTTTTAAAA | AAGAAACATT | TGGTAAGGGG | AATTGAGGAC | ACTGATATGG GTCTTGATAA | 4762 |
| ATGGCTTCCT | GGCAATAGTC | AAATTGTGTG | AAAGGTACTT | CAAATCCTTG AAGATTTACC | 4822 |
| ACTTGTGTTT | TGCAAGCCAG | ATTTTCCTGA | AAACCCTTGC | CATGTGCTAG TAATTGGAAA | 4882 |
| GGCAGCTCTA | AATGTCAATC | AGCCTAGTTG | ATCAGCTTAT | TGTCTAGTGA AACTCGTTAA | 4942 |
| TTTGTAGTGT | TGGAGAAGAA | CTGAAATCAT | ACTTCTTAGG | GTTATGATTA AGTAATGATA | 5002 |
| ACTGGAAACT | TCAGCGGTTT | ATATAAGCTT | GTATTCCTTT | TTCTCTCCTC TCCCCATGAT | 5062 |
| GTTTAGAAAC | ACAACTATAT | TGTTTGCTAA | GCATTCCAAC | TATCTCATTT CCAAGCAAGT | 5122 |
| ATTAGAATAC | CACAGGAACC | ACAAGACTGC | ACATCAAAAT | ATGCCCATT CAACATCTAG | 5182 |
| TGAGCAGTCA | GGAAAGAGAA | CTTCCAGATC | CTGGAAATCA | GGGTTAGTAT TGTCCAGGTC | 5242 |
| TACCAAAAAT | CTCAATATTT | CAGATAATCA | CAATACATCC | CTTACCTGGG AAAGGGCTGT | 5302 |
| TATAATCTTT | CACAGGGGAC | AGGATGGTTC | CCTTGATGAA | GAAGTTGATA TGCCTTTTCC | 5362 |
| CAACTCCAGA | AAGTGACAAG | CTCACAGACC | TTTGAACTAG | AGTTTAGCTG GAAAAGTATG | 5422 |
| TTAGTGCAAA | TTGTCACAGG | ACAGCCCTTC | TTTCCACAGA | AGCTCCAGGT AGAGGGTGTG | 5482 |
| TAAGTAGATA | GGCCATGGGC | ACTGTGGGTA | GACACACATG | AAGTCCAAGC ATTTAGATGT | 5542 |
| ATAGGTTGAT | GGTGGTATGT | TTTCAGGCTA | GATGTATGTA | CTTCATGCTG TCTACACTAA | 5602 |
| GAGAGAATGA | GAGACACACT | GAAGAAGCAC | CAATCATGAA | TTAGTTTTAT ATGCTTCTGT | 5662 |
| TTTATAATTT | TGTGAAGCAA | AATTTTTCT | CTAGGAAATA | TTTATTTTAA TAATGTTTCA | 5722 |
| AACATATATT | ACAATGCTGT | ATTTTAAAAG | AATGATTATG | AATTACATTT GTATAAAATA | 5782 |
| ATTTTTATAT | TTGAAATATT | GACTTTTTAT | GGCACTAGTA | TTTTTATGAA ATATTATGTT | 5842 |
| AAAACTGGGA | CAGGGGAGAA | CCTAGGGTGA | TATTAACCAG | GGGCCATGAA TCACCTTTTG | 5902 |
| GTCTGGAGGG | AAGCCTTGGG | GCTGATCGAG | TTGTTGCCCA | CAGCTGTATG ATTCCCAGCC | 5962 |
| AGACACAGCC | TCTTAGATGC | AGTTCTGAAG | AAGATGGTAC | CACCAGTCTG ACTGTTTCCA | 6022 |
| TCAAGGGTAC | ACTGCCTTCT | CAACTCCAAA | CTGACTCTTA | AGAAGACTGC ATTATATTTA | 6082 |
| TTACTGTAAG | AAAATATCAC | TTGTCAATAA | AATCCATACA | TTTGTGT | 6129 |

( 2 ) INFORMATION FOR SEQ ID NO:2:

( i ) SEQUENCE CHARACTERISTICS:
        ( A ) LENGTH: 1480 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
     50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
             100                 105                 110

Asn Lys Glu Glu Arg Ser Ile Ala Ile Tyr Leu Gly Ile Gly Leu Cys
         115                 120                 125

Leu Leu Phe Ile Val Arg Thr Leu Leu Leu His Pro Ala Ile Phe Gly
 130                 135                 140

Leu His His Ile Gly Met Gln Met Arg Ile Ala Met Phe Ser Leu Ile
 145             150                 155                 160

Tyr Lys Lys Thr Leu Lys Leu Ser Ser Arg Val Leu Asp Lys Ile Ser
                 165                 170                 175

Ile Gly Gln Leu Val Ser Leu Leu Ser Asn Asn Leu Asn Lys Phe Asp
             180                 185                 190

Glu Gly Leu Ala Leu Ala His Phe Val Trp Ile Ala Pro Leu Gln Val
         195                 200                 205

Ala Leu Leu Met Gly Leu Ile Trp Glu Leu Leu Gln Ala Ser Ala Phe
 210             215                 220

Cys Gly Leu Gly Phe Leu Ile Val Leu Ala Leu Phe Gln Ala Gly Leu
 225                 230                 235                 240

Gly Arg Met Met Met Lys Tyr Arg Asp Gln Arg Ala Gly Lys Ile Ser
                 245                 250                 255

Glu Arg Leu Val Ile Thr Ser Glu Met Ile Glu Asn Ile Gln Ser Val
             260                 265                 270

Lys Ala Tyr Cys Trp Glu Glu Ala Met Glu Lys Met Ile Glu Asn Leu
         275                 280                 285

Arg Gln Thr Glu Leu Lys Leu Thr Arg Lys Ala Ala Tyr Val Arg Tyr
     290                 295                 300

Phe Asn Ser Ser Ala Phe Phe Phe Ser Gly Phe Phe Val Val Phe Leu
 305             310                 315                 320

Ser Val Leu Pro Tyr Ala Leu Ile Lys Gly Ile Ile Leu Arg Lys Ile
             325                 330                 335

Phe Thr Thr Ile Ser Phe Cys Ile Val Leu Arg Met Ala Val Thr Arg
             340                 345                 350

Gln Phe Pro Trp Ala Val Gln Thr Trp Tyr Asp Ser Leu Gly Ala Ile
         355                 360                 365

Asn Lys Ile Gln Asp Phe Leu Gln Lys Gln Glu Tyr Lys Thr Leu Glu
 370                 375                 380

Tyr Asn Leu Thr Thr Thr Glu Val Val Met Glu Asn Val Thr Ala Phe
 385                 390                 395                 400

Trp Glu Glu Gly Phe Gly Glu Leu Phe Glu Lys Ala Lys Gln Asn Asn
                 405                 410                 415

Asn Asn Arg Lys Thr Ser Asn Gly Asp Asp Ser Leu Phe Phe Ser Asn
```

-continued

|  |  |  | 420 |  |  |  | 425 |  |  |  | 430 |  |  |
|---|---|---|---|---|---|---|---|---|---|---|---|---|---|
| Phe | Ser | Leu<br>435 | Leu | Gly | Thr | Pro | Val<br>440 | Leu | Lys | Asp | Ile | Asn<br>445 | Phe | Lys | Ile |
| Glu | Arg<br>450 | Gly | Gln | Leu | Leu | Ala<br>455 | Val | Ala | Gly | Ser | Thr<br>460 | Gly | Ala | Gly | Lys |
| Thr<br>465 | Ser | Leu | Leu | Met | Met<br>470 | Ile | Met | Gly | Glu | Leu<br>475 | Glu | Pro | Ser | Glu | Gly<br>480 |
| Lys | Ile | Lys | His | Ser<br>485 | Gly | Arg | Ile | Ser | Phe<br>490 | Cys | Ser | Gln | Phe | Ser<br>495 | Trp |
| Ile | Met | Pro | Gly<br>500 | Thr | Ile | Lys | Glu | Asn<br>505 | Ile | Ile | Phe | Gly | Val<br>510 | Ser | Tyr |
| Asp | Glu | Tyr<br>515 | Arg | Tyr | Arg | Ser | Val<br>520 | Ile | Lys | Ala | Cys | Gln<br>525 | Leu | Glu | Glu |
| Asp | Ile<br>530 | Ser | Lys | Phe | Ala | Glu<br>535 | Lys | Asp | Asn | Ile | Val<br>540 | Leu | Gly | Glu | Gly |
| Gly<br>545 | Ile | Thr | Leu | Ser | Gly<br>550 | Gly | Gln | Arg | Ala | Arg<br>555 | Ile | Ser | Leu | Ala | Arg<br>560 |
| Ala | Val | Tyr | Lys | Asp<br>565 | Ala | Asp | Leu | Tyr | Leu<br>570 | Leu | Asp | Ser | Pro | Phe<br>575 | Gly |
| Tyr | Leu | Asp | Val<br>580 | Leu | Thr | Glu | Lys | Glu<br>585 | Ile | Phe | Glu | Ser | Cys<br>590 | Val | Cys |
| Lys | Leu | Met<br>595 | Ala | Asn | Lys | Thr | Arg<br>600 | Ile | Leu | Val | Thr | Ser<br>605 | Lys | Met | Glu |
| His | Leu<br>610 | Lys | Lys | Ala | Asp | Lys<br>615 | Ile | Leu | Ile | Leu | His<br>620 | Glu | Gly | Ser | Ser |
| Tyr<br>625 | Phe | Tyr | Gly | Thr | Phe<br>630 | Ser | Glu | Leu | Gln | Asn<br>635 | Leu | Gln | Pro | Asp | Phe<br>640 |
| Ser | Ser | Lys | Leu | Met<br>645 | Gly | Cys | Asp | Ser | Phe<br>650 | Asp | Gln | Phe | Ser | Ala<br>655 | Glu |
| Arg | Arg | Asn | Ser<br>660 | Ile | Leu | Thr | Glu | Thr<br>665 | Leu | His | Arg | Phe | Ser<br>670 | Leu | Glu |
| Gly | Asp | Ala<br>675 | Pro | Val | Ser | Trp | Thr<br>680 | Glu | Thr | Lys | Lys | Gln<br>685 | Ser | Phe | Lys |
| Gln | Thr<br>690 | Gly | Glu | Phe | Gly | Glu<br>695 | Lys | Arg | Lys | Asn | Ser<br>700 | Ile | Leu | Asn | Pro |
| Ile<br>705 | Asn | Ser | Ile | Arg | Lys<br>710 | Phe | Ser | Ile | Val | Gln<br>715 | Lys | Thr | Pro | Leu | Gln<br>720 |
| Met | Asn | Gly | Ile | Glu<br>725 | Glu | Asp | Ser | Asp | Glu<br>730 | Pro | Leu | Glu | Arg | Arg<br>735 | Leu |
| Ser | Leu | Val | Pro<br>740 | Asp | Ser | Glu | Gln | Gly<br>745 | Glu | Ala | Ile | Leu | Pro<br>750 | Arg | Ile |
| Ser | Val | Ile<br>755 | Ser | Thr | Gly | Pro | Thr<br>760 | Leu | Gln | Ala | Arg | Arg<br>765 | Arg | Gln | Ser |
| Val | Leu<br>770 | Asn | Leu | Met | Thr | His<br>775 | Ser | Val | Asn | Gln | Gly<br>780 | Gln | Asn | Ile | His |
| Arg<br>785 | Lys | Thr | Thr | Ala | Ser<br>790 | Thr | Arg | Lys | Val | Ser<br>795 | Leu | Ala | Pro | Gln | Ala<br>800 |
| Asn | Leu | Thr | Glu | Leu<br>805 | Asp | Ile | Tyr | Ser | Arg<br>810 | Arg | Leu | Ser | Gln | Glu<br>815 | Thr |
| Gly | Leu | Glu | Ile<br>820 | Ser | Glu | Glu | Ile | Asn<br>825 | Glu | Glu | Asp | Leu | Lys<br>830 | Glu | Cys |
| Leu | Phe | Asp<br>835 | Asp | Met | Glu | Ser | Ile<br>840 | Pro | Ala | Val | Thr | Thr<br>845 | Trp | Asn | Thr |

```
Tyr Leu Arg Tyr Ile Thr Val His Lys Ser Leu Ile Phe Val Leu Ile
    850             855             860
Trp Cys Leu Val Ile Phe Leu Ala Glu Val Ala Ala Ser Leu Val Val
865             870             875             880
Leu Trp Leu Leu Gly Asn Thr Pro Leu Gln Asp Lys Gly Asn Ser Thr
            885             890             895
His Ser Arg Asn Asn Ser Tyr Ala Val Ile Ile Thr Ser Thr Ser Ser
            900             905             910
Tyr Tyr Val Phe Tyr Ile Tyr Val Gly Val Ala Asp Thr Leu Leu Ala
            915             920             925
Met Gly Phe Phe Arg Gly Leu Pro Leu Val His Thr Leu Ile Thr Val
    930             935             940
Ser Lys Ile Leu His His Lys Met Leu His Ser Val Leu Gln Ala Pro
945             950             955             960
Met Ser Thr Leu Asn Thr Leu Lys Ala Gly Gly Ile Leu Asn Arg Phe
            965             970             975
Ser Lys Asp Ile Ala Ile Leu Asp Asp Leu Leu Pro Leu Thr Ile Phe
            980             985             990
Asp Phe Ile Gln Leu Leu Leu Ile Val Ile Gly Ala Ile Ala Val Val
        995             1000            1005
Ala Val Leu Gln Pro Tyr Ile Phe Val Ala Thr Val Pro Val Ile Val
1010            1015            1020
Ala Phe Ile Met Leu Arg Ala Tyr Phe Leu Gln Thr Ser Gln Gln Leu
1025            1030            1035            1040
Lys Gln Leu Glu Ser Glu Gly Arg Ser Pro Ile Phe Thr His Leu Val
            1045            1050            1055
Thr Ser Leu Lys Gly Leu Trp Thr Leu Arg Ala Phe Gly Arg Gln Pro
        1060            1065            1070
Tyr Phe Glu Thr Leu Phe His Lys Ala Leu Asn Leu His Thr Ala Asn
            1075            1080            1085
Trp Phe Leu Tyr Leu Ser Thr Leu Arg Trp Phe Gln Met Arg Ile Glu
        1090            1095            1100
Met Ile Phe Val Ile Phe Phe Ile Ala Val Thr Phe Ile Ser Ile Leu
1105            1110            1115            1120
Thr Thr Gly Glu Gly Glu Gly Arg Val Gly Ile Ile Leu Thr Leu Ala
            1125            1130            1135
Met Asn Ile Met Ser Thr Leu Gln Trp Ala Val Asn Ser Ser Ile Asp
            1140            1145            1150
Val Asp Ser Leu Met Arg Ser Val Ser Arg Val Phe Lys Phe Ile Asp
        1155            1160            1165
Met Pro Thr Glu Gly Lys Pro Thr Lys Ser Thr Lys Pro Tyr Lys Asn
    1170            1175            1180
Gly Gln Leu Ser Lys Val Met Ile Ile Glu Asn Ser His Val Lys Lys
1185            1190            1195            1200
Asp Asp Ile Trp Pro Ser Gly Gly Gln Met Thr Val Lys Asp Leu Thr
            1205            1210            1215
Ala Lys Tyr Thr Glu Gly Gly Asn Ala Ile Leu Glu Asn Ile Ser Phe
        1220            1225            1230
Ser Ile Ser Pro Gly Gln Arg Val Gly Leu Leu Gly Arg Thr Gly Ser
        1235            1240            1245
Gly Lys Ser Thr Leu Leu Ser Ala Phe Leu Arg Leu Leu Asn Thr Glu
    1250            1255            1260
Gly Glu Ile Gln Ile Asp Gly Val Ser Trp Asp Ser Ile Thr Leu Gln
1265            1270            1275            1280
```

| | | | | | | | | | | | | | | |
|---|---|---|---|---|---|---|---|---|---|---|---|---|---|---|
| Gln | Trp | Arg | Lys | Ala | Phe | Gly | Val | Ile | Pro | Gln | Lys | Val | Phe | Ile | Phe |
| | | | | 1285 | | | | | 1290 | | | | | 1295 | |

| | | | | | | | | | | | | | | |
|---|---|---|---|---|---|---|---|---|---|---|---|---|---|---|
| Ser | Gly | Thr | Phe | Arg | Lys | Asn | Leu | Asp | Pro | Tyr | Glu | Gln | Trp | Ser | Asp |
| | | | 1300 | | | | | 1305 | | | | | 1310 | | |

| | | | | | | | | | | | | | | |
|---|---|---|---|---|---|---|---|---|---|---|---|---|---|---|
| Gln | Glu | Ile | Trp | Lys | Val | Ala | Asp | Glu | Val | Gly | Leu | Arg | Ser | Val | Ile |
| | | | 1315 | | | | | 1320 | | | | | 1325 | | |

| | | | | | | | | | | | | | | |
|---|---|---|---|---|---|---|---|---|---|---|---|---|---|---|
| Glu | Gln | Phe | Pro | Gly | Lys | Leu | Asp | Phe | Val | Leu | Val | Asp | Gly | Gly | Cys |
| | 1330 | | | | | | 1335 | | | | | 1340 | | | |

| | | | | | | | | | | | | | | |
|---|---|---|---|---|---|---|---|---|---|---|---|---|---|---|
| Val | Leu | Ser | His | Gly | His | Lys | Gln | Leu | Met | Cys | Leu | Ala | Arg | Ser | Val |
| 1345 | | | | | 1350 | | | | | 1355 | | | | | 1360 |

| | | | | | | | | | | | | | | |
|---|---|---|---|---|---|---|---|---|---|---|---|---|---|---|
| Leu | Ser | Lys | Ala | Lys | Ile | Leu | Leu | Leu | Asp | Glu | Pro | Ser | Ala | His | Leu |
| | | | | 1365 | | | | | 1370 | | | | | 1375 | |

| | | | | | | | | | | | | | | |
|---|---|---|---|---|---|---|---|---|---|---|---|---|---|---|
| Asp | Pro | Val | Thr | Tyr | Gln | Ile | Ile | Arg | Arg | Thr | Leu | Lys | Gln | Ala | Phe |
| | | | | 1380 | | | | | 1385 | | | | | 1390 | |

| | | | | | | | | | | | | | |
|---|---|---|---|---|---|---|---|---|---|---|---|---|---|
| Ala | Asp | Cys | Thr | Val | Ile | Leu | Cys | Glu | His | Arg | Ile | Glu | Ala | Met | Leu |
| | | | 1395 | | | | | 1400 | | | | | 1405 | | |

| | | | | | | | | | | | | | |
|---|---|---|---|---|---|---|---|---|---|---|---|---|---|
| Glu | Cys | Gln | Gln | Phe | Leu | Val | Ile | Glu | Glu | Asn | Lys | Val | Arg | Gln | Tyr |
| | | | 1410 | | | | | 1415 | | | | | 1420 | | |

| | | | | | | | | | | | | | | |
|---|---|---|---|---|---|---|---|---|---|---|---|---|---|---|
| Asp | Ser | Ile | Gln | Lys | Leu | Leu | Asn | Glu | Arg | Ser | Leu | Phe | Arg | Gln | Ala |
| 1425 | | | | | 1430 | | | | | 1435 | | | | | 1440 |

| | | | | | | | | | | | | | | |
|---|---|---|---|---|---|---|---|---|---|---|---|---|---|---|
| Ile | Ser | Pro | Ser | Asp | Arg | Val | Lys | Leu | Phe | Pro | His | Arg | Asn | Ser | Ser |
| | | | | 1445 | | | | | 1450 | | | | | 1455 | |

| | | | | | | | | | | | | | | |
|---|---|---|---|---|---|---|---|---|---|---|---|---|---|---|
| Lys | Cys | Lys | Ser | Lys | Pro | Gln | Ile | Ala | Ala | Leu | Lys | Glu | Glu | Thr | Glu |
| | | | | 1460 | | | | | 1465 | | | | | 1470 | |

| | | | | | | | |
|---|---|---|---|---|---|---|---|
| Glu | Glu | Val | Gln | Asp | Thr | Arg | Leu |
| | | 1475 | | | | | 1480 |

(2) INFORMATION FOR SEQ ID NO:3:

(i) SEQUENCE CHARACTERISTICS:
        (A) LENGTH: 5635 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

| | | | | | |
|---|---|---|---|---|---|
| CATCATCAAT | AATATACCTT | ATTTTGGATT | GAAGCCAATA | TGATAATGAG | GGGGTGGAGT | 60 |
| TTGTGACGTG | GCGCGGGGCG | TGGGAACGGG | GCGGGTGACG | TAGTAGTGTG | GCGGAAGTGT | 120 |
| GATGTTGCAA | GTGTGGCGGA | ACACATGTAA | GCGCCGGATG | TGGTAAAAGT | GACGTTTTTG | 180 |
| GTGTGCGCCG | GTGTATACGG | GAAGTGACAA | TTTTCGCGCG | GTTTAGGCG | GATGTTGTAG | 240 |
| TAAATTTGGG | CGTAACCAAG | TAATGTTTGG | CCATTTTCGC | GGGAAAACTG | AATAAGAGGA | 300 |
| AGTGAAATCT | GAATAATTCT | GTGTTACTCA | TAGCGCGTAA | TATTTGTCTA | GGGCCGCGGG | 360 |
| GACTTTGACC | GTTTACGTGG | AGACTCGCCC | AGGTGTTTTT | CTCAGGTGTT | TTCCGCGTTC | 420 |
| CGGGTCAAAG | TTGGCGTTTT | ATTATTATAG | TCAGCTGACG | CGCAGTGTAT | TTATACCCGG | 480 |
| TGAGTTCCTC | AAGAGGCCAC | TCTTGAGTGC | CAGCGAGTAG | AGTTTCTCC | TCCGAGCCGC | 540 |
| TCCGAGCTAG | TAACGGCCGC | CAGTGTGCTG | CAGATATCAA | AGTCGACGGT | ACCCGAGAGA | 600 |
| CCATGCAGAG | GTCGCCTCTG | GAAAAGGCCA | GCGTTGTCTC | CAAACTTTTT | TTCAGCTGGA | 660 |
| CCAGACCAAT | TTTGAGGAAA | GGATACAGAC | AGCGCCTGGA | ATTGTCAGAC | ATATACCAAA | 720 |
| TCCCTTCTGT | TGATTCTGCT | GACAATCTAT | CTGAAAAATT | GGAAAGAGAA | TGGGATAGAG | 780 |
| AGCTGGCTTC | AAAGAAAAAT | CCTAAACTCA | TTAATGCCCT | TCGGCGATGT | TTTTTCTGGA | 840 |

```
GATTTATGTT   CTATGGAATC   TTTTTATATT   TAGGGGAAGT   CACCAAAGCA   GTACAGCCTC    900

TCTTACTGGG   AAGAATCATA   GCTTCCTATG   ACCCGGATAA   CAAGGAGGAA   CGCTCTATCG    960

CGATTTATCT   AGGCATAGGC   TTATGCCTTC   TCTTTATTGT   GAGGACACTG   CTCCTACACC   1020

CAGCCATTTT   TGGCCTTCAT   CACATTGGAA   TGCAGATGAG   AATAGCTATG   TTTAGTTTGA   1080

TTTATAAGAA   GACTTTAAAG   CTGTCAAGCC   GTGTTCTAGA   TAAAATAAGT   ATTGGACAAC   1140

TTGTTAGTCT   CCTTTCCAAC   AACCTGAACA   AATTTGATGA   AGGACTTGCA   TTGGCACATT   1200

TCGTGTGGAT   CGCTCCTTTG   CAAGTGGCAC   TCCTCATGGG   GCTAATCTGG   GAGTTGTTAC   1260

AGGCGTCTGC   CTTCTGTGGA   CTTGGTTTCC   TGATAGTCCT   TGCCCTTTTT   CAGGCTGGGC   1320

TAGGGAGAAT   GATGATGAAG   TACAGAGATC   AGAGAGCTGG   GAAGATCAGT   GAAAGACTTG   1380

TGATTACCTC   AGAAATGATT   GAAAACATCC   AATCTGTTAA   GGCATACTGC   TGGGAAGAAG   1440

CAATGGAAAA   AATGATTGAA   AACTTAAGAC   AAACAGAACT   GAAACTGACT   CGGAAGGCAG   1500

CCTATGTGAG   ATACTTCAAT   AGCTCAGCCT   TCTTCTTCTC   AGGGTTCTTT   GTGGTGTTTT   1560

TATCTGTGCT   TCCCTATGCA   CTAATCAAAG   GAATCATCCT   CCGGAAAATA   TTCACCACCA   1620

TCTCATTCTG   CATTGTTCTG   CGCATGGCGG   TCACTCGGCA   ATTTCCCTGG   GCTGTACAAA   1680

CATGGTATGA   CTCTCTTGGA   GCAATAAACA   AAATACAGGA   TTTCTTACAA   AGCAAGAAT   1740

ATAAGACATT   GGAATATAAC   TTAACGACTA   CAGAAGTAGT   GATGGAGAAT   GTAACAGCCT   1800

TCTGGGAGGA   GGGATTTGGG   GAATTATTTG   AGAAAGCAAA   ACAAAACAAT   AACAATAGAA   1860

AAACTTCTAA   TGGTGATGAC   AGCCTCTTCT   TCAGTAATTT   CTCACTTCTT   GGTACTCCTG   1920

TCCTGAAAGA   TATTAATTTC   AAGATAGAAA   GAGGACAGTT   GTTGGCGGTT   GCTGGATCCA   1980

CTGGAGCAGG   CAAGACTTCA   CTTCTAATGA   TGATTATGGG   AGAACTGGAG   CCTTCAGAGG   2040

GTAAAATTAA   GCACAGTGGA   AGAATTTCAT   TCTGTTCTCA   GTTTCCTGG    ATTATGCCTG   2100

GCACCATTAA   AGAAAATATC   ATCTTTGGTG   TTTCCTATGA   TGAATATAGA   TACAGAAGCG   2160

TCATCAAAGC   ATGCCAACTA   GAAGAGGACA   TCTCCAAGTT   TGCAGAGAAA   GACAATATAG   2220

TTCTTGGAGA   AGGTGGAATC   ACACTGAGTG   GAGGTCAACG   AGCAAGAATT   CTTTAGCAA   2280

GAGCAGTATA   CAAAGATGCT   GATTTGTATT   TATTAGACTC   TCCTTTTGGA   TACCTAGATG   2340

TTTTAACAGA   AAAAGAAATA   TTTGAAAGCT   GTGTCTGTAA   ACTGATGGCT   AACAAAACTA   2400

GGATTTTGGT   CACTTCTAAA   ATGGAACATT   TAAAGAAAGC   TGACAAAATA   TTAATTTTGC   2460

ATGAAGGTAG   CAGCTATTTT   TATGGGACAT   TTTCAGAACT   CCAAAATCTA   CAGCCAGACT   2520

TTAGCTCAAA   ACTCATGGGA   TGTGATTCTT   TCGACCAATT   TAGTGCAGAA   AGAAGAAATT   2580

CAATCCTAAC   TGAGACCTTA   CACCGTTTCT   CATTAGAAGG   AGATGCTCCT   GTCTCCTGGA   2640

CAGAAACAAA   AAAACAATCT   TTTAAACAGA   CTGGAGAGTT   TGGGGAAAAA   AGGAAGAATT   2700

CTATTCTCAA   TCCAATCAAC   TCTATACGAA   AATTTCCAT   TGTGCAAAAG   ACTCCCTTAC   2760

AAATGAATGG   CATCGAAGAG   GATTCTGATG   AGCCTTTAGA   GAGAAGGCTG   TCCTTAGTAC   2820

CAGATTCTGA   GCAGGGAGAG   GCGATACTGC   CTCGCATCAG   CGTGATCAGC   ACTGGCCCCA   2880

CGCTTCAGGC   ACGAAGGAGG   CAGTCTGTCC   TGAACCTGAT   GACACACTCA   GTTAACCAAG   2940

GTCAGAACAT   TCACCGAAAG   ACAACAGCAT   CCACACGAAA   AGTGTCACTG   GCCCCTCAGG   3000

CAAACTTGAC   TGAACTGGAT   ATATATTCAA   GAAGGTTATC   TCAAGAAACT   GGCTTGGAAA   3060

TAAGTGAAGA   AATTAACGAA   GAAGACTTAA   AGGAGTGCCT   TTTTGATGAT   ATGGAGAGCA   3120

TACCAGCAGT   GACTACATGG   AACACATACC   TTCGATATAT   TACTGTCCAC   AAGAGCTTAA   3180

TTTTTGTGCT   AATTTGGTGC   TTAGTAATTT   TTCTGGCAGA   GGTGGCTGCT   TCTTTGGTTG   3240
```

```
TGCTGTGGCT CCTTGGAAAC ACTCCTCTTC AAGACAAAGG GAATAGTACT CATAGTAGAA    3300
ATAACAGCTA TGCAGTGATT ATCACCAGCA CCAGTTCGTA TTATGTGTTT TACATTTACG    3360
TGGGAGTAGC CGACACTTTG CTTGCTATGG GATTCTTCAG AGGTCTACCA CTGGTGCATA    3420
CTCTAATCAC AGTGTCGAAA ATTTTACACC ACAAATGTT ACATTCTGTT CTTCAAGCAC     3480
CTATGTCAAC CCTCAACACG TTGAAAGCAG GTGGGATTCT TAATAGATTC TCCAAAGATA    3540
TAGCAATTTT GGATGACCTT CTGCCTCTTA CCATATTTGA CTTCATCCAG TTGTTATTAA    3600
TTGTGATTGG AGCTATAGCA GTTGTCGCAG TTTTACAACC CTACATCTTT GTTGCAACAG    3660
TGCCAGTGAT AGTGGCTTTT ATTATGTTGA GAGCATATTT CCTCCAAACC TCACAGCAAC    3720
TCAAACAACT GGAATCTGAA GGCAGGAGTC CAATTTTCAC TCATCTTGTT ACAAGCTTAA    3780
AAGGACTATG GACACTTCGT GCCTTCGGAC GGCAGCCTTA CTTTGAAACT CTGTTCCACA    3840
AAGCTCTGAA TTTACATACT GCCAACTGGT TCTTGTACCT GTCAACACTG CGCTGGTTCC    3900
AAATGAGAAT AGAAATGATT TTTGTCATCT TCTTCATTGC TGTTACCTTC ATTTCCATTT    3960
TAACAACAGG AGAAGGAGAA GGAAGAGTTG GTATTATCCT GACTTTAGCC ATGAATATCA    4020
TGAGTACATT GCAGTGGGCT GTAAACTCCA GCATAGATGT GGATAGCTTG ATGCGATCTG    4080
TGAGCCGAGT CTTTAAGTTC ATTGACATGC CAACAGAAGG TAAACCTACC AAGTCAACCA    4140
AACCATACAA GAATGGCCAA CTCTCGAAAG TTATGATTAT TGAGAATTCA CACGTGAAGA    4200
AAGATGACAT CTGGCCCTCA GGGGGCCAAA TGACTGTCAA AGATCTCACA GCAAAATACA    4260
CAGAAGGTGG AAATGCCATA TTAGAGAACA TTTCCTTCTC AATAAGTCCT GGCCAGAGGG    4320
TGGGCCTCTT GGGAAGAACT GGATCAGGGA AGAGTACTTT GTTATCAGCT TTTTTGAGAC    4380
TACTGAACAC TGAAGGAGAA ATCCAGATCG ATGGTGTGTC TTGGGATTCA ATAACTTTGC    4440
AACAGTGGAG GAAAGCCTTT GGAGTGATAC CACAGAAAGT ATTTATTTTT TCTGGAACAT    4500
TTAGAAAAAA CTTGGATCCC TATGAACAGT GGAGTGATCA AGAAATATGG AAAGTTGCAG    4560
ATGAGGTTGG GCTCAGATCT GTGATAGAAC AGTTTCCTGG GAAGCTTGAC TTTGTCCTTG    4620
TGGATGGGGG CTGTGTCCTA AGCCATGGCC ACAAGCAGTT GATGTGCTTG GCTAGATCTG    4680
TTCTCAGTAA GGCGAAGATC TTGCTGCTTG ATGAACCCAG TGCTCATTTG GATCCAGTAA    4740
CATACCAAAT AATTAGAAGA ACTCTAAAAC AAGCATTTGC TGATTGCACA GTAATTCTCT    4800
GTGAACACAG GATAGAAGCA ATGCTGGAAT GCCAACAATT TTTGGTCATA GAAGAGAACA    4860
AAGTGCGGCA GTACGATTCC ATCCAGAAAC TGCTGAACGA GAGGAGCCTC TTCCGGCAAG    4920
CCATCAGCCC CTCCGACAGG GTGAAGCTCT TTCCCCACCG GAACTCAAGC AAGTGCAAGT    4980
CTAAGCCCCA GATTGCTGCT CTGAAAGAGG AGACAGAAGA AGAGGTGCAA GATACAAGGC    5040
TTTAGAGAGC AGCATAAATG TTGACATGGG ACATTTGCTC ATGGAATTGG AGGTAGCGGA    5100
TTGAGGTACT GAAATGTGTG GGCGTGGCTT AAGGGTGGGA AAGAATATAT AAGGTGGGGG    5160
TCTCATGTAG TTTTGTATCT GTTTTGCAGC AGCCGCCGCC ATGAGCGCCA ACTCGTTTGA    5220
TGGAAGCATT GTGAGCTCAT ATTTGACAAC GCGCATGCCC CCATGGGCCG GGTGCGTCA    5280
GAATGTGATG GGCTCCAGCA TTGATGGTCG CCCCGTCCTG CCCGCAAACT CTACTACCTT    5340
GACCTACGAG ACCGTGTCTG GAACGCCGTT GGAGACTGCA GCCTCCGCCG CCGCTTCAGC    5400
CGCTGCAGCC ACCGCCCGCG GGATTGTGAC TGACTTTGCT TTCCTGAGCC CGCTTGCAAG    5460
CAGTGCAGCT TCCCGTTCAT CCGCCCGCGA TGACAAGTTG ACGGCTCTTT TGGCACAATT    5520
GGATTCTTTG ACCCGGGAAC TTAATGTCGT TTCTCAGCAG CTGTTGGATC TGCGCCAGCA    5580
GGTTTCTGCC CTGAAGGCTT CCTCCCCTCC CAATGCGGTT TAAAACATAA ATAAA         5635
```

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

ACTCTTGAGT GCCAGCGAGT AGAGTTTTCT CCTCCG        36

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GCAAAGGAGC GATCCACACG AAATGTGCC        29

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CTCCTCCGAG CCGCTCCGAG CTAG        24

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CCAAAAATGG CTGGGTGTAG GAGCAGTGTC C        31

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

CGGATCCTTT ATTATAGGGG AAGTCCACGC CTAC        34

( 2 ) INFORMATION FOR SEQ ID NO:9:

( i ) SEQUENCE CHARACTERISTICS:

(A) LENGTH: 32 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

CGGGATCCAT CGATGAAATA TGACTACGTC CG                                            32

(2) INFORMATION FOR SEQ ID NO:10:

(i) SEQUENCE CHARACTERISTICS:
    (A) LENGTH: 170 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:10:

GTACGGTTGA TCTTCTCCAT TCCCCGAGTG GTCAAGTTTT AGACTTCACC TCTGTCCTGG              60

ACTCCACTGT TACTGTAGAT GAGACTGTAA GAGAGGAGTC CTGTAGAGGT TCAAACGTCT             120

CTTTCTGTTA TATCAAGAAC CTCTTCCACC TTAGTGTGAC TCACCTCCAG                        170